United States Patent
Jacobs, Jr. et al.

(10) Patent No.: US 8,394,388 B2
(45) Date of Patent: Mar. 12, 2013

(54) MYCOBACTERIAL MUTANTS AFFECTING HOST APOPTOSIS

(75) Inventors: William R. Jacobs, Jr., Pelham, NY (US); Steven A. Porcelli, Bronx, NY (US); Volker Briken, Burtonsville, MD (US); Miriam Braunstein, Chapel Hill, NC (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 706 days.

(21) Appl. No.: 11/794,506

(22) PCT Filed: Jan. 12, 2006

(86) PCT No.: PCT/US2006/001132
§ 371 (c)(1),
(2), (4) Date: Jan. 11, 2010

(87) PCT Pub. No.: WO2006/076519
PCT Pub. Date: Jul. 20, 2006

(65) Prior Publication Data
US 2010/0297185 A1 Nov. 25, 2010

Related U.S. Application Data

(60) Provisional application No. 60/643,614, filed on Jan. 12, 2005.

(51) Int. Cl.
*A61K 39/04* (2006.01)
*C12N 1/20* (2006.01)
(52) U.S. Cl. ................. 424/248.1; 424/184.1; 435/253.1
(58) Field of Classification Search .................. None
See application file for complete search history.

(56) References Cited

U.S. PATENT DOCUMENTS

| | | | |
|---|---|---|---|
| 6,372,478 | B1 | 4/2002 | Bloom |
| 6,733,761 | B2 | 5/2004 | McKinney |
| 6,752,994 | B2 | 6/2004 | Jacobs, Jr. |
| 6,821,769 | B2 | 11/2004 | Alland |
| 7,722,861 | B2 | 5/2010 | Jacobs |
| 7,758,874 | B2 | 7/2010 | Jacobs, Jr. |
| 7,939,089 | B2 | 5/2011 | Jacobs |
| 7,998,471 | B2 | 8/2011 | Jacobs, Jr. |
| 2007/0202131 | A1 | 8/2007 | Jacobs, Jr. |
| 2009/0110696 | A1 | 4/2009 | Jacobs, Jr. |

FOREIGN PATENT DOCUMENTS
WO WO 2004/067718 A2 8/2004

OTHER PUBLICATIONS

Jalapathy, Kripa [Ph.D.] et al, 2004 Dissertation, abstract only.*
Notification of Transmittal of the International Search Report and the Written Opinion of the International Searching Authority, or the Declaration (1 page) for related application PCT/US2006/001132 with an international filing date of Jan. 12, 2006.
International Search Report (6 pages) for related application PCT/US2006/001132 with an international filing date of Jan. 12, 2006.
Written Opinion of the International Searching Authority (5 pages) for related application PCT/US2006/001132 with an international filing date of Jan. 12, 2006.
Braunstein et al., entitled "SecA2 functions in the secretion of superoxide dismutase A and in the virulence of *Mycobacterium tuberculosis*," Molecular Microbiology, 2003, vol. 48, No. 2, pp. 453-464.
Ciaramella et al., entitled "Mycobacterial 19-kDa lipoprotein mediates *Mycobacterium tuberculosis*-induced apoptosis in monocytes/macrophages at early stages of infection," Cell Death and Differentiation, 2000, vol. 7, pp. 1270-1272.
U.S. Appl. No. 12/450,193, filed Mar. 10, 2008.
Communication pursuant to Article 94(3) EPC regarding Application No. 06733693.3 dated Nov. 14, 2011.
Canadian Office Action dated Feb. 13, 2012 corresponding to Canadian Application No. 2,597,698.
European Search Report for European Application No. EP 06 73 369.3, 2006.
Abstract: "Full-Probable Conserved Integral Membrane Protein." Database Accession No. 005883, Jul. 1997.
Kramer et al. "Isoprenylcysteine Carboxyl Methyltransferase Activity Modulates Endothelial Cell Apoptosis." Molecular Biology of the Cell, 14:2003, pp. 848-857.
Hinchey, et al. "Enhanced Priming of Adaptive Immunity by a Proapoptotic Mutant of *Mycobacterium tuberculosis*." The J. Clin. Inves., 117:8, 2007, pp. 2279-2288.

* cited by examiner

*Primary Examiner* — Padma V Baskar
(74) *Attorney, Agent, or Firm* — Rothstein & Ebenstein LLP

(57) ABSTRACT

Provided are recombinant *mycobacteria* having a mutation in an nlaA gene or in a nuoG gene. Also provided are isolated and purified nlaA proteins and nuoG proteins from a *mycobacterium*. Additionally provided are isolated and purified nucleic acids comprising a recombinant nlaA gene or a recombinant nuoG gene. Further provided are methods of inducing an immune response in a mammal and methods of making a recombinant *mycobacterium* using the nlaA gene or the nuoG gene.

14 Claims, 36 Drawing Sheets

*M. tuberculosis* H37Rv

*M. tuberculosis* ΔnlaA

SEQUENCE LISTING

<160> NUMBER OF SEQ ID NOS: 6

<210> SEQ ID NO 1
<211> LENGTH: 244
<212> TYPE: PRT
<213> ORGANISM: Mycobacterium tuberculosis

<400> SEQUENCE: 1

Met Lys Arg Tyr Leu Thr Ile Ile Tyr Gly Ala Ala Ser Tyr Leu Val
1               5                   10                  15

Phe Leu Val Ala Phe Gly Tyr Ala Ile Gly Phe Val Gly Asp Val Val
            20                  25                  30

Val Pro Arg Thr Val Asp His Ala Ile Ala Ala Pro Ile Gly Gln Ala
        35                  40                  45

Val Val Val Asn Leu Val Leu Leu Gly Val Phe Ala Val Gln His Ser
    50                  55                  60

Val Met Ala Arg Gln Gly Phe Lys Arg Trp Trp Thr Arg Phe Val Pro
65                  70                  75                  80

Pro Ser Ile Glu Arg Ser Thr Tyr Val Leu Leu Ala Ser Val Ala Leu
                85                  90                  95

Leu Leu Leu Tyr Trp Gln Trp Arg Thr Met Pro Ala Val Ile Trp Asp
            100                 105                 110

Val Arg Gln Pro Ala Gly Arg Val Ala Leu Trp Ala Leu Phe Trp Leu
        115                 120                 125

Gly Trp Ala Thr Val Leu Thr Ser Thr Phe Met Ile Asn His Phe Glu
    130                 135                 140

Leu Phe Gly Leu Arg Gln Val Tyr Leu Ala Trp Arg Gly Lys Pro Tyr
145                 150                 155                 160

Thr Glu Ile Gly Phe Gln Ala His Leu Leu Tyr Arg Trp Val Arg His
                165                 170                 175

Pro Ile Met Leu Gly Phe Val Val Ala Phe Trp Ala Thr Pro Met Met
            180                 185                 190

Thr Ala Gly His Leu Leu Phe Ala Ile Gly Ala Thr Gly Tyr Ile Leu
        195                 200                 205

Val Ala Leu Gln Phe Glu Glu Arg Asp Leu Leu Ala Leu Gly Asp
    210                 215                 220

Gln Tyr Arg Asp Tyr Arg Arg Glu Val Ser Met Leu Leu Pro Trp Pro
225                 230                 235                 240

His Arg His Thr

<210> SEQ ID NO 2
<211> LENGTH: 735
<212> TYPE: DNA
<213> ORGANISM: Mycobacterium tuberculosis

<400> SEQUENCE: 2

```
atgaagcgtt atttgacgat catttacggg gccgcgagct atctggtatt cctggttgcc      60
ttcgggtatg cgatcggttt cgtcggcgac gtagtggtgc cacgaaccgt agatcacgcg     120
atcgcggcgc cgatcggcca ggcggtcgtg gtcaacttgg tgctgctggg cgtgttcgcc     180
gtccaacata gcgtgatggc acgacagggt ttcaaacgct ggtggactcg attcgtgccg     240
ccctcgatcg agcgcagcac ctatgtactg ctggccagcg ttgcgctgtt gttgctgtac     300
tggcaatggc gaacgatgcc ggcggtcatc tgggacgtgc ggcagccggc tggccgggtg     360
gcgttgtggg cgttgttctg gctcgggtgg gccacggtgt tgacgtcgac tttcatgatc     420
aatcatttcg aattgttcgg cctacggcag gtgtatttgg cttggcgcgg aaagccgtac     480
accgagatcg gttttcaggc tcatctgctc taccggtggg tacgccaccc gatcatgctc     540
ggattcgtcg tcgcgttctg ggcgacgccc atgatgacgg cggggcactt gcttttcgcg     600
atcggcgcga cgggctacat cttggtcgcg ttgcagttcg aagagcgcga cctactcgcg     660
gcgctgggcg accaataccg cgattaccgc cgcgaggtgt cgatgttgtt gccgtggccg     720
caccggcata cctga                                                      735
```

<210> SEQ ID NO 3
<211> LENGTH: 791
<212> TYPE: PRT
<213> ORGANISM: Mycobacterium tuberculosis

<400> SEQUENCE: 3

```
Met Val Thr Leu Thr Ile Asp Gly Val Glu Ile Ser Val Pro Lys Gly
  1               5                  10                  15

Thr Leu Val Ile Arg Ala Ala Glu Leu Met Gly Ile Gln Ile Pro Arg
             20                  25                  30

Phe Cys Asp His Pro Leu Leu Glu Pro Val Gly Ala Cys Arg Gln Cys
         35                  40                  45

Leu Val Glu Val Glu Gly Gln Arg Lys Pro Leu Ala Ser Cys Thr Thr
     50                  55                  60

Val Ala Thr Asp Asp Met Val Val Arg Thr Gln Leu Thr Ser Glu Ile
 65                  70                  75                  80

Ala Asp Lys Ala Gln His Gly Val Met Glu Leu Leu Ile Asn His
                 85                  90                  95

Pro Leu Asp Cys Pro Met Cys Asp Lys Gly Gly Glu Cys Pro Leu Gln
            100                 105                 110

Asn Gln Ala Met Ser Asn Gly Arg Thr Asp Ser Arg Phe Thr Glu Ala
        115                 120                 125

Lys Arg Thr Phe Ala Lys Pro Ile Asn Ile Ser Ala Gln Val Leu Leu
    130                 135                 140

Asp Arg Glu Arg Cys Ile Leu Cys Ala Arg Cys Thr Arg Phe Ser Asp
145                 150                 155                 160

Gln Ile Ala Gly Asp Pro Phe Ile Asp Met Gln Glu Arg Gly Ala Leu
                165                 170                 175

Gln Gln Val Gly Ile Tyr Ala Asp Glu Pro Phe Glu Tyr Phe Ser
            180                 185                 190

Gly Asn Thr Val Gln Ile Cys Pro Val Gly Ala Leu Thr Gly Thr Ala
        195                 200                 205

Tyr Arg Phe Arg Ala Arg Pro Phe Asp Leu Val Ser Ser Pro Ser Val
    210                 215                 220

Cys Glu His Cys Ala Ser Gly Cys Ala Gln Arg Thr Asp His Arg Arg
225                 230                 235                 240
```

```
Gly Lys Val Leu Arg Arg Leu Ala Gly Asp Asp Pro Glu Val Asn Glu
                245                 250                 255

Glu Trp Asn Cys Asp Lys Gly Arg Trp Ala Phe Thr Tyr Ala Thr Gln
            260                 265                 270

Pro Asp Val Ile Thr Thr Pro Leu Ile Arg Asp Gly Gly Asp Pro Lys
        275                 280                 285

Gly Ala Leu Val Pro Thr Ser Trp Ser His Ala Met Ala Val Ala Ala
    290                 295                 300

Gln Gly Leu Ala Ala Arg Gly Arg Thr Gly Val Leu Val Gly Gly
305                 310                 315                 320

Arg Val Thr Trp Glu Asp Ala Tyr Ala Tyr Ala Lys Phe Ala Arg Ile
                325                 330                 335

Thr Leu Gly Thr Asn Asp Ile Asp Phe Arg Ala Arg Pro His Ser Ala
            340                 345                 350

Glu Glu Ala Asp Phe Leu Ala Ala Arg Ile Ala Gly Arg His Met Ala
        355                 360                 365

Val Ser Tyr Ala Asp Leu Glu Ser Ala Pro Val Val Leu Leu Val Gly
    370                 375                 380

Phe Glu Pro Glu Asp Glu Ser Pro Ile Val Phe Leu Arg Leu Arg Lys
385                 390                 395                 400

Ala Ala Arg Arg His Arg Val Pro Val Tyr Thr Ile Ala Pro Phe Ala
                405                 410                 415

Thr Gly Gly Leu His Lys Met Ser Gly Arg Leu Ile Lys Thr Val Pro
            420                 425                 430

Gly Gly Glu Pro Ala Ala Leu Asp Asp Leu Ala Thr Gly Ala Val Gly
        435                 440                 445

Asp Leu Leu Ala Thr Pro Gly Ala Val Ile Ile Val Gly Glu Arg Leu
    450                 455                 460

Ala Thr Val Pro Gly Gly Leu Ser Ala Ala Arg Leu Ala Asp Thr
465                 470                 475                 480

Thr Gly Ala Arg Leu Ala Trp Val Pro Arg Arg Ala Gly Glu Arg Gly
                485                 490                 495

Ala Leu Glu Ala Gly Ala Leu Pro Thr Leu Pro Gly Gly Arg Pro
            500                 505                 510

Leu Ala Asp Glu Val Ala Arg Ala Gln Val Cys Ala Ala Trp His Ile
        515                 520                 525

Ala Glu Leu Pro Ala Ala Ala Gly Arg Asp Ala Asp Gly Ile Leu Ala
    530                 535                 540

Ala Ala Ala Asp Glu Thr Leu Ala Ala Leu Leu Val Gly Gly Ile Glu
545                 550                 555                 560

Pro Ala Asp Phe Ala Asp Pro Asp Ala Val Leu Ala Ala Leu Asp Ala
                565                 570                 575

Thr Gly Phe Val Val Ser Leu Glu Leu Arg His Ser Thr Val Thr Glu
            580                 585                 590

Arg Ala Asp Val Val Phe Pro Val Ala Pro Thr Thr Gln Lys Ala Gly
        595                 600                 605

Ala Phe Val Asn Trp Glu Gly Arg Tyr Arg Thr Phe Glu Pro Ala Leu
    610                 615                 620

Arg Gly Ser Thr Leu Gln Ala Gly Gln Ser Asp His Arg Val Leu Asp
625                 630                 635                 640

Ala Leu Ala Asp Asp Met Gly Val His Leu Gly Val Pro Thr Val Glu
                645                 650                 655

Ala Ala Arg Glu Glu Leu Ala Ala Leu Gly Ile Trp Asp Gly Lys His
            660                 665                 670
```

```
              Ala Ala Gly Pro His Ile Ala Ala Thr Gly Pro Thr Gln Pro Glu Ala
                      675                 680                 685

Gly Glu Ala Ile Leu Thr Gly Trp Arg Met Leu Leu Asp Glu Gly Arg
                  690                 695                 700

Leu Gln Asp Gly Glu Pro Tyr Leu Ala Gly Thr Ala Arg Thr Pro Val
              705                 710                 715                 720

Val Arg Leu Ser Pro Asp Thr Ala Ala Glu Ile Gly Ala Ala Asp Gly
                              725                 730                 735

Glu Ala Val Thr Val Ser Thr Ser Arg Gly Ser Ile Thr Leu Pro Cys
                          740                 745                 750

Ser Val Thr Asp Met Pro Asp Arg Val Val Trp Leu Pro Leu Asn Ser
                      755                 760                 765

Ala Gly Ser Thr Val His Arg Gln Leu Arg Val Thr Ile Gly Ser Ile
                  770                 775                 780

Val Lys Ile Gly Ala Gly Ser
              785                 790

<210> SEQ ID NO 4
<211> LENGTH: 2421
<212> TYPE: DNA
<213> ORGANISM: Mycobacterium tuberculosis

<400> SEQUENCE: 4
gtgacccagg cggccgacac tgacatccgg gtaggccaac cggagatggt gacactgacc        60
atcgacggcg tcgaaatcag cgtccccaag ggcacgttgg tgattcgcgc cgccgaactg       120
atgggaatcc agatcccgcg attctgcgac cacccgctgc tggagcccgt cggcgcctgc       180
cggcaatgcc tggtcgaggt cgaagggcaa cgcaagccgc tggcgtcgtg caccaccgtg       240
gccaccgacg acatggtggt gcgcacccaa ctcacctccg agattgccga caaggcccag       300
cacggtgtga tggaactgct gctgatcaac catccgctgg attgcccgat gtgcgacaag       360
ggcggtgaat gcccgctgca aaaccaggca atgtctaacg gccgcacgga ttctcgcttc       420
accgaggcca acgtaccttt cgccaaaccg atcaacatct ccgcgcaggt gctgctggac       480
cgcgaacgtt gcatcctgtg cgcccgctgc accggttct ccgaccagat cgccggcgat        540
ccgttcatcg atatgcagga gcgcggcgcc ctgcagcagg tcggtatcta cgccgatgaa       600
ccgttcgagt cgtacttctc cggcaacacg gtgcagatct gcccggtggg ggcgctaacg       660
gggaccgcct accggttccg cgcgcgtccg ttcgatttgg tctccagccc cagcgtctgc       720
gagcactgcg cgtcgggctg cgcgcaacgc accgaccatc gccgcggcaa ggtgctgcgg       780
cggctggccg gtgacgaccc ggaagtcaac gaggagtgga actgcgacaa gggccggtgg       840
gccttcacgt acgcgaccca gccggacgtg atcaccactc ccctgatccg cgacggtggg       900
gaccccaagg gcgcgctggt gcccaccctcg tggtcgcacg caatggcggt ggccgcccag       960
ggactggcgg cagcgcgggg ccgcaccggg gtgctggtcg gcggccgagt gacctgggag      1020
gacgcctacg cgtacgccaa gttcgcgcgg atcacgttgg caccaacga catcgacttc       1080 cgcgcccggc cgcactcggc cgaggaggcc gacttcctgg cggcccgcat cgccgggcgg      1140
catatggcgg tcagctatgc cgatttggaa tcggctccgg tggtgctgct ggtgggattc      1200
gagcccgaag acgagtcgcc gatcgtgttt ctgcggttac gcaaggccgc tcgcagacac      1260
cgcgtcccgg tgtacacgat cgcccccttt gccactggtg gcctgcacaa aatgtcgggc      1320
cggctgatca aaaccgttcc tggtggcgaa cccgcgcgc tggacgatct ggccaccggt        1380
gcagtgggcg acctgctggc cacccccggg gcggtcatca tagtcgggga cgcgcttggcc     1440
```

```
acggtaccgg gcggattgtc ggcggccgct cggctggccg atacgaccgg cgcccgtttg   1500
gcgtgggtgc cgcggcgggc gggggaacgc ggagcgctgg aagccggagc gttgcccacg   1560
ctgttacccg gtggccgccc gctggccgac gaggtcgccc gcgcgcaggt gtgtgcggcg   1620
tggcatatcg ccgaattgcc tgccgcggct ggacgggacg ccgacggcat cctggccgcc   1680
gctgccgacg agacgttggc tgcgctgctg gtcgggggta tcgaacccgc ggacttcgcc   1740
gacccggacg ccgtgctggc cgcgttggac gccaccggtt tcgtggtcag cctggagctg   1800
cgacacagta cggtcaccga acgcgccgac gtggtgttcc cggtcgcgcc gacgacccag   1860
aaagccggcg cgttcgtcaa ctgggagggt cgctaccgta cattcgaacc cgcgctgcgc   1920
ggcagcacac tgcaagctgg ccagtcggat caccgggtgc tggacgcgtt ggccgacgac   1980
atgggtgtcc atctgggcgt gcccaccgtg gaggcggccc gcgaggagct ggccgcgctc   2040
ggtatctggg acggcaaaca cgctgccggt ccccacatcg cggccaccgg gccgacccaa   2100
cccgaagctg gtgaggcgat cttgaccggg tgcggatgc tcctcgacga gggccgcctg   2160
caggacggcg aaccatatct ggccggtacc gcgcgcacac ccgtggtacg gctgtcgccg   2220
gatacggcag ccgagatcgg cgccgccgat ggcgaggcgg tcacggtcag cacgtcacgc   2280
ggctcaatca ccttgccgtg cagtgtcacc gacatgcccg accgcgtcgt gtggcttccg   2340
ctgaactcgg cgggctcgac ggtgcaccga cagctgaggg tgacaatcgg cagcatcgtg   2400
aaaatcggag cgggctcatg a                                            2421
```

<210> SEQ ID NO 5
<211> LENGTH: 808
<212> TYPE: PRT
<213> ORGANISM: Mycobacterium tuberculosis

<400> SEQUENCE: 5

```
Met Asn Val His Gly Cys Pro Arg Ile Ala Ala Cys Arg Cys Thr Asp
1               5                   10                  15

Thr His Pro Arg Gly Arg Pro Ala Phe Ala Tyr Arg Trp Phe Val Pro
            20                  25                  30

Lys Thr Thr Arg Ala Gln Pro Gly Arg Leu Ser Ser Arg Phe Trp Arg
        35                  40                  45

Leu Leu Gly Ala Ser Thr Glu Lys Asn Arg Ser Arg Ser Leu Ala Asp
    50                  55                  60

Val Thr Ala Ser Ala Glu Tyr Asp Lys Glu Ala Ala Asp Leu Ser Asp
65                  70                  75                  80

Glu Lys Leu Arg Lys Ala Ala Gly Leu Leu Asn Leu Asp Asp Leu Ala
                85                  90                  95

Glu Ser Ala Asp Ile Pro Gln Phe Leu Ala Ile Ala Arg Glu Ala Ala
            100                 105                 110

Glu Arg Arg Thr Gly Leu Arg Pro Phe Asp Val Gln Leu Leu Gly Ala
        115                 120                 125

Leu Arg Met Leu Ala Gly Asp Val Ile Glu Met Ala Thr Gly Glu Gly
    130                 135                 140

Lys Thr Leu Ala Gly Ala Ile Ala Ala Ala Gly Tyr Ala Leu Ala Gly
145                 150                 155                 160

Arg His Val His Val Thr Ile Asn Asp Tyr Leu Ala Arg Arg Asp
                165                 170                 175

Ala Glu Trp Met Gly Pro Leu Leu Asp Ala Met Gly Leu Thr Val Gly
            180                 185                 190

Trp Ile Thr Ala Asp Ser Thr Pro Asp Glu Arg Arg Thr Ala Tyr Asp
```

```
            195                 200                 205
Arg Asp Val Thr Tyr Ala Ser Val Asn Glu Ile Gly Phe Asp Val Leu
210                 215                 220

Arg Asp Gln Leu Val Thr Asp Val Asn Asp Leu Val Ser Pro Asn Pro
225                 230                 235                 240

Asp Val Ala Leu Ile Asp Glu Ala Asp Ser Val Leu Val Asp Glu Ala
                    245                 250                 255

Leu Val Pro Leu Val Leu Ala Gly Thr Thr His Arg Glu Thr Pro Arg
                260                 265                 270

Leu Glu Ile Ile Arg Leu Val Ala Glu Leu Val Gly Asp Lys Asp Ala
            275                 280                 285

Asp Glu Tyr Phe Ala Thr Asp Ser Asp Asn Arg Asn Val His Leu Thr
        290                 295                 300

Glu His Gly Ala Arg Lys Val Glu Lys Ala Leu Gly Gly Ile Asp Leu
305                 310                 315                 320

Tyr Ser Glu Glu His Val Gly Thr Thr Leu Thr Glu Val Asn Val Ala
                    325                 330                 335

Leu His Ala His Val Leu Leu Gln Arg Asp Val His Tyr Ile Val Arg
                340                 345                 350

Asp Asp Ala Val His Leu Ile Asn Ala Ser Arg Gly Arg Ile Ala Gln
            355                 360                 365

Leu Gln Arg Trp Pro Asp Gly Leu Gln Ala Ala Glu Ala Lys Glu
        370                 375                 380

Gly Ile Glu Thr Thr Glu Thr Gly Glu Val Leu Asp Thr Ile Thr Val
385                 390                 395                 400

Gln Ala Leu Ile Asn Arg Tyr Ala Thr Val Cys Gly Met Thr Gly Thr
                    405                 410                 415

Ala Leu Ala Ala Gly Glu Gln Leu Arg Gln Phe Tyr Gln Leu Gly Val
                420                 425                 430

Ser Pro Ile Pro Pro Asn Lys Pro Asn Ile Arg Glu Asp Glu Ala Asp
            435                 440                 445

Arg Val Tyr Ile Thr Thr Ala Ala Lys Asn Asp Gly Ile Val Glu His
450                 455                 460

Ile Thr Glu Val His Gln Arg Gly Gln Pro Val Leu Val Gly Thr Arg
465                 470                 475                 480

Asp Val Ala Glu Ser Glu Glu Leu His Glu Arg Leu Val Arg Arg Gly
                    485                 490                 495

Val Pro Ala Val Val Leu Asn Ala Lys Asn Asp Ala Glu Glu Ala Arg
                500                 505                 510

Val Ile Ala Glu Ala Gly Lys Tyr Gly Ala Val Thr Val Ser Thr Gln
            515                 520                 525

Met Ala Gly Arg Gly Thr Asp Ile Arg Leu Gly Gly Ser Asp Glu Ala
        530                 535                 540

Asp His Asp Arg Val Ala Glu Leu Gly Gly Leu His Val Val Gly Thr
545                 550                 555                 560

Gly Arg His His Thr Glu Arg Leu Asp Asn Gln Leu Arg Gly Arg Ala
                    565                 570                 575

Gly Arg Gln Gly Asp Pro Gly Ser Ser Val Phe Phe Ser Ser Trp Glu
                580                 585                 590

Asp Asp Val Val Ala Ala Asn Leu Asp His Asn Lys Leu Pro Met Ala
            595                 600                 605

Thr Asp Glu Asn Gly Arg Ile Val Ser Pro Arg Thr Gly Ser Leu Leu
        610                 615                 620
```

```
Asp His Ala Gln Arg Val Ala Glu Gly Arg Leu Leu Asp Val His Ala
625                 630                 635                 640

Asn Thr Trp Arg Tyr Asn Gln Leu Ile Ala Gln Gln Arg Ala Ile Ile
            645                 650                 655

Val Glu Arg Arg Asn Thr Leu Leu Arg Thr Val Thr Ala Arg Glu Glu
        660                 665                 670

Leu Ala Glu Leu Ala Pro Lys Arg Tyr Glu Glu Leu Ser Asp Lys Val
    675                 680                 685

Ser Glu Glu Arg Leu Glu Thr Ile Cys Arg Gln Ile Met Leu Tyr His
690                 695                 700

Leu Asp Arg Gly Trp Ala Asp His Leu Ala Tyr Leu Ala Asp Ile Arg
705                 710                 715                 720

Glu Ser Ile His Leu Arg Ala Leu Gly Arg Gln Asn Pro Leu Asp Glu
            725                 730                 735

Phe His Arg Met Ala Val Asp Ala Phe Ala Ser Leu Ala Ala Asp Ala
        740                 745                 750

Ile Glu Ala Ala Gln Gln Thr Phe Glu Thr Ala Asn Val Leu Asp His
    755                 760                 765

Glu Pro Gly Leu Asp Leu Ser Lys Leu Ala Arg Pro Thr Ser Thr Trp
770                 775                 780

Thr Tyr Met Val Asn Asp Asn Pro Leu Ser Asp Asp Thr Leu Ser Ala
785                 790                 795                 800

Leu Ser Leu Pro Gly Val Phe Arg
                805

<210> SEQ ID NO 6
<211> LENGTH: 2427
<212> TYPE: DNA
<213> ORGANISM: Mycobacterium tuberculosis

<400> SEQUENCE: 6
gtgaacgtgc acggttgtcc acgaattgcg gcctgtcggt gtacagacac gcaccctcgc        60
ggccggccgg cattcgcgta ccgttggttt gtgcccaaga ccacccgcgc tcaacccggc       120
cggctgagca gccgattctg gcgattgctc ggcgccagca ccgaaaagaa ccggagccgc       180
tccctggcgg atgtaaccgc ttcggcagaa tacgacaagg aagctgccga tctgtccgac       240
gagaagctgc gtaaggcggc aggcctgctc aacctcgacg acctcgcgga gtccgccgat       300
atcccgcagt ttctcgcgat tgccggggaa gccgccgagc ggaggaccgg gctgcgacca       360
tttgatgtgc agttgcttgg cgcgttcgcg atgctcgccg agacgtgat cgagatggcc        420 accggtgagg gcaaaaccct tgccggggcg atcgcggccg ccggttatgc gctggccggc       480
cggcacgtgc acgtcgtgac gattaacgat tacctggccc gccgcgatgc ggagtggatg       540
ggcccgctgc tggacgcgat gggcctgacg gtcggctgga tcaccgcgga ctcgacccct       600
gacgagcgcc ggaccgcata tgaccgtgat gtcacctatg cctcggtcaa cgagattggc       660
ttcgatgtac tgcgcgatca gttggtgact gatgtcaatg acctggtatc gcccaatcca       720
gacgtggctc tcatcgacga agccgactcc gtgctggtcg acgaggcgct ggtgcccctg       780
gtgctggccg aaccacaca tcgtgagacg ccgcggctgg agatcatccg gctggtcgct       840
gagcttgttg cgacaaggga cgccgacgag tactttgcca ccgattccga taaccgcaat       900
gtccacttga ccgagcacgg ggcacgcaaa gtcgagaaag cgctcggtgg catcgacctg       960
tactccgagg agcacgtcgg caccacactg actgaggtca atgtcgcgct gcacgcgcat      1020
gtgctcctgc aacgcgacgt gcactacatc gtccgcgacg acgcggtgca cctgatcaac      1080
```

```
                                                -continued gcgtcgcgtg gccgtatcgc gcaactgcag cgctggccgg acgggttgca agctgcggtc   1140
gaggccaagg aaggtatcga gaccacggaa actggggaag tgctcgacac catcacggtg   1200
caggccctga tcaaccggta tgcgactgtg tgcggaatga cgggaaccgc gctggccgcc   1260
ggtgagcagc tacggcagtt ctaccagctc ggtgtctcac cgataccacc gaacaagcca   1320
aacatccgcg aggacgaggc cgaccgggtc tacatcacca ctgcagccaa gaacgacggg   1380
atcgtcgagc acatcaccga ggtgcaccag aggggggcagc ctgtgctggt cggtacccgc   1440
gacgtggccg aatccgagga actgcacgaa cgcctggtgc gccgcggtgt gcccgccgtg   1500
gtgctcaacg cgaagaacga cgccgaggag gcccgggtca tcgccgaggc cggcaaatac   1560
ggcgcggtca cggtgtcaac tcaaatggcc gggcgcggca ccgacatcag gctcggcggg   1620
tccgacgaag ctgaccacga cagggtcgcg gaattgggcg gcctgcacgt ggtcggcact   1680
ggccgtcacc acaccgagcg gctagacaac cagctgcgcg gtcgggccgg cgccaggga   1740 gatcccgggt cgtcggtgtt tttctcaagc tgggaagacg atgtcgttgc ggccaacctc   1800
gaccacaaca agctgccgat ggcaaccgac gaaaatggcc ggattgtcag cccgaggacg   1860
ggtagtctgc tcgaccatgc ccagcgcgtt gccgagggcc ggttattgga tgtgcacgcc   1920
aacacgtggc gctacaacca gctgatcgcc cagcagcgcg ccatcatcgt cgaacggcgt   1980
aacacgttgt tgcgcaccgt aaccgcgcgt gaggaactcg ccgaactggc gcctaagcgg   2040
tacgaggagc tgtccgacaa agtatccgag gaacgcctcg agacgatttg tcggcagatc   2100
atgctgtatc acctcgaccg tggctgggcc gatcacctgg cgtatctggc cgacatccgg   2160
gagagcatcc atctacgcgc gctgggccgg cagaacccac tcgacgagtt tcaccggatg   2220
gctgtggacg cgttcgcgtc gctggccgcc gacgccatcg aggcggctca acagacgttc   2280
gaaaccgcga acgtccttga ccacgagccg gggctggacc tgtccaaact ggcccggccg   2340
acgtcgacat ggacctacat ggtcaatgac aacccactgt ccgatgacac gctttctgcc   2400
ctcagtctgc ccggggtgtt ccgctga                                       2427
```

MYCOBACTERIAL MUTANTS AFFECTING HOST APOPTOSIS

CROSS-REFERENCE TO RELATED APPLICATION

This is a U.S. national phase of PCT Application No. PCT/US2006/001132, filed Jan. 12, 2006, which claims the benefit of U.S. Provisional Application No. 60/643,614, filed Jan. 12, 2005.

STATEMENT REGARDING FEDERALLY SPONSORED RESEARCH OR DEVELOPMENT

This invention was made with government support under grant numbers R01 AI54540, AI26170, AI063537, and AI57158 awarded by the National Institutes of Health. The government has certain rights in the invention.

BACKGROUND OF THE INVENTION (1). Field of the Invention

The present invention generally relates to mutants of *Mycobacterium tuberculosis*. More particularly, the invention is directed to *M. tuberculosis* mutants that affect host cell apoptosis.

(2). Description of the Related Art

References

Abou-Zeid, C., Smith, I., Grange, J. M., Ratliff, T. L., Steele, J., and Rook, G. A. (1988) The secreted antigens of *Mycobacterium tuberculosis* and their relationship to those recognized by the available antibodies. *J Gen Microbiol* 134 (Pt 2): 531-538.

Alemán, M. et al. (2002) *Mycobacterium tuberculosis*-induced activation accelerates apoptosis in peripheral blood neutrophils from patients with active tuberculosis. *Am J Respir Cell Mol Biol* 27:583-592.

Andersen, P. (1994) The T cell response to secreted antigens of *Mycobacterium tuberculosis*. *Immunobiology* 191: 537-547.

Armstrong, J. A., and Hart, P. D. (1975) Phagosome-lysosome interactions in cultured macrophages infected with virulent tubercle bacilli. Reversal of the usua=1 nonfusion pattern and observations on bacterial survival. *J Exp Med* 142: 1-16.

Balcewicz-Sablinska, M. K., Keane, J., Kornfeld, H. & Remold, H. G. (1998) Pathogenic *Mycobacterium tuberculosis* evades apoptosis of host macrophages by release of TNF-R2, resulting in inactivation of TNF-alpha. *J Immunol* 161: 2636-41.

Bange, F. C., Collins, F. M. & Jacobs, W. R., Jr. (1999) Survival of mice infected with *Mycobacterium smegmatis* containing large DNA fragments from *Mycobacterium tuberculosis*. *Tuber Lung Dis* 79: 171-80.

Bardarov, S. et al. (2002) Specialized transduction: an efficient method for generating marked and unmarked targeted gene disruptions in *Mycobacterium tuberculosis, M. bovis* BCG and *M. smegmatis. Microbiology* 148: 3007-17.

Bermudez, L. E., and Goodman, J. (1996) *Mycobacterium tuberculosis* invades and replicates within type II alveolar cells. *Infect Immun* 64: 1400-1406.

Berthet, F. X., Lagranderie, M., Gounon, P., Laurent-Winter, C., Ensergueix, D., Chavarot, P., Thouron, F., Maranghi, E., Pelicic, V., Portnoi, D., Marchal, G., and Gicquel, B. (1998) Attenuation of virulence by disruption of the *Mycobacterium tuberculosis* erp gene. *Science* 282: 759-762.

Blanke, S. R. (2005) Micro-managing the executioner: pathogen targeting of mitochondria. *Trends Microbiol* 13: 64-71.

Braunstein, M., Griffin, T. I., Kriakov, J. I., Friedman, S. T., Grindley, N. D., and Jacobs, W. R., Jr. (2000) Identification of genes encoding exported *Mycobacterium tuberculosis* proteins using a Tn552'phoA in vitro transposition system. *J Bacteriol* 182: 2732-2740.

Braunstein, M. et al. (2003) SecA2 functions in the secretion of superoxide dismutase A and in the virulence of *Mycobacterium tuberculosis*. *Mol Microbiol* 48: 453-464.

Ciaramella, A. et al. (2000) Mycobacterial 19-kDa lipoprotein mediates *Mycobacterium tuberculosis*-induced apoptosis in monocytes/macrophages at early stages of infection. *Cell Death Differentiation* 7:1270-1272.

Carroll, J. D., Wallace, R. C., Keane, J., Remold, H. G., and Arbeit, R. D. (2000) Identification of *Mycobacterium avium* DNA sequences that encode exported proteins by using phoA gene fusions. *Tuber Lung Dis* 80: 117-130.

Clemens, D. L., and Horwitz, M. A. (1995) Characterization of the *Mycobacterium tuberculosis* phagosome and evidence that phagosomal maturation is inhibited. *J Exp Med* 181: 257-270.

Cole, S. T. et al. (1998) Deciphering the biology of *Mycobacterium tuberculosis* from the complete genome sequence. *Nature* 393: 537-44.

Corbett, E. L., Watt, C. J., Walker, N., Maher, D., Williams, B. G., Raviglione, M. C., and Dye, C. (2003) The growing burden of tuberculosis: global trends and interactions with the HIV epidemic. *Arch Intern Med* 163: 1009-1021.

Daffe, M., and Etienne, G. (1999) The capsule of *Mycobacterium tuberculosis* and its implications for pathogenicity. *Tuber Lung Dis* 79: 153-169.

Dannenberg, A. M., Jr. (1993) Immunopathogenesis of pulmonary tuberculosis. *Hosp Pract (Off Ed)* 28: 51-58.

Dao, D. N. et al. (2004) *Mycobacterium tuberculosis* lipomannan induces apoptosis and interleukin-12 production in macrophages. *Infect Immun* 72: 2067-74.

Duan, L., Gan, H., Arm, J., and Remold, H. G. (2001) Cytosolic phospholipase A2 participates with TNF-alpha in the induction of apoptosis of human macrophages infected with *Mycobacterium tuberculosis* H37Ra. *J Immunol* 166: 7469-7476.

Duan, L. et al. (2002) Critical role of mitochondrial damage in determining outcome of macrophage infection with *Mycobacterium tuberculosis*. *J Immunol* 169:5181-5187.

Duarte, R. et al. (1997) *Mycobacterium tuberculosis* induces apoptosis in δ/γ T lymphocytes from patients with advanced clinical forms of active tuberculosis. *Clin Diag Lab Immunol* 4:14-18.

Dye, C., Scheele, S., Dolin, P., Pathania, V. & Raviglione, M. C. Consensus statement. (1999) Global burden of tuberculosis: estimated incidence, prevalence, and mortality by country. WHO Global Surveillance and Monitoring Project. *JAMA* 282: 677-86.

Eddine, A. N. and Kaufmann, S. H. E. (2005) Improved protection by recombinant BCG. *Microbes and Infection* 7: 939-946.

Edwards, K. M., Cynamon, M. H., Voladri, R. K., Hager, C. C., DeStefano, M. S., Tham, K. T., Lakey, D. L., Bochan, M. R., and Kernodle, D. S. (2001) Iron-cofactored superoxide dismutase inhibits host responses to *Mycobacterium tuberculosis*. *Am J Respir Crit Care Med* 164: 2213-2219.

Fan, S., Wang, J. A., Yuan, R. Q., Rockwell, S., Andres, J., Zlatapolskiy, A., Goldberg, I. D., and Rosen, E. M. (1998)

Scatter factor protects epithelial and carcinoma cells against apoptosis induced by DNA-damaging agents. *Oncogene* 17: 131-141.

Finlay, B. B., and Falkow, S. (1997) Common themes in microbial pathogenicity revisited. *Microbiol Mol Biol Rev* 61: 136-169.

Fratazzi, C., Arbeit, R. D., Carini, C. & Remold, H. G. (1997) Programmed cell death of *Mycobacterium avium* serovar 4-infected human macrophages prevents the mycobacteria from spreading and induces mycobacterial growth inhibition by freshly added, uninfected macrophages. *J Immunol* 158: 4320-7.

Friedrich, T. & Bottcher, B. (2004) The gross structure of the respiratory complex I: a Lego System. *Biochim Biophys Acta* 1608: 1-9. Gao, L., and Abu Kwaik, Y. (2000) Hijacking of apoptotic pathways by bacterial pathogens. *Microbes Infect* 2: 1705-1719.

Gatfield, J., and Pieters, J. (2000) Essential role for cholesterol in entry of mycobacteria into macrophages. *Science* 288: 1647-1650.

Gil, D. P., Leon, L. G., Correa, L. I., Maya, J. R., Paris, S. C., Garcia, L. F., and Rojas, M. (2004) Differential induction of apoptosis and necrosis in monocytes from patients with tuberculosis and healthy control subjects. *J Infect Dis* 189: 2120-2128.

Grode, L. et al. (2005) Increased vaccine efficacy against tuberculosis of recombinant *Mycobacterium bovis* bacilli Calmette-Guérin mutants that secrete listeriolysin. *J Clin Invest* 118:2472-2479.

Hsu T, et al. (2003) *Proc Natl Acad Sci USA* 100:12420.

Hubbard, R. D., Flory, C. M., and Collins, F. M. (1992) Immunization of mice with mycobacterial culture filtrate proteins. *Clin Exp Immunol* 87: 94-98.

Johansen, K. A., Gill, R. E., and Vasil, M. L. (1996) Biochemical and molecular analysis of phospholipase C and phospholipase D activity in mycobacteria. *Infect Immun* 64: 3259-3266.

Keane, J., Balcewicz-Sablinska, M. K., Remold, H. G., Chupp, G. L., Meek, B. B., Fenton, M. J., and Kornfeld, H. (1997) Infection by *Mycobacterium tuberculosis* promotes human alveolar macrophage apoptosis. *Infect Immun* 65: 298-304.

Keane, J., Remold, H. G., and Kornfeld, H. (2000) Virulent *Mycobacterium tuberculosis* strains evade apoptosis of infected alveolar macrophages. *J Immunol* 164: 2016-2020.

Kornfeld, H. et al. (1999) The role of macrophage cell death in tuberculosis. *Cell Death Differentiation* 6:71-78.

Kramer, K., Harrington, E. O., Lu, Q., Bellas, R., Newton, J., Sheahan, K. L., and Rounds, S. (2003) Isoprenylcysteine carboxyl methyltransferase activity modulates endothelial cell apoptosis. *Mol Biol Cell* 14: 848-857.

Leemans, J. C., Juffermans, N. P., Florquin, S., van Rooijen, N., Vervoordeldonk, M. J., Verbon, A., van Deventer, S. J., and van der Poll, T. (2001) Depletion of alveolar macrophages exerts protective effects in pulmonary tuberculosis in mice. *J Immunol* 166: 4604-4611.

Lim, E. M., Rauzier, J., Timm, J., Torrea, G., Murray, A., Gicquel, B., and Portnoi, D. (1995) Identification of *Mycobacterium tuberculosis* DNA sequences encoding exported proteins by using phoA gene fusions. *J Bacteriol* 177: 59-65.

Lopez, M., Sly, L. M., Luu, Y., Young, D., Cooper, H., and Reiner, N. E. (2003) The 19-kDa *Mycobacterium tuberculosis* protein induces macrophage apoptosis through Toll-like receptor-2. *J Immunol* 170: 2409-2416.

Lyadova, I. V. et al. (2000) *J. Immunol.* 165:5921-5931.

Molloy, A., Laochumroonvorapong, P., and Kaplan, G. (1994) Apoptosis, but not necrosis, of infected monocytes is coupled with killing of intracellular *bacillus* Calmette-Guerin. *J Exp Med* 180: 1499-1509.

Moore, K. J., and Matlashewski, G. (1994) Intracellular infection by *Leishmania donovani* inhibits macrophage apoptosis. *J Immunol* 152: 2930-2937.

Nagai, S., Wiker, H. G., Harboe, M., and Kinomoto, M. (1991) Isolation and partial characterization of major protein antigens in the culture fluid of *Mycobacterium tuberculosis. Infect Immun* 59: 372-382.

Nash, P. D., Purner, M. B., Leon, R. P., Clarke, P., Duke, R. C., and Curiel, T. J. (1998) *Toxoplasma gondii*-infected cells are resistant to multiple inducers of apoptosis. *J Immunol* 160: 1824-1830.

Nguyen, L. & Pieters, J. (2005) The Trojan horse: survival tactics of pathogenic mycobacteria in macrophages. *Trends Cell Biol* 15: 269-76.

North, R. J. (1995) *Mycobacterium tuberculosis* is strikingly more virulent for mice when given via the respiratory than via the intravenous route. *J Infect Dis* 172: 1550-1553.

Noss, E. H., Pai, R. K., Sellati, T. J., Radolf, J. D., Belisle, J., Golenbock, D. T., Boom, W. H., and Harding, C. V. (2001) Toll-like receptor 2-dependent inhibition of macrophage class II MHC expression and antigen processing by 19-kDa lipoprotein of *Mycobacterium tuberculosis. J Immunol* 167: 910-918.

Oddo, M., Renno, T., Attinger, A., Bakker, T., MacDonald, H. R., and Meylan, P. R. (1998) Fas ligand-induced apoptosis of infected human macrophages reduces the viability of intracellular *Mycobacterium tuberculosis. J Immunol* 160: 5448-5454.

Orme, I. M. (2003) The mouse as a useful model of tuberculosis. *Tuberculosis* (*Edinb*) 83: 112-115.

Pal, P. G., and Horwitz, M. A. (1992) Immunization with extracellular proteins of *Mycobacterium tuberculosis* induces cell-mediated immune responses and substantial protective immunity in a guinea pig model of pulmonary tuberculosis. *Infect Immun* 60: 4781-4792.

Pan, H. et al. (2005) Ipr1 gene mediates innate immunity to tuberculosis. Nature 434: 767-72.

Portales-Pérez, D. P. et al. (2002) Comparative and prospective study of different immune parameters in healthy subjects at risk for tuberculosis and in tuberculosis patients. *Clin Diag Lab Immunol* 9:299-307.

Ricci, J. E. et al. (2004) Disruption of mitochondrial function during apoptosis is mediated by caspase cleavage of the p75 subunit of complex I of the electron transport chain. *Cell* 117: 773-86.

Riendeau, C. J., and Kornfeld, H. (2003) THP-1 cell apoptosis in response to Mycobacterial infection. *Infect Immun* 71: 254-259.

Roberts, A. D., Sonnenberg, M. G., Ordway, D. J., Furney, S. K., Brennan, P. J., Belisle, J. T., and Orme, L M. (1995) Characteristics of protective immunity engendered by vaccination of mice with purified culture filtrate protein antigens of *Mycobacterium tuberculosis. Immunology* 85: 502-508.

Rojas, M., Barrera, L. F., Puzo, G., and Garcia, L. F. (1997) Differential induction of apoptosis by virulent *Mycobacterium tuberculosis* in resistant and susceptible murine macrophages: role of nitric oxide and mycobacterial products. *J Immunol* 159: 1352-1361.

Rojas, M., Olivier, M., Gros, P., Barrera, L. F., and Garcia, L. F. (1999) TNF-alpha and IL-10 modulate the induction of apoptosis by virulent *Mycobacterium tuberculosis* in murine macrophages. *J Immunol* 162: 6122-6131.

Rojas, M., Garcia, L. F., Nigou, J., Puzo, G., and Olivier, M. (2000) Mannosylated lipoarabinomannan antagonizes Mycobacterium tuberculosis-induced macrophage apoptosis by altering Ca+2-dependent cell signaling. *J Infect Dis* 182: 240-251.

Rolls, M. M., Stein, P. A., Taylor, S. S., Ha, E., McKeon, F., and Rapoport, T. A. (1999) A visual screen of a GFP-fusion library identifies a new type of nuclear envelope membrane protein. *J Cell Biol* 146: 29-44.

Sambandamurthy, V. K., Wang, X., Chen, B., Russell, R. G., Derrick, S., Collins, F. M., Morris, S. L., and Jacobs, W. R., Jr. (2002) A pantothenate auxotroph of *Mycobacterium tuberculosis* is highly attenuated and protects mice against tuberculosis. *Nat Med* 8: 1171-1174.

Sassetti, C. M. & Rubin, E. J. (2003) Genetic requirements for mycobacterial survival during infection. *Proc Natl Acad Sci USA* 100: 12989-94.

Schnappinger, D. et al. (2003) Transcriptional Adaptation of *Mycobacterium tuberculosis* within Macrophages: Insights into the Phagosomal Environment. *J Exp Med* 198: 693-704.

Scanga, C. A., Mohan, V. P., Tanaka, K., Alland, D., Flynn, J. L., and Chan, J. (2001) The inducible nitric oxide synthase locus confers protection against aerogenic challenge of both clinical and laboratory strains of *Mycobacterium tuberculosis* in mice. *Infect Immun* 69: 7711-7717.

Schaible, U. E., Winau, F., Sieling, P. A., Fischer, K., Collins, H. L., Hagens, K., Modlin, R. L., Brinkman, V., and Kaufmann, S. H. (2003) Apoptosis facilitates antigen presentation to T lymphocytes through MHC-I and CD1 in tuberculosis. *Nat Med* 9: 1039-1046.

Schrijvers D M, Martinet W, De Meyer G R, Andries L, Herman A G, Kockx M M. (2004) *J Immunol Meth* 287: 101-8.

Schwebach, J. R., Chen, B., Glatman-Freedman, A., Casadevall, A., McKinney, J. D., Harb, J. L., McGuire, P. J., Barkley, W. E., Bloom, B. R., and Jacobs, W. R., Jr. (2002) Infection of mice with aerosolized *Mycobacterium tuberculosis*: use of a nose-only apparatus for delivery of low doses of inocula and design of an ultrasafe facility. *Appl Environ Microbial* 68: 4646-4649.

Sly, L. M., Hingley-Wilson, S. M., Reiner, N. E. & McMaster, W. R. (2003) Survival of *Mycobacterium tuberculosis* in host macrophages involves resistance to apoptosis dependent upon induction of antiapoptotic Bcl-2 family member Mc1-1. *J Immunol* 170: 430-7.

Snapper, S. B., Melton, R. E., Mustafa, S., Kieser, T. & Jacobs, W. R., Jr. (1990) Isolation and characterization of efficient plasmid transformation mutants of *Mycobacterium smegmatis*. *Mod Microbiol* 4: 1911-9.

Spira, A. et al. (2003) Apoptosis genes in human alveolar macrophages infected with virulent or attenuated *Mycobacterium tuberculosis*. *Am J Respir Cell Mol Biol* 29: 545-551.

Stenger, S., Niazi, K. R., and Modlin, R. L. (1998) Downregulation of CD1 on antigen-presenting cells by infection with *Mycobacterium tuberculosis*. *J Immunol* 161: 3582-3588.

Stover, C. K. et al. (1991) New use of BCG for recombinant vaccines. *Nature* 351: 456-60.

Teodoro, J. G., and Branton, P. E. (1997) Regulation of apoptosis by viral gene products. *J Virol* 71: 1739-1746.

VanHeyningen, T. K., Collins, H. L., and Russell, D. G. (1997) IL-6 produced by macrophages infected with *Mycobacterium* species suppresses T cell responses. *J Immunol* 158: 330-337.

Vaux, D. L., and Strasser, A. (1996) The molecular biology of apoptosis. *Proc Natl Acad Sci USA* 93: 2239-2244.

Wadee, A. A., Kuschke, R. H., and Dooms, T. G. (1995) The inhibitory effects of *Mycobacterium tuberculosis* on MHC class II expression by monocytes activated with riminophenazines and phagocyte stimulants. *Clin Exp Immunol* 100: 434-439.

Ylid, U., and Wick, M. J. (2000) *Salmonella*-induced apoptosis of infected macrophages results in presentation of a bacteria-encoded antigen after uptake by bystander dendritic cells. *J Exp Med* 191: 613-624.

Zhang, Y., Heym, B., Allen, B., Young, D., and Cole, S. (1992) The catalase-peroxidase gene and isoniazid resistance of *Mycobacterium tuberculosis*. *Nature* 358: 591-593.

Zhang-Barber, L. et al. (1998) Protection of chickens against experimental fowl typhoid using a nuoG mutant of *Salmonella* serotype Gallinarum. *Vaccine* 16:899-903.

*Mycobacterium tuberculosis*, the etiological agent of tuberculosis, is responsible for more deaths each year than any other single pathogen (Corbett et al., 2003). The emergence of drug resistant strains of *M. tuberculosis* and HIV co-infection has contributed to the worsening impact of this disease. The pathogen exhibits extraordinary capacity to subvert and resist bactericidal responses of its infected host. *M. tuberculosis* virulence has been associated with its initial survival within macrophages by evading the host response in many different ways. The tubercle bacilli reside in endocytic vacuoles (Armstrong and Hart, 1975; Clemens and Horwitz, 1995), which fail to fuse to lysosomes due to *M. tuberculosis* mediated retention of a host protein TACO on the membrane of these vacuoles (Gatfield and Pieters, 2000). Similarly, *M. tuberculosis* can downregulate the expression of MHC-II (Noss et al., 2001) and costimulatory molecules (Stenger et al., 1998; Wadee et al., 1995), modulate the cytokine environment in its vicinity (VanHeyningen et al., 1997) and inhibit apoptosis of the host cell (Keane et al., 1997). Although *M. tuberculosis* evades many host responses to maintain itself in a habitable environment, the bacterial effectors mediating such effects need to be delineated. On invading the host cell, a capsule-like structure is formed outside the membrane and the cell wall of the tubercle bacilli (Daffe and Etienne, 1999), and this interface contains important surface proteins involved in the pathogenesis and immune responses to TB, The secreted and cell envelope associated proteins, located at the interface between the mycobacterium and its eukaryotic host mediate host-pathogen interactions. Therefore, such proteins are candidate virulence factors and warrants further study (Finlay and Falkow, 1997).

The exported and secreted proteins of *M. tuberculosis* have been proposed to play a role in virulence and indeed contribute to the immune responses to TB (Abou-Zeid et al., 1988; Johansen et al., 1996; Nagai et al., 1991; Zhang et al., 1992). Research on several bacterial pathogens has revealed that the majority of virulence factors are secreted (Finlay and Falkow, 1997). Studies have also emphasized the importance of the secreted and exported proteins of *M. tuberculosis* in the generation of a protective immune response. The most striking demonstration of this property comes from experiments in which mice or guinea pigs were immunized with extracellular proteins and significant protective immunity elicited (Andersen, 1994; Hubbard et al., 1992; Pal and Horwitz, 1992; Roberts et al., 1995). Recently, the exported ERP (exported repetitive protein) protein was shown to contribute to the virulence of *M. tuberculosis* (Berthet et al., 1998). Likewise, superoxide dismutase (SOD), a culture filtrate component was shown to be associated with virulence by interfering with host apoptosis (Edwards et al., 2001). While many secreted proteins have been studied, the study of the cell surface proteins is still lacking due to technological constraints in isolating samples of membrane proteins.

Host cell apoptosis has been implicated in *Mycobacterium* spp. virulence and protective immunity (e.g., Alemán et al., 2002; Balcewicz-Sablinska et al., 1998; Ciaramella et al., 2000; Duan et al., 2001, 2002; Duarte et al., 1997; Eddine et al., 2005; Grode et al., 2005; Keane et al., 2000; Kornfeld et al., 1999; López et al., 2003; Protales-Pérez et al., 2002; Sly et al., 2003; Spira et al., 2003). However, there is need for more information on *Mycobacterium* host genes that affect host cell apoptosis. The present invention addresses that need.

SUMMARY OF THE INVENTION

The present invention identifies mycobacterial genes that encode proteins that inhibit host apoptosis. *Mycobacterium* mutants that do not express the proteins are useful for inducing immunity to virulent mycobacteria.

Thus, the present invention is directed to recombinant mycobacteria having a mutation in an nlaA gene. The mutation in these mycobacteria increases the ability of the mycobacteria to induce apoptosis of a mammalian macrophage infected by the mycobacteria.

The invention is also directed to recombinant mycobacteria having a mutation in a nuoG gene. The mutation in these mycobacteria also increases the ability of the mycobacteria to induce apoptosis of a mammalian macrophage infected by the mycobacteria.

The present invention is additionally directed to isolated and purified nlaA proteins from a mycobacterium. These nlaA proteins have an amino acid sequence at least 85% identical to SEQ ID NO:1. These nlaA proteins prevent the mycobacterium from inducing apoptosis in a mammalian macrophage.

The invention is further directed to isolated and purified nuoG proteins from a mycobacterium. These nuoG proteins have an amino acid sequence at least 85% identical to SEQ ID NO:3. These nuoG proteins also prevent the mycobacterium from inducing apoptosis in a mammalian macrophage.

The present invention is also directed to isolated and purified nucleic acids comprising a recombinant nlaA gene having a nucleotide sequence at least 85% identical to SEQ ID NO:2.

Additionally, the invention is directed to isolated and purified nucleic acids comprising a recombinant nuoG gene having a nucleotide sequence at least 85% identical to SEQ ID NO:4.

The current invention is further directed to methods of inducing an immune response in a mammal. The methods comprise inoculating the mammal with any of the above-described mycobacteria.

The invention is additionally directed to methods of making a recombinant mycobacterium. The methods comprise eliminating expression of the nlaA gene in the mycobacterium.

The present invention is further directed to additional methods of making a recombinant mycobacterium. The methods comprise eliminating expression of the nuoG gene in the mycobacterium.

BRIEF DESCRIPTION OF THE DRAWINGS

Figure 5:
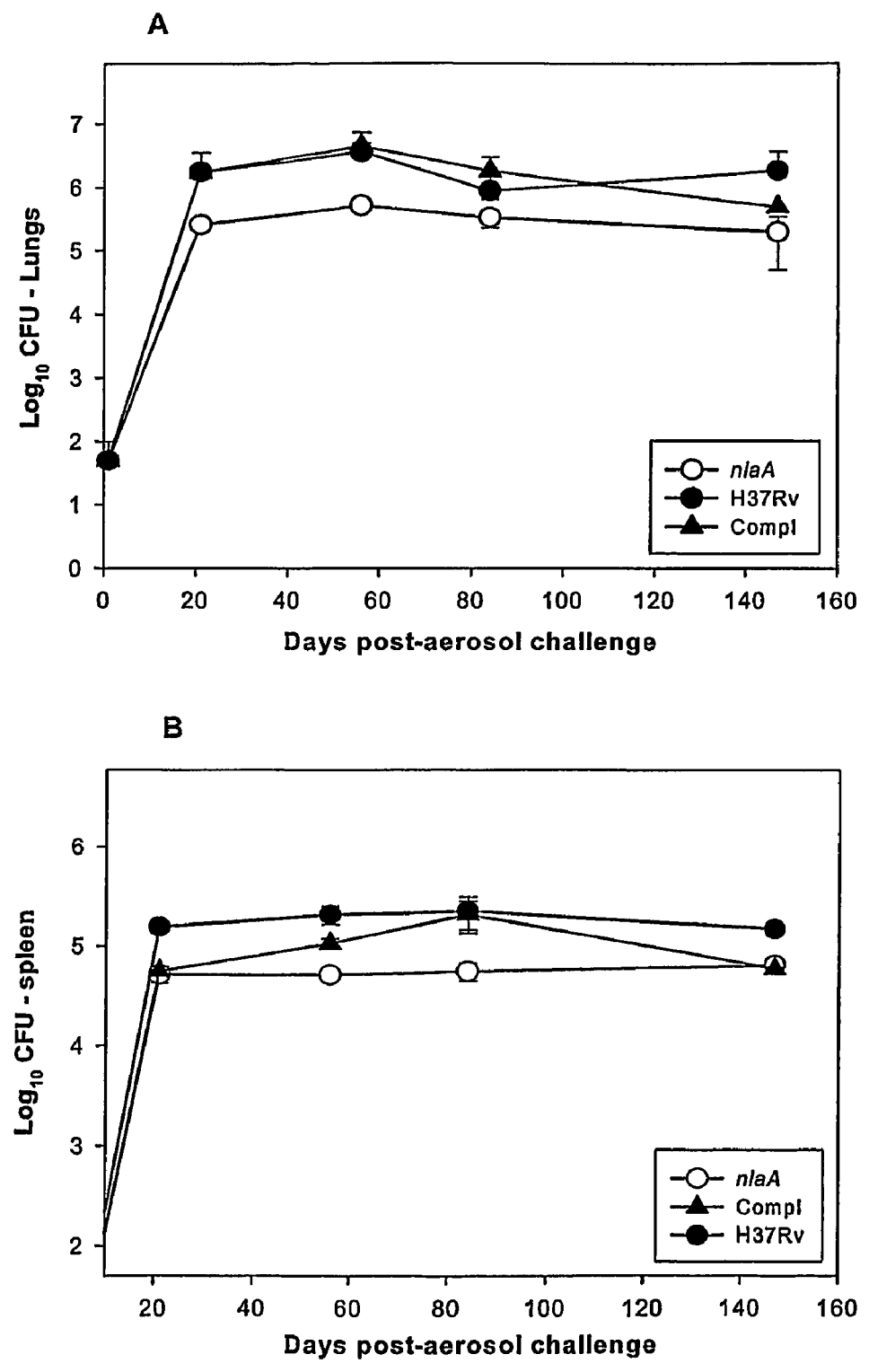

FIG. 5 is graphs showing the deletion mutant displays growth defects in the organs of infected mice. Total CFU counts of wild-type *M. tuberculosis* H37Rv (●), *M. tuberculosis* ΔnlaA (◇) and the complemented strain (▲) at various time points in lungs (A) and spleen (B) of mice infected via aerosol route. Data are expressed as log 10 value of mean number of bacteria+/−standard deviation recovered from each mouse. Groups of four mice were evaluated at each time point. * $p<0.0001$  $p<0.001$ *$p<0.01$ compared to wild-type H37Rv.

DETAILED DESCRIPTION OF THE INVENTION

Figure 1:
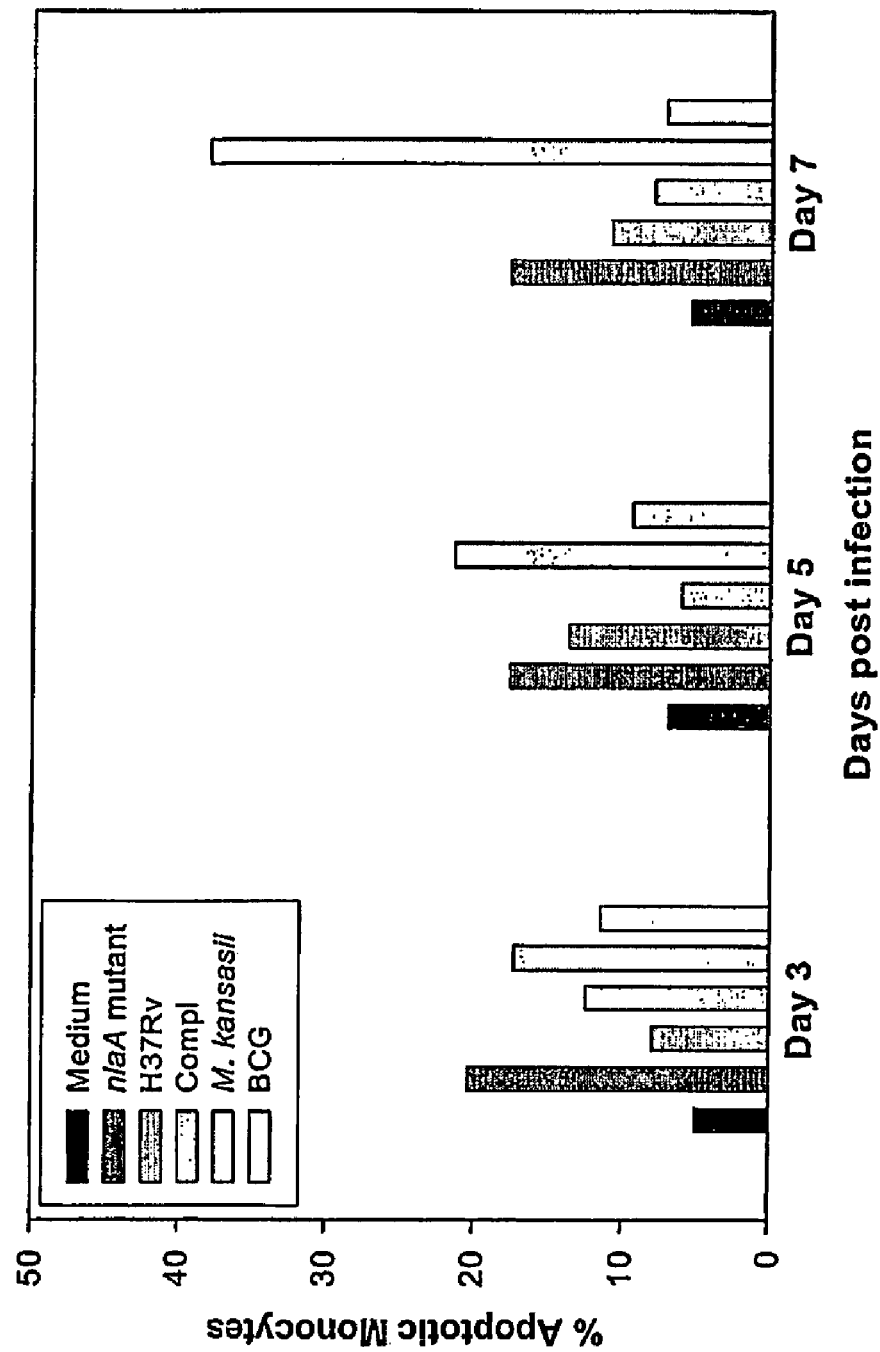
FIG. 1 is a graph showing that a deletion mutant induces more apoptosis than wild-type. Nuclear fragmentation was assayed by TUNEL followed by flow cytometric analysis from THP1 cells after 3, 5 and 7 days of infection with *M. tuberculosis* H37Rv, *M. tuberculosis* ΔnlaA, *M. bovis* BCG, *M. kansasii* and the complemented strain at an infectious dose of 10 bacilli per macrophage (MOI). Results are representative of three independent experiments done in triplicates.
Figure 2:
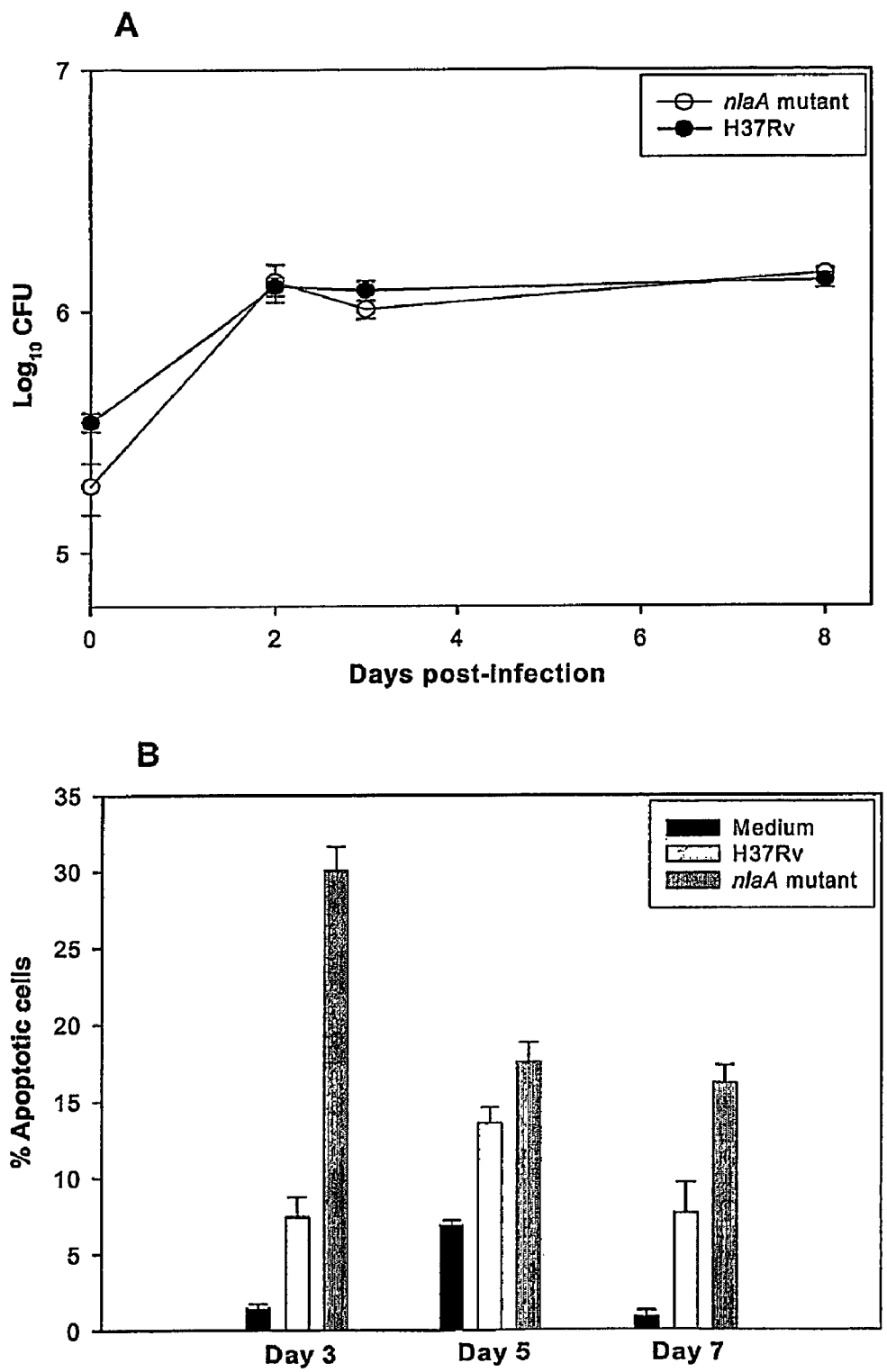
FIG. 2 is graphs showing that the deletion mutant induces more apoptosis than wild-type which is not a result of limited growth in vitro. A) Growth of wild-type *M. tuberculosis* H37Rv and *M. tuberculosis* ΔnlaA in THP-1 macrophages at 3, 5 and 8 days post infection. B) Nuclear fragmentation assayed by TUNEL followed by flow cytometric analysis from THP1 cells after 3, 5 and 7 days of infection with *M. tuberculosis* H37Rv, *M. tuberculosis* ΔnlaA at an infectious dose of 10 bacilli per macrophage (MOI). Results are representative of three independent experiments done in triplicates.
Figure 3:
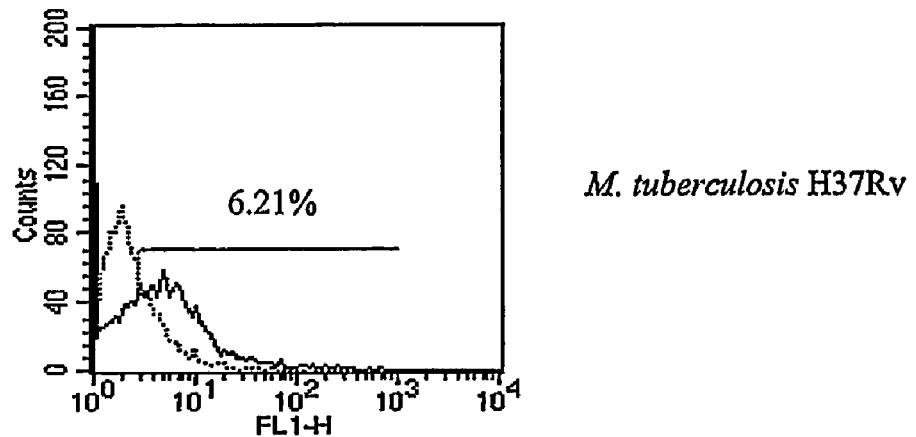
FIG. 3 is graphs showing the deletion mutant induces more apoptosis than wild-type which is not a result of limited growth in vitro. Representative flow cytometric analysis of TUNEL stained apoptotic THP-1 cells following 3 days of infection with *M. tuberculosis* H37Rv, nlaA mutant and the complemented strain. Dotted line represent levels of apoptosis in the absence of any infection. Solid lines represent the levels of apoptosis under infection conditions.
Figure 3:
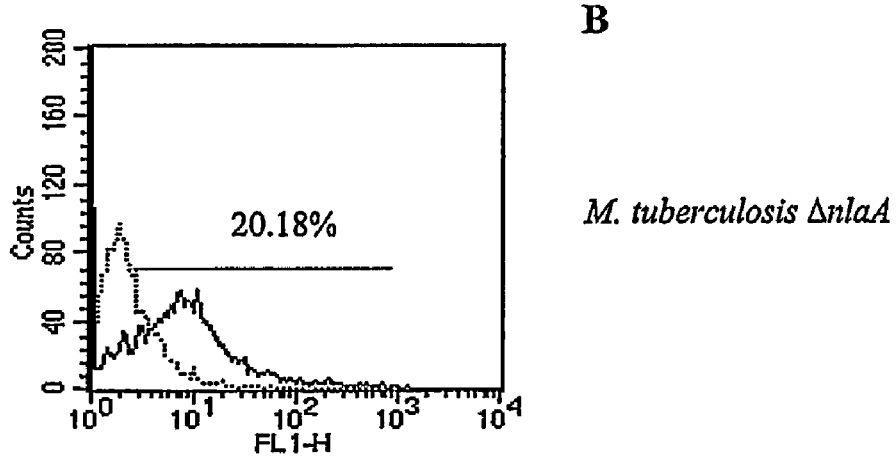
Figure 3:
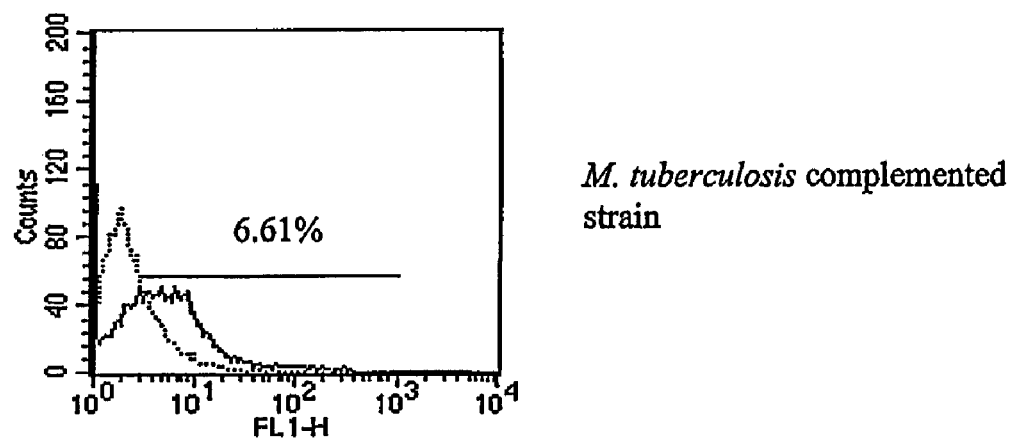
Figure 4:
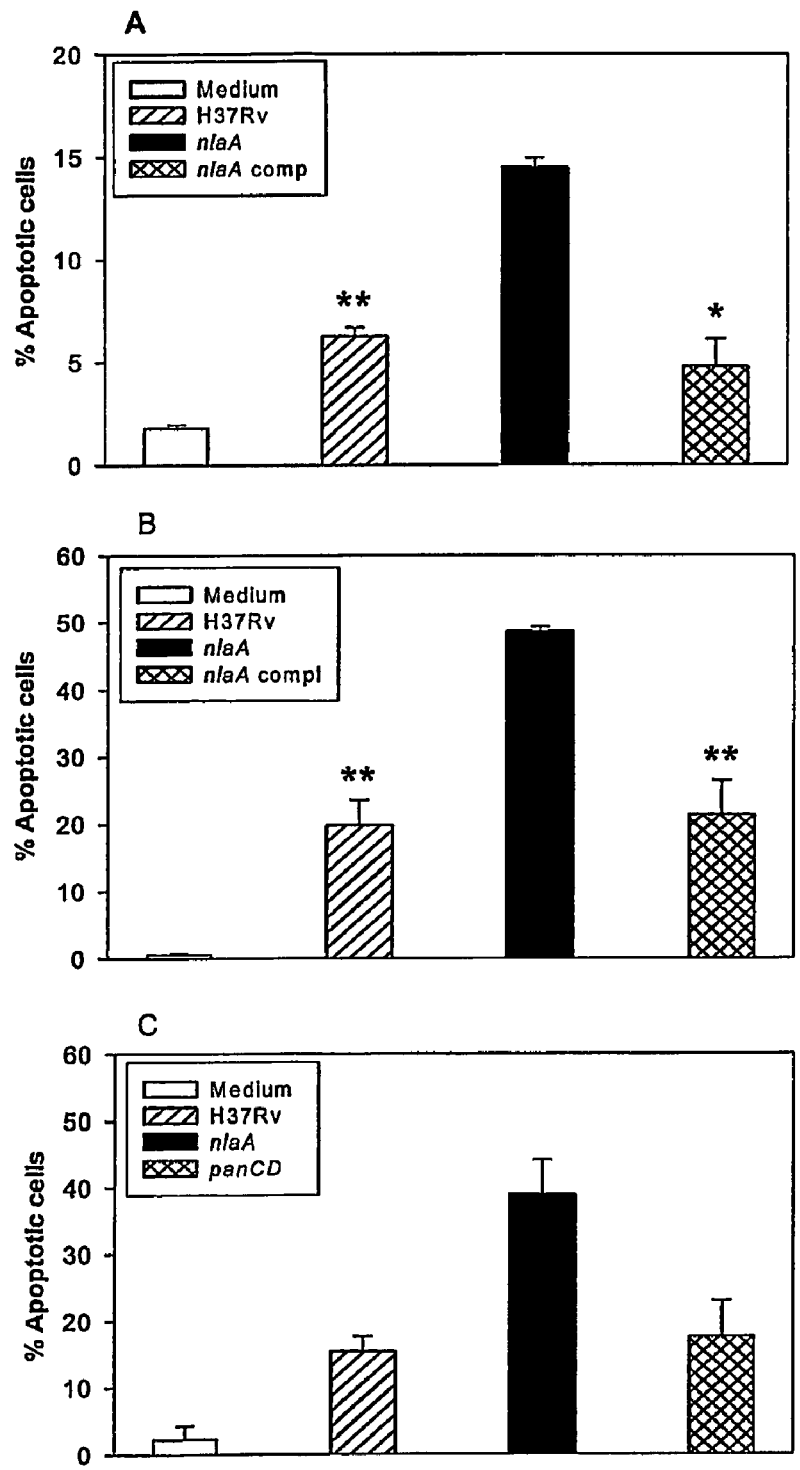
FIG. 4 is graphs showing the deletion mutant induces more apoptosis than wild-type that is specific to the nlaA gene. Nuclear fragmentation assayed by TUNEL followed by flow cytometric analysis from THP1 cells after 3 of infection with *M. tuberculosis* H37Rv, *M. tuberculosis* ΔnlaA and the complemented strain at an MOI of 5 A) or B) MOI of 10 or C) *M. tuberculosis* H37Rv, *M. tuberculosis* ΔnlaA, *M. tuberculosis* ΔpanCD at an infectious dose of 10 bacilli per macrophage. Results are representative of three independent experiments done in triplicates. ** $p<0.0001$ *$p<0.002$ compared to wild-type H37Rv.

The inventors have identified and characterized mycobacterium genes that prevent apoptosis of a mammalian cell infected by the mycobacterium. This finding enables and makes useful various compositions and methods relating to the use of recombinant mycobacteria deleted in the gene. Such mycobacteria are useful, for example, as live mycobacterial vaccines because the increased apoptosis of infected cells, particularly macrophages, allows for better presentation of antigens and induction of immunity. See Examples below.

Thus, the present invention is directed to recombinant mycobacteria having a mutation in an nlaA gene. The mutation in these mycobacteria increases the ability of the mycobacteria to induce apoptosis of a mammalian macrophage infected by the mycobacteria.

The amino acid and cDNA sequences for one form of the nlaA gene, from an *M. tuberculosis*, is provided herein as SEQ ID NO:1 and SEQ ID NO:2, respectively. However, these embodiments are not limited to the protein and gene provided as SEQ ID NO:1 and SEQ ID NO:2, since other mycobacteria would be expected to have forms of nlaA that have a different amino acid and protein sequence. The present invention would therefore encompass any nlaA protein and gene from a mycobacterium, which would be expected to be at least about 85%, or at least 95%, or at least 99% identical to SEQ ID NO:1 and SEQ ID NO:2, respectively. Any such form of nlaA could be identified and isolated without undue experimentation by a skilled artisan. Thus, the nlaA gene without the mutation preferably encodes a protein that is at least about 85% homologous to SEQ ID NO:1; more preferably, the nlaA gene without the mutation encodes a protein that is at least about 99% homologous to SEQ ID NO:1. Most preferably, the nlaA gene without the mutation encodes a protein having the amino acid sequence of SEQ 113 NO:1.

Since these mycobacteria are designed to be used in vivo, it is preferred that the mycobacteria is avirulent or rendered so, e.g., by selecting for avirulent strains or by engineering the mycobacteria to have a mutation or mutations that can fulfill that purpose. Many such mutations are known in the art, for example mutations that render the mycobacterium auxotrophic, e.g., a pan mutation or a Lys mutation, or mutations eliminating pathogenicity genes such as an RD1 deletion, as is known in the art. It is also preferred that the mycobacterium utilized for this invention can colonize the host, in order for the mycobacterium to provide a long term antigenic stimulus to the host, thus establishing a strong immune response. Non-limiting examples of useful mycobacteria are *Mycobacterium smegmatis*, *Mycobacterium bovis*-BCG, *Mycobacterium avium*, *Mycobacterium phlei*, *Mycobacterium fortuitum*, *Mycobacterium lufu*, *Mycobacterium paratuberculosis*, *Mycobacterium habana*, *Mycobacterium microti*, *Mycobacterium scrofulacium*, *Mycobacterium intracellulare*, *Mycobacterium tuberculosis*, and any genetic variant thereof. In some preferred embodiments the mycobacterium is a *Mycobacterium tuberculosis*, since the nlaA gene, and the ΔnlaA mutation, is characterized herein in *M. tuberculosis*. Another particularly useful mycobacterial strain to incorporate a ΔnlaA mutation is *M. bovis* BCG.

Preferably, the mycobacterium further comprises a recombinant gene operably linked to a promoter that directs expression of the gene when the mycobacterium infects a mammalian cell. Preferably, the gene encodes an antigen, for example to a neoplasm, tumor or cancer, or to a human pathogen, to take advantage of the increased immunogenicity to the antigen as a result of the ΔnlaA mutation. Examples of pathogens (e.g., human pathogens) where antigens useful in these mycobacteria include viruses (e.g., HIV, hepatitis C virus, herpes virus, influenza, smallpox, diphtheria, tetanus, measles, mumps, rabies, poliovirus etc), bacteria (e.g., pathogenic mycobacteria, *Salmonella* sp., etc.), and eukaryotic parasites (e.g., malaria, *Leishmania*, etc.).

The invention is also directed to recombinant mycobacteria having a mutation in a nuoG gene. The mutation in these mycobacteria also increases the ability of the mycobacteria to induce apoptosis of a mammalian macrophage infected by the mycobacteria. See Example 2.

The amino acid and cDNA sequences for one form of the nuoG gene, from an *M. tuberculosis*, is provided herein as SEQ ID NO:3 and SEQ ID NO:4, respectively. However, these embodiments are not limited to the protein and gene provided as SEQ ID NO:3 and SEQ ID NO:4, since other mycobacteria would be expected to have forms of nuoG that have a different amino acid and protein sequence. The present invention would therefore encompass any nuoG protein and gene from a mycobacterium, which would be expected to be at least about 85%, or at least 95%, or at least 99% identical to SEQ II) NO:3 and SEQ ID NO:4, respectively. Any such form of nuoG could be identified and isolated without undue experimentation by a skilled artisan. Thus, the nuoG gene without the mutation preferably encodes a protein that is at least about 85% homologous to SEQ ID NO:3; more preferably, the nlaA gene without the mutation encodes a protein that is at least about 99% homologous to SEQ ID NO:3. Most preferably, the nuoG gene without the mutation encodes a protein having the amino acid sequence of SEQ ID NO:3.

Since these mycobacteria are designed to be used in vivo, it is preferred that the mycobacteria is avirulent or rendered so, e.g., by selecting for avirulent strains or by engineering the mycobacteria to have a mutation or mutations that can fulfill that purpose. Many such mutations are known in the art, for example mutations that render the mycobacterium auxotrophic, e.g., a pan mutation or a Lys mutation, or mutations eliminating pathogenicity genes such as an RD1 deletion, as is known in the art. It is also preferred that the mycobacterium utilized for this invention can colonize the host, in order for the mycobacterium to provide a long term antigenic stimulus to the host, thus establishing a strong immune response. Non-limiting examples of useful mycobacteria are *Mycobacterium smegmatis, Mycobacterium bovis*-BCG, *Mycobacterium avium, Mycobacterium phlei, Mycobacterium fortuitum, Mycobacterium lufu, Mycobacterium paratuberculosis, Mycobacterium habana, Mycobacterium microti, Mycobacterium scrofulacium, Mycobacterium intracellulare, Mycobacterium tuberculosis*, and any genetic variant thereof. In some preferred embodiments the mycobacterium is a *Mycobacterium tuberculosis*, since the nuoG gene, and the ΔnuoG mutation, is characterized herein in *M. tuberculosis*. Another particularly useful mycobacterial strain to incorporate a ΔnuoG mutation is *M. bovis* BCG.

Preferably, the mycobacteria further comprises a recombinant gene operably linked to a promoter that directs expression of the gene when the mycobacterium infects a mammalian cell. Preferably, the gene encodes an antigen, for example to a neoplasm, tumor or cancer, or to a human pathogen, to take advantage of the increased immunogenicity to the antigen as a result of the ΔnlaA or ΔnuoG mutation. Examples of pathogens where antigens useful in these mycobacteria include viruses, bacteria, and eukaryotic parasites.

The present invention is additionally directed to isolated and purified nlaA proteins from a mycobacterium. These nlaA proteins have an amino acid sequence at least 85% identical to SEQ ID NO:1. These nlaA proteins prevent the mycobacterium from inducing apoptosis in a mammalian macrophage. The nlaA protein of these embodiments could be from any mycobacteria. Any mycobacterial protein having at least 85% identity to SEQ ID NO:1 would be expected to be an nlaA protein and would be expected to prevent apoptosis in a mammalian cell infected by a mycobacterium expressing that nlaA protein. Preferably, the amino acid sequence is at least 95% identical to SEQ ID NO:1; more preferably 99% identical to SEQ ID NO:1. In the most preferred embodiments, the amino acid sequence of the isolated protein is SEQ ID NO:1. Preferably, the nlaA protein was expressed recombinantly.

The invention is further directed to isolated and purified nuoG proteins from a mycobacterium. These nuoG proteins have an amino acid sequence at least 85% identical to SEQ ID NO:3. These nuoG proteins also prevent the mycobacterium from inducing apoptosis in a mammalian macrophage. The nuoG protein of these embodiments could be from any mycobacteria. Any mycobacterial protein having at least 85% identity to SEQ ID NO:3 would be expected to be an nuoG protein and would be expected to prevent apoptosis in a mammalian cell infected by a mycobacterium expressing that nlaA protein. Preferably, the amino acid sequence is at least 95% identical to SEQ ID NO:3; more preferably 99% identical to SEQ ID NO:3. In the most preferred embodiments, the amino acid sequence of the isolated protein is SEQ ID NO:3. Preferably, the nuoG protein was expressed recombinantly.

The present invention is also directed to isolated and purified nucleic acids comprising a recombinant nlaA gene having a nucleotide sequence at least 85% identical to SEQ ID NO:2.

Useful manipulations of the nlaA gene are provided in Example 1. In preferred embodiments, the nucleotide sequence is at least 95% identical to SEQ ID NO:2; in more preferred embodiments, the nucleotide sequence is at least 99% identical to SEQ ID NO:2; in the most preferred embodiments, the nucleotide sequence is SEQ ID NO:2.

Preferably, the nucleic acid is a vector capable of replication and/or expression of the nlaA protein encoded by the recombinant nlaA gene when transfected into a mycobacterium.

Additionally, the invention is directed to isolated and purified nucleic acids comprising a recombinant nuoG gene having a nucleotide sequence at least 85% identical to SEQ ID NO:4.

Useful manipulations of the nuoG gene are provided in Example 2. In preferred embodiments, the nucleotide sequence is at least 95% identical to SEQ ID NO:4; in more preferred embodiments, the nucleotide sequence is at least 99% identical to SEQ ID NO:4; in the most preferred embodiments, the nucleotide sequence is SEQ ID NO:4.

Preferably, the nucleic acid is a vector capable of replication and/or expression of the nlaA protein encoded by the recombinant nuoG gene when transfected into a mycobacterium.

The current invention is further directed to methods of inducing an immune response in a mammal. The methods comprise inoculating the mammal with any of the above-described mycobacteria. Preferably, the mycobacteria comprises a mutation in an nlaA gene or an nuoG gene, where the mutation increases the ability of the mycobacteria to induce apoptosis of a mammalian macrophage infected by the mycobacteria.

The mycobacteria utilized in these methods can also comprise a recombinant gene operably linked to a promoter that directs expression of the gene when the mycobacterium infects a mammalian cell. Preferably, the gene encodes an antigen, for example to a neoplasm, tumor or cancer, or to a human pathogen, to take advantage of the increased immunogenicity to the antigen as a result of the ΔnlaA or ΔnuoG mutation. Examples of pathogens where antigens useful in these mycobacteria include viruses, bacteria, and eukaryotic parasites.

Preferably, the mycobacteria used in these methods is an *M. tuberculosis* or an *M. bovis*. Also preferably, the inoculation given in as part of these methods gives the mammal increased immunity to a virulent *M. tuberculosis*.

The invention is additionally directed to methods of making a recombinant mycobacterium. The methods comprise eliminating expression of the nlaA gene in the mycobacterium. In preferred embodiments, expression of the nlaA gene is eliminated by specialized transduction, as is known in the art. A second gene can also be eliminated in these mycobacterium, wherein the mycobacterium exhibits attenuated virulence in a mammal when compared to the same mycobacterium expressing the second gene. A preferred second genes here is a portion of an RD1 region, or a gene controlling production of a vitamin or an amino acid. Other preferred second genes that can usefully be eliminated here are those where eliminating expression of the second gene increases the ability of the mycobacterium to induce apoptosis of a mammalian macrophage infected by the mycobacterium.

These embodiments can be utilized with any species of mycobacterium. Preferred are avirulent species, or attenuated variants of a virulent species (e.g., *M. tuberculosis*, with, e.g., an RD1 or pan mutation). Nonlimiting examples of useful mycobacteria for this purpose are *Mycobacterium smegmatis, Mycobacterium bovis*-BCG, *Mycobacterium avium, Mycobacterium phlei, Mycobacterium fortuitum, Mycobacterium lufu, Mycobacterium paratuberculosis, Mycobacterium habana, Mycobacterium microti, Mycobacterium scrofulaceum, Mycobacterium intracellulare, Mycobacterium tuberculosis*, or any genetic variant thereof.

Analogous to previous embodiments, the mycobacterium preferably further comprises a recombinant gene operably linked to a promoter that directs expression of the gene when the mycobacterium infects a mammalian cell. The recombinant gene in these embodiments preferably encodes an antigen of a cancer or a human pathogen, such as a virus, bacterium, or eukaryotic parasite, as discussed above.

The present invention is further directed to additional methods of making a recombinant mycobacterium. The methods comprise eliminating expression of the nuoG gene in the mycobacterium. In preferred embodiments, expression of the nuoG gene is eliminated by specialized transduction. A second gene can also be eliminated in these mycobacterium, wherein the mycobacterium exhibits attenuated virulence in a mammal when compared to the same mycobacterium expressing the second gene. A preferred second genes here is a portion of an RD1 region, or a gene controlling production of a vitamin or an amino acid. Other preferred second genes that can usefully be eliminated here are those where eliminating expression of the second gene increases the ability of the mycobacterium to induce apoptosis of a mammalian macrophage infected by the mycobacterium.

These embodiments can be utilized with any species of mycobacterium. Preferred are avirulent species, or attenuated variants of a virulent species (e.g., *M. tuberculosis*, with, e.g., an RD1 or pan mutation). Nonlimiting examples of useful mycobacteria for this purpose are *Mycobacterium smegmatis, Mycobacterium bovis*-BCG, *Mycobacterium avium, Mycobacterium phlei, Mycobacterium fortuitum, Mycobacterium lufu, Mycobacterium paratuberculosis, Mycobacterium habana, Mycobacterium microti, Mycobacterium scrofulaceum, Mycobacterium intracellulare, Mycobacterium tuberculosis*, or any genetic variant thereof.

Analogous to previous embodiments, the mycobacterium preferably further comprises a recombinant gene operably linked to a promoter that directs expression of the gene when the mycobacterium infects a mammalian cell. The recombinant gene in these embodiments preferably encodes an antigen of a cancer or a human pathogen, such as a virus, bacterium, or eukaryotic parasite, as discussed above.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

A Newly Identified Protein of *Mycobacterium tuberculosis* Evades Host Responses by Inhibiting Apoptosis

EXAMPLE SUMMARY

*Mycobacterium tuberculosis* is one of most successful pathogens of mankind, adapted for intracellular lifestyle and has extraordinary capacity to subvert host responses. This study describes the role of a newly identified exported protein, NlaA in promoting intracellular survival by evading host cell apoptosis. Deletion of this gene in *M. tuberculosis* resulted in a strain defective in inhibiting apoptosis of human macrophages and in the tissues of infected mice thereby resulting in its attenuation, growth defect and ability to cause less tissue damage.

On the assumption that *M. tuberculosis* secretes or exports proteins that interact with macrophage proteins or non-protein products to enhance its survival in a mammalian host, we undertook a screen for surface associated or secreted proteins using a reporter phoA technology developed earlier (Braunstein at al., 2000). The phoA (*Escherichia coli* alkaline phosphatase) reporter technology has been used successfully in identifying secreted and exported proteins of bacteria (Carroll et al., 2000; Lim et al., 1995). A phoA gene that lacks signals for expression and export is active only when it is located outside of the cytoplasm; therefore, enzymatically active PhoA fusion proteins identify exported proteins. In this report, we describe the role of a novel gene involving the ORF Rv3238c, the hypothetical product of which is homologous to the human nuclear rim protein, Nurim (Rolls et al., 1999), and to Isoprenyl-cysteine-carboxy-methyl-transferase (ICMT) enzyme of many bacteria. Although, the role of ICMT in these bacteria is unknown, it has been shown that inhibition of this enzyme in human pulmonary artery endothelial cell (PAEC) induces apoptosis of these cells, but its overexpression protects against apoptosis (Kramer et al., 2003). This association prompted us to disrupt the Rv3238c gene in *M. tuberculosis* and characterize the resulting mutant in various models of tuberculosis. We hypothesized that Rv3238c is a bacterial effector molecule that enhances survival of *M. tuberculosis* in a mammalian host by preventing macrophage apoptosis.

Our studies demonstrate that the Rv3238c mutant of *M. tuberculosis* is defective in inhibiting apoptosis of human macrophages and in the tissues of infected mice thereby resulting in its attenuation, growth defect and ability to cause less tissue damage in immunocompetent C57/B16 mice. We have thus designated Rv3238c as nlaA (Nurim-like anti-apoptotic) gene.

Materials and Methods

*Mycobacteria* cultures. Cultures of wild-type *Mycobacterium bovis*, *M. bovis bacillus* Calmette-Guérin (BCG), *M. bovis bacillus* Calmette-Guérin (BCG) ΔnlaA, *M. kansasi, M. tuberculosis, M. tuberculosis* ΔnlaA, *M. tuberculosis* ΔnlaA complemented strain were grown to logarithmic phase in Middlebrook 7H9 broth (GIBCO).

THP-1 cells. THP-1 cells (American Type Culture Collection, Manassas, Va.) were grown in RPMI 1640 (Gibco BRL, Gaithersburg, Md.) supplemented with 10% fetal bovine serum (HyClone Laboratories, Logan, Utah), 1% HEPES. The cells were treated with 5 nM phorbol myristate acetate (PMA; Sigma) overnight and then washed three times before infecting them with bacterial strains.

Infection of THP-1 cells. Prior to infection, 10 ml cultures of each mycobacterial strain were pelleted for 5 min, resuspended in PBST and sonicated twice for 10 s (Laboratory Supplies, Inc., Hicksville, N.Y.). Following sonication, dispersed bacterial suspensions were allowed to stand for 5 min, and the upper 500 μl was used in subsequent infections. To ensure an infection ratio of 5 to 10 bacilli per macrophage, multiplicities of infection (MOI) were determined by adding dilutions of prepared bacilli to $1\times10^6$ differentiated THP-1 cells and allowing them to infect for 4 hours.

Colony counting. To quantify *M. tuberculosis* CFU, THP-1 cells were plated and infected as described above. At days 1, 2, 3, 5 and 8 infected cells were lysed in 1% saponin, washed with PBS, and then plated on Middlebrook 7H11 agar plates with 0.05% Tween 80, 10% OADC (GIBCO), 0.5% glycerol. Colonies were counted after 3-4 weeks of growth at 37° C.

Apoptosis assays. Cells were infected with mycobacteria at a ratio of 10 or 5 bacilli to 1 macrophage for 3, 5 and 7 days. At various time points, cells were harvested in 1×PBS-0.5 mM EDTA and washed twice in PBS. The cells were then fixed in 4% paraformaldehyde overnight to kill *M. tuberculosis*. Cells were labeled for TUNEL assay using the manufacturer's protocol (Boehringer Mannheim) followed by FACS analysis. Briefly, the presence of apoptosis in infected and uninfected THP-1 cells was monitored by the presence of DNA fragmentation. The in situ cell death detection assay detected cell death (apoptosis) by labeling DNA strand breaks in individual cells. The method uses terminal deoxynucleotidyltransferase to label free 3'OH ends in DNA with fluorescein-dUTP (TUNEL). This enzymatic labeling allows the detection of a very early apoptotic event. Apoptotic cells are then analyzed by flow cytometry.

Paraffin-embedded infected mouse tissue sections were first deparaffinized by washing the sections in two changes of xylene and then in two changes of ethanol. They were then washed sequentially in 95% ethanol, 70% ethanol, and PBS and then subjected to proteinase K digestion (25° C., 15 min) DNA strand breaks were identified by TUNEL assay using the ApopTag kit (Chemicon international) following the manufacturer's protocol using peroxidase and diaminobenzidene substrate. Hydrogen peroxide was used to quench endogenous peroxidase activity, and the cells were counterstained with hematoxylin and eosin (H&E).

Mouse infections. 7H9 broth (containing hygromycin for the knockout strains or hygromycin plus kanamycin for the complemented strain) were inoculated with frozen stocks of each strain and grown to an $OD_{600}$ of ~1.0. The bacteria were pelleted by centrifugation, washed three times in phosphate-buffered saline containing 0.05% Tween 80, and sonicated briefly using a cup-horn sonicator. Female C57BL/6 mice (6 to 8 weeks old; Jackson Laboratories) were infected with $10^6$ cfu/ml via tail vein injection or ~100 to 200 CFUs by the aerosol route using a nose-only aerosolization system as described earlier (Schwebach et al., 2002). At various time-points after infection, mice were sacrificed and the lungs, spleens, and livers were homogenized in phosphate-buffered saline containing 0.05% Tween 80. Tissue bacterial load was assessed by plating serial dilutions of the homogenates onto 7H10 agar, containing hygromycin as appropriate for the knockout strain. Portions of the lungs, liver, and spleen were also fixed overnight in 10% phosphate-buffered formalin, embedded in paraffin, sectioned, and stained with hematoxylin and eosin for histologic evaluation and photography. Four to five mice per group were sacrificed at each time point.

Results

Inhibition of macrophage apoptosis by Rv3238c/nlaA. The wild-type *M. tuberculosis* H37Rv and the ΔnlaA strain did not differ in terms of their growth kinetics in 7H9 medium. The human promonocytic THP-1 cell line is a valid in vitro model for studying mycobacteria induced apoptosis (Riendeau and Kornfeld, 2003). PMA differentiated THP-1 cells were infected with *M. tuberculosis* H37Rv, *M. tuberculosis* ΔnlaA, or the complemented strain. TUNEL labeling using in situ cell death detection kit (Boerhinger) followed by flow cytometric analysis were used to measure apoptosis in infected cells. Consistent with the earlier published studies, we were able to show that the avirulent strains viz. *M. bovis* BCG, *M. kansasii* were able to induce more apoptosis than the virulent H37Rv (FIG. 1). The *M. tuberculosis* ΔnlaA mutant induced more apoptosis than wild-type H37Rv at all the time points studied which was not a result of limited replication in vitro (FIGS. 2A and B). We chose day 3 as the time point for all future experiments since the difference in the levels of apoptosis was most prominent at this time point. While 6.26% of cells infected with wild-type H37Rv underwent apoptosis at three days post-infection, 20.18% of cells infected with the *M. tuberculosis* ΔnlaA mutant exhibited apoptosis (FIG. 3). To directly prove that this phenotype resulted from the loss of the nlaA gene, the ΔnlaA mutant was complemented with the wild-type copy of the gene and this resulted in the restoration of the apoptosis to wild-type levels ($P<0.02$) (FIG. 4). It has been shown that inhibition of apoptosis is a virulence-associated trait and attenuated strains like the H37Ra induce more apoptosis than the virulent H37Rv (Keane et al., 1997). To further confirm that the phenotype was a result of the disruption of nlaA gene, and not a characteristic of all attenuated strains we tested the ΔpanCD mutant, known to be attenuated in mice (Sambandamurthy et al., 2002) in inducing apoptosis. Our results show that ΔpanCD mutant induced as much apoptosis as the wild-type H37Rv strain (FIG. 4). We thus named the gene nlaA for Nurim Like anti-apoptotic (nlaA) gene based on its ability to inhibit apoptosis. It is unlikely that the differences observed were due to impaired infectivity, since the number of viable bacteria recovered per well after 4 h of infection was the same for all strains tested.

Growth characteristics of ΔnlaA mutant in mice. We studied the ability of the *M. tuberculosis* strains to survive in the tissues of immunocompetent C57BL/6 mice by CFU analysis after intravenous and aerosol infection. The C57BL/6 strain of mice is known to restrict the proliferation of *M. tuberculosis* in tissues and would thus amplify the survival defects in attenuated strains (Orme, 2003). We used a low-dose murine aerosol infection model of chronic persistent infection (Scanga et al., 2001) to examine the in vivo phenotype of the *M. tuberculosis* ΔnlaA mutant. Following an aerosol exposure of 100 bacilli in the lungs as seen by bacterial counts 24 hours post-infection, the mice were monitored for a period of 21 weeks. At 3 weeks post-infection, enumeration of the bacterial burden within the lung and spleen revealed that the ΔnlaA strain proliferated less than that of the wild-type H37Rv (FIG. 5). The wild-type and the mutant grew exponentially for 3 weeks post-infection and reached constant titers by 21 weeks. Strikingly, the mutant showed a growth defect and persisted at about 1 log less in the lungs in comparison to H37Rv at all time points both in the spleen and the lungs of infected mice (FIG. 5).

After intravenous challenge each mouse received about $10^4$ bacteria in the lungs and about $10^5$ bacteria in the spleen as seen at 24 hours post-infection. The ΔnlaA mutant and H37Rv strains grew exponentially for the first three weeks following infection. However, the mutant was seen to grow less than the wild-type by week 8 in the lungs of these mice. At week 34, the mutant persisted at about $10^5$ bacteria in the lungs while the wild type reached a constant titer of $10^6$ bacteria (FIG. 6A). A similar growth pattern was seen in the spleens of these mice, where both the mutant and wild-type grew at comparable rates for 8 weeks post-infection followed by a sharp decline in the ΔnlaA titers. By week 34 the ΔnlaA mutant reached a bacterial count of about $10^5$ while the wild type persisted at constant titers (FIG. 6B). Overall, the intravenous and aerosol infection of C57BL/6 mice shows that the deletion of nlaA gene in M. tuberculosis results in observable defects in growth and persistence demonstrating a significant attenuation of this strain.

Figure 6:
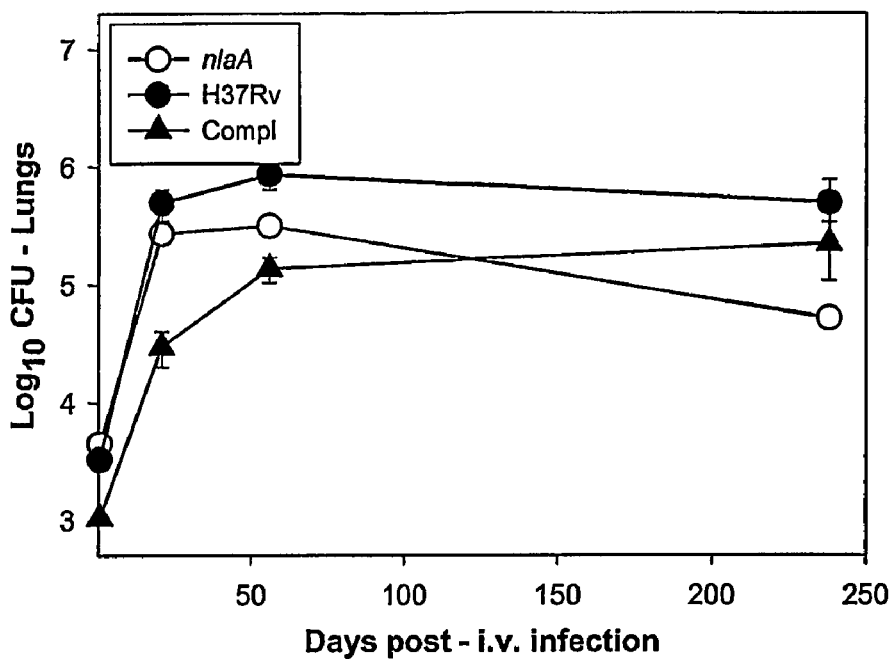
FIG. 6 is graphs showing the deletion mutant displays growth defects in the organs of infected mice. Total CFU counts of wild-type *M. tuberculosis* H37Rv (●), *M. tuberculosis* ΔnlaA (◇) and the complemented strain (▲) at various time points in lungs (A) and spleen (B) of mice infected intravenously (a & b). Data are expressed as log 10 value of mean number of bacteria+/−standard deviation recovered from each mouse. Groups of four mice were evaluated at each time point. *$p<0.01$ compared to wild-type H37Rv
Figure 6:
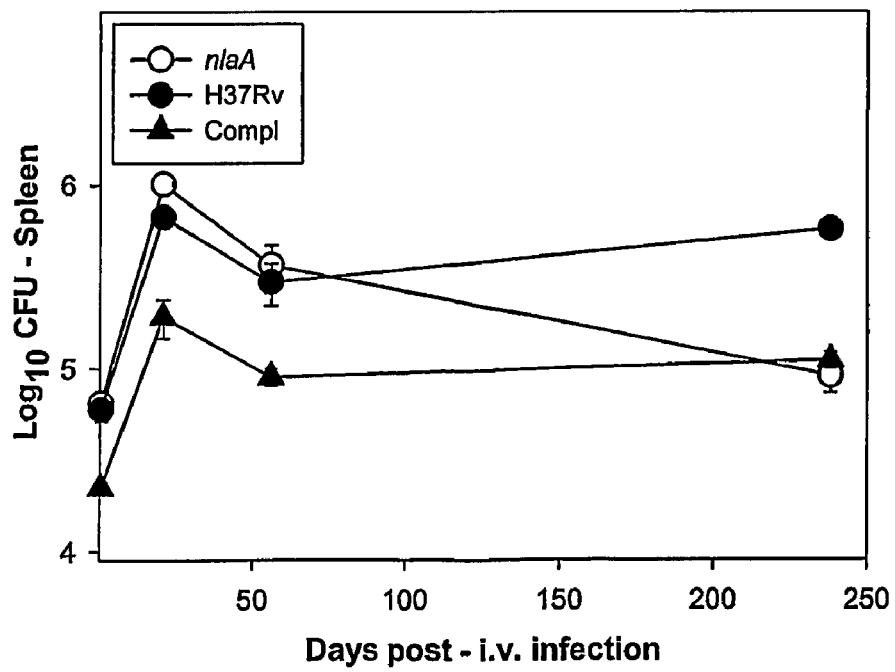
Figure 7:
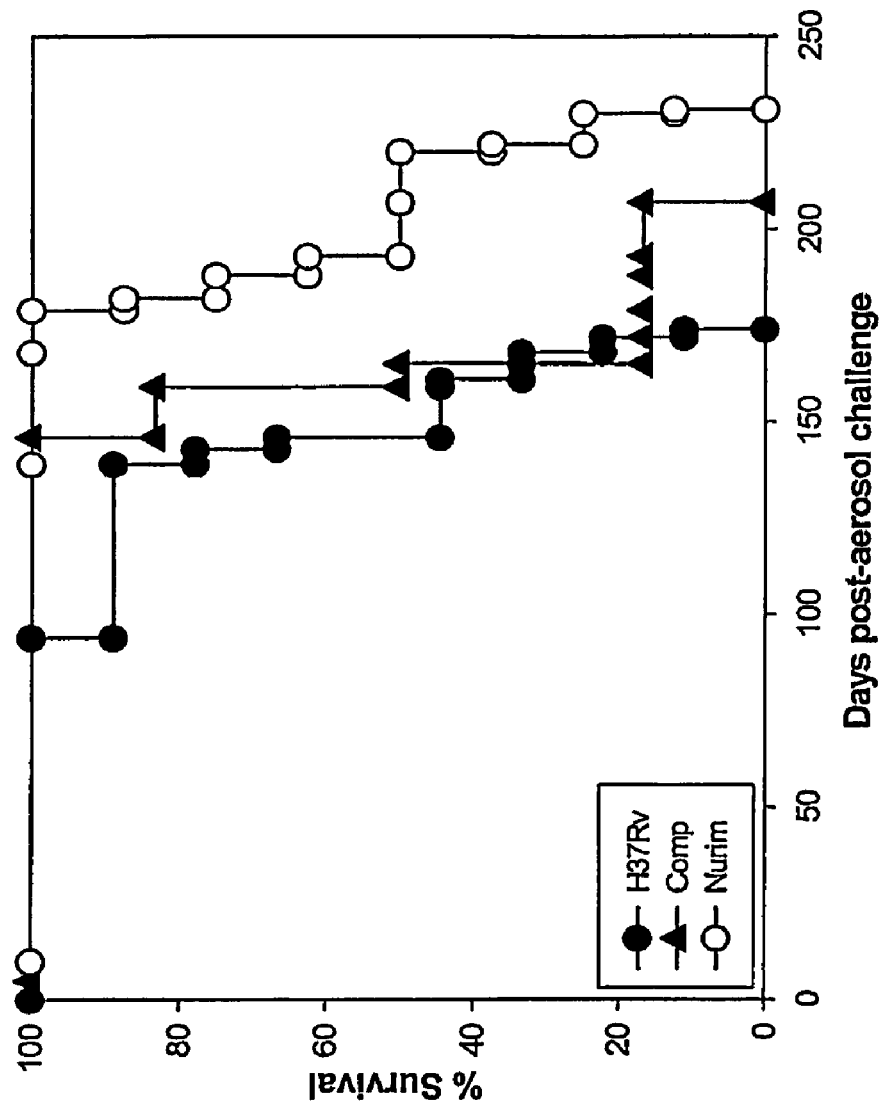
FIG. 7 is a graph showing the deletion mutant is attenuated in mice. Time-to-death analysis in C57B1/6 mice upon aerosol infection with wild-type *M. tuberculosis* H37Rv (●), *M. tuberculosis* ΔnlaA (◇) and the complemented strain (▲) shows significant mortality delay. The inoculum was 100 cfu for aerosol infection (n=10). $p<0.0001$ compared to wild-type H37Rv and complemented strain.
Figure 8:
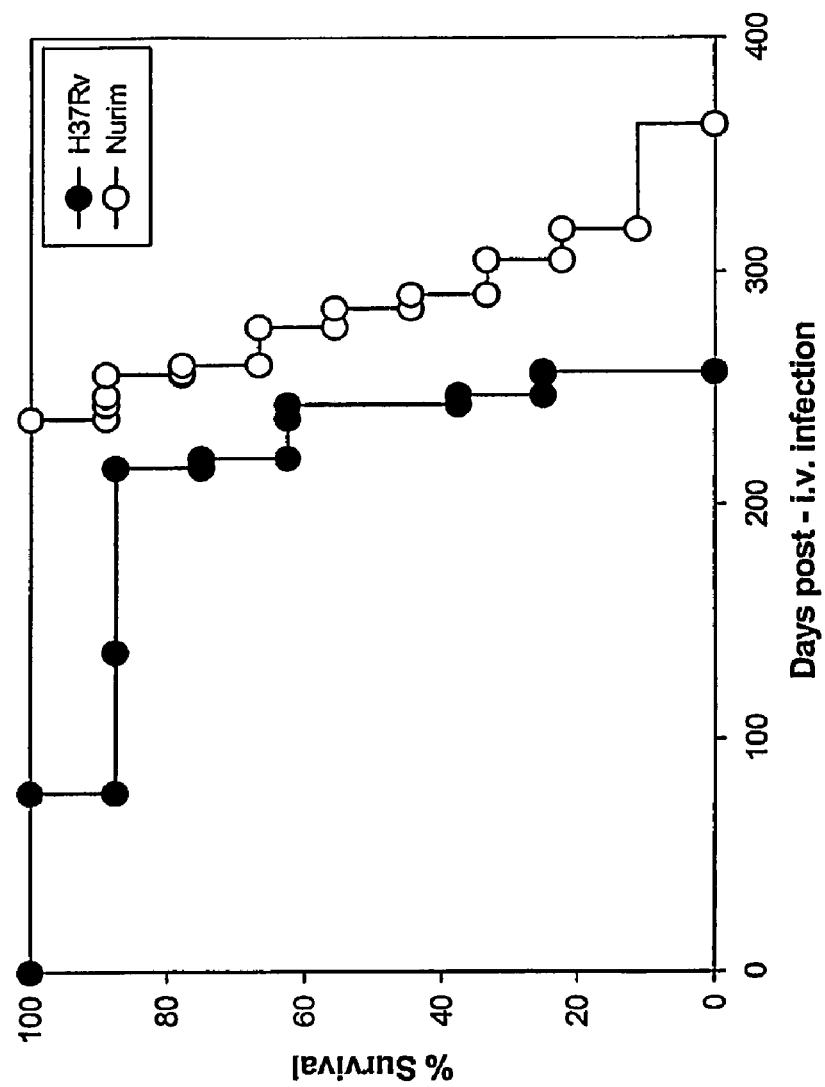
FIG. 8 is a graph showing the deletion mutant is attenuated in mice. Time-to-death analysis in C57B1/6 mice upon intravenous infection with wild-type *M. tuberculosis* H37Rv (●), *M. tuberculosis* ΔnlaA (◇) and the complemented strain (▲) shows significant mortality delay. The inoculum was $10^6$ cfu (n=10). $p<0.0001$ compared to wild-type H37Rv.
Figure 9:
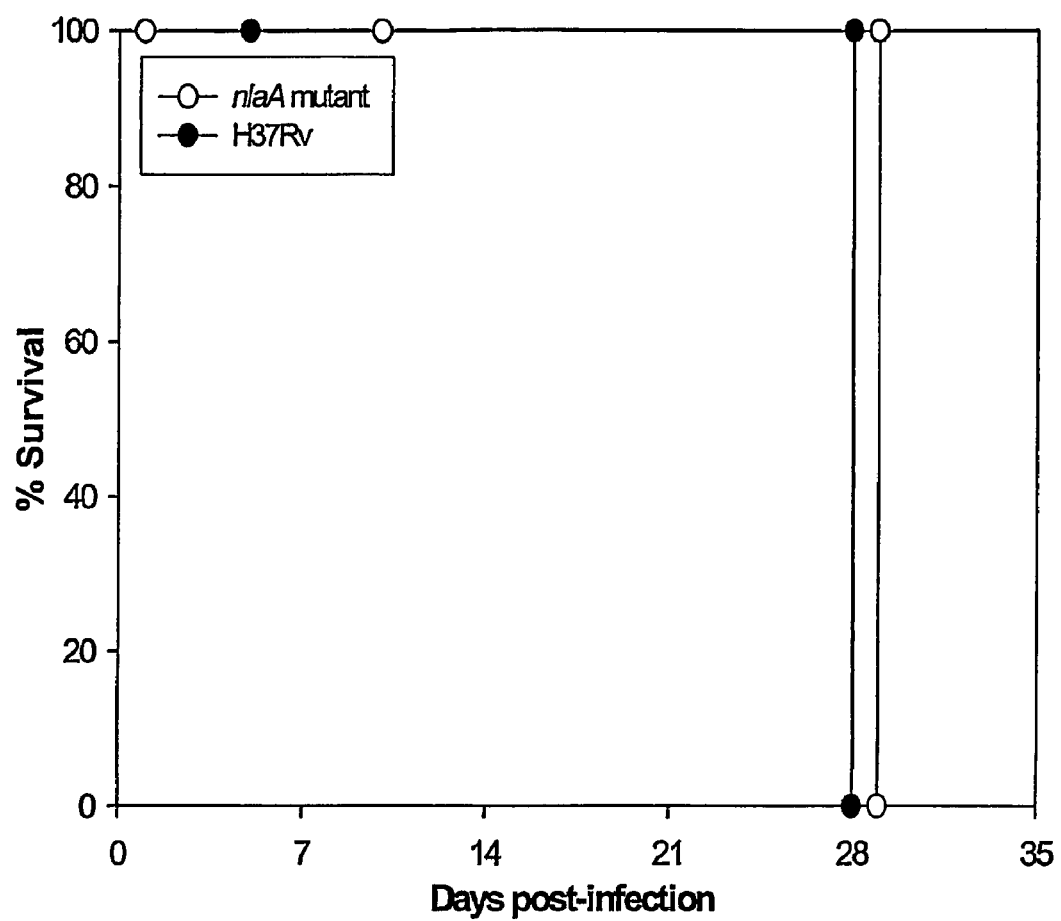
FIG. 9 is a graph demonstrating that SCID mice display similar mortality rates with the wild-type strain and the deletion mutant. The inoculum was $10^4$ cfu (n=10).

Virulence of M. tuberculosis ΔnlaA mutant in immunocompetent mice. Another relevant measure of virulence is to assess the relative survival periods of infected mice (North, 1995). We performed time to death analysis to determine if the lesser growth of the ΔnlaA mutant manifested in prolonged survival of infected mice. When the C57B1/6 mice were infected with various mycobacterial strains either by intravenous or aerosol route, mice infected with the ΔnlaA mutant displayed a pronounced attenuation in the time to death in both models of infection. The median time-to-death for the mutant infected via the aerosol route exceeded 225 days and that of the wild-type and the complimented strain was about 150 and 160 days respectively (FIG. 7). In mice infected intravenously, the median-time to death for the mutant was about 300 days and that of the wild-type was about 250 days (FIG. 8). The mice infected with the complemented strains intravenously survived longer than the mutant, which can be attributed to the low inoculum of bacteria in the infection as seen in growth curves of these strains in FIGS. 5 and 6. Interestingly, SCID mice infected with the mutant or the WT did not show any significant differences in mortality (FIG. 9). This result suggests that the nlaA gene induces protective response through the adaptive immune mechanism.

Figure 10:
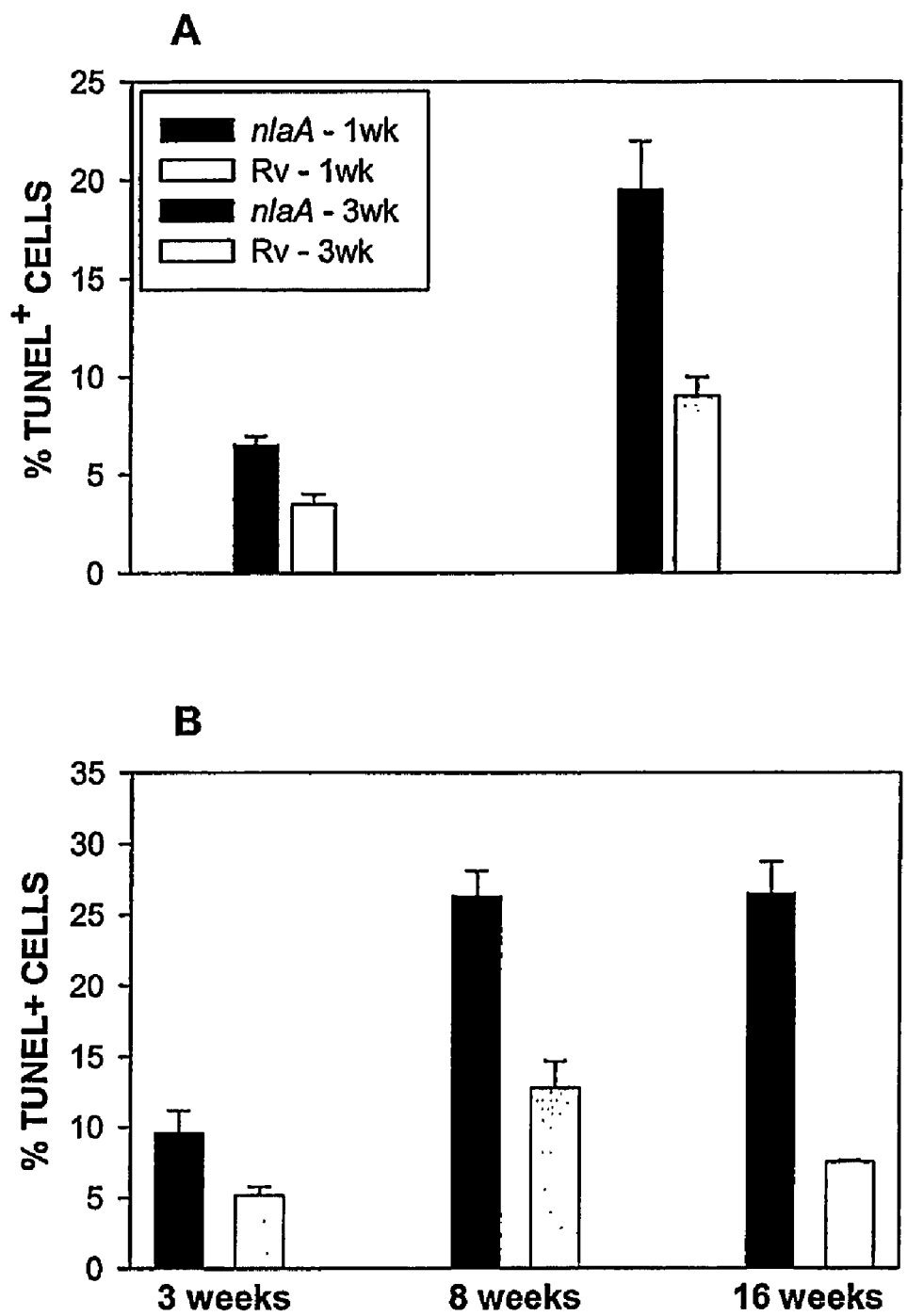
FIG. 10 is graphs showing that the deletion mutant displays more apoptotic cells in the organs of infected mice. Percentage apoptotic cells as determined by review of multiple 40× magnification fields following staining with TUNEL in the spleens (A) and lungs (B) of mice infected with $10^6$ cfu of the M. tuberculosis ΔnlaA (filled bars) and the virulent wild-type M. tuberculosis H37Rv (empty bars). Nuclei of cells undergoing apoptosis stain brown with TUNEL.
Figure 11:
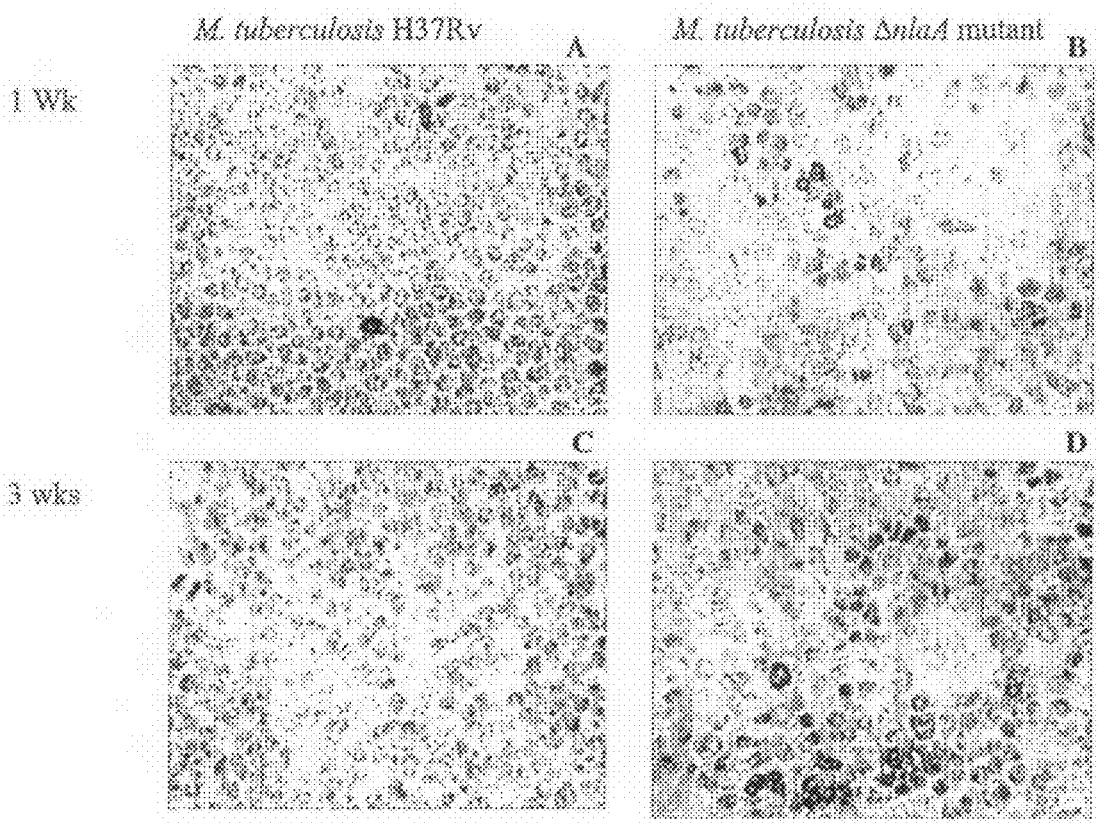
FIGS. 11 and 12 are micrographs of stained cells showing the deletion mutant induces increased levels of apoptosis in vivo. Representative TUNEL-stained views of spleen tissue sections (FIG. 11) and lung tissue sections (FIG. 12) harvested at 1 week and 3 weeks following intravenous infection with $10^6$ cfu of M. tuberculosis ΔnlaA and the wild-type M. tuberculosis H37Rv photographed at 40×. Nuclei of cells undergoing apoptosis stain brown with TUNEL.

Apoptosis analysis in the mouse tissue sections. TUNEL assessment of DNA fragmentation in the spleen of mice infected with ΔnlaA mutant showed that about 20% of the cells were apoptotic at 3 weeks post infection (FIG. 9). In the lungs of these mice apoptosis increased markedly from 10% at 1 week to about 20% at 16 weeks post infection. In contrast, although apoptosis was identified mice infected with virulent M. tuberculosis, it appeared to be less than that induced by the mutant strain. By 16 weeks, mice infected with virulent bacilli exhibited minimal apoptosis (<10%). Histopathology analysis of TUNEL stained sections of these mice are depicted in FIGS. 10 and 11. These results correlate with the reduced growth of the mutant strains as opposed to the wild type strains in the organs of intravenously infected mice (FIG. 6).

Figure 12:
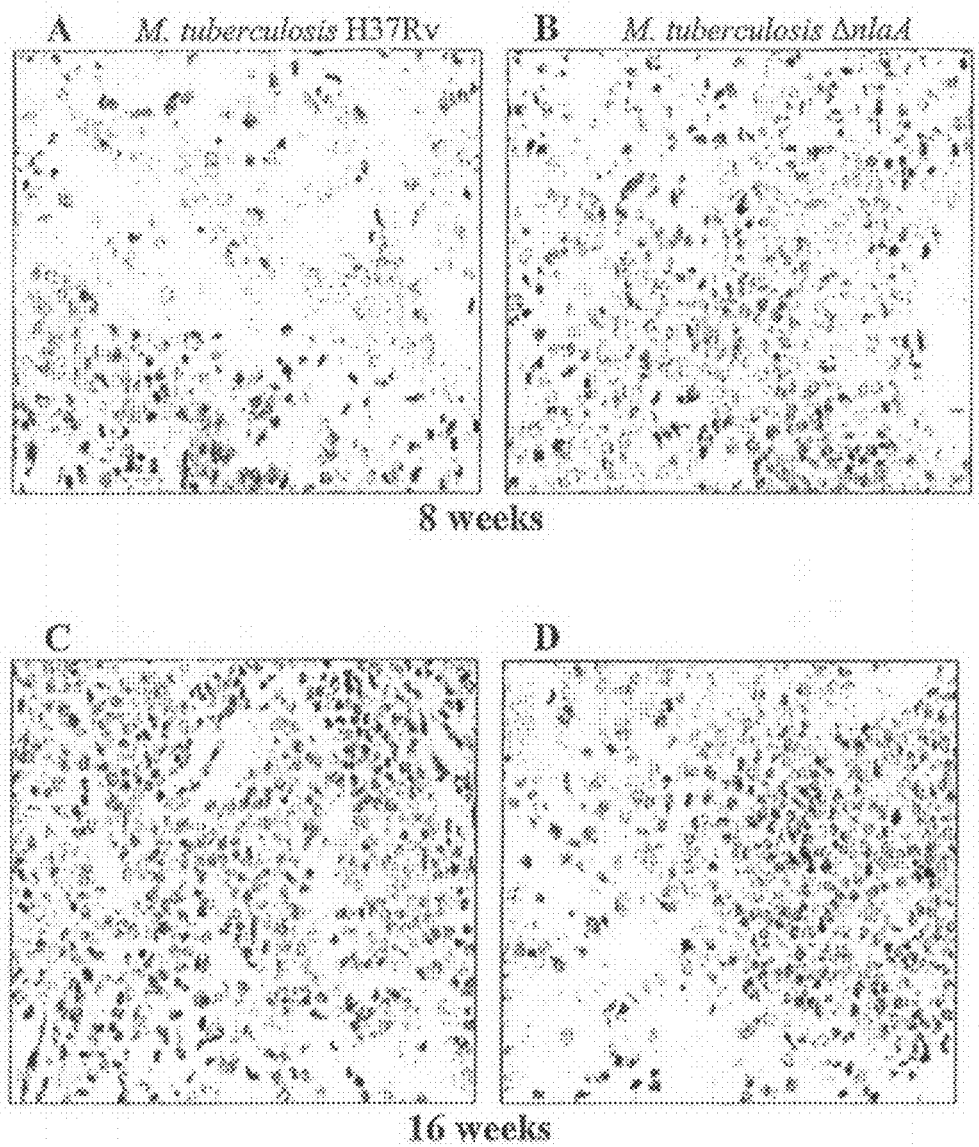
Figure 13:
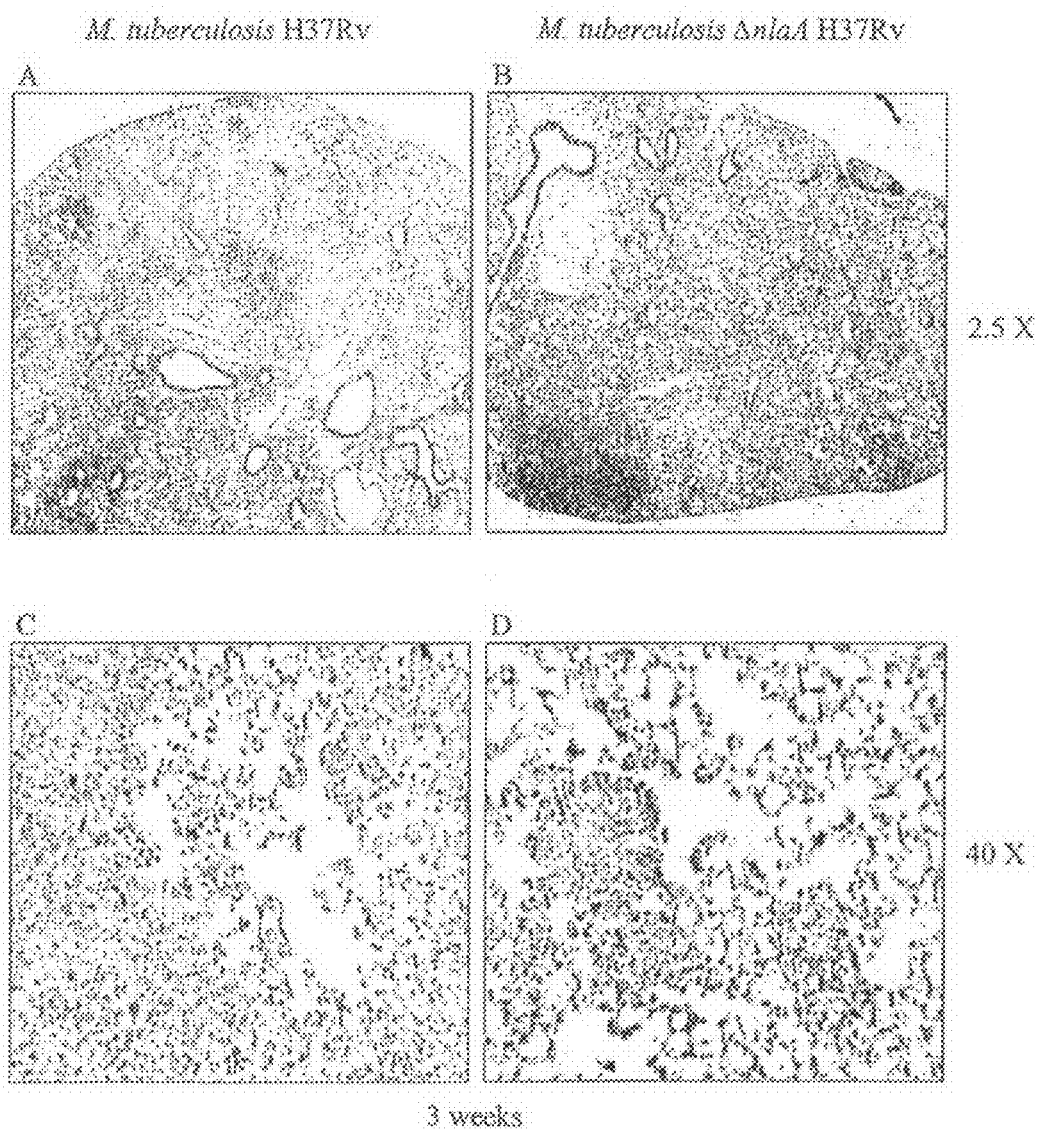
FIGS. 13 to 16 are micrographs showing the deletion mutant produces less tissue pathology in the lungs of infected mice compared with wild-type M. tuberculosis H37Rv. C57BL/6 mice infected with 100 CFU by aerosol route were evaluated at 3 weeks (FIG. 13), 8 weeks (FIG. 14), 12 weeks (FIG. 15), and 21 weeks (FIG. 16) at 2.5× (A, B) and 40× (C, D) following hematoxylin and eosin staining of lung tissues.
Figure 14:
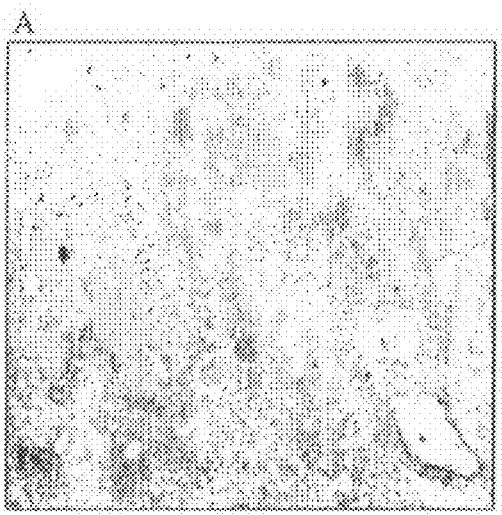
Figure 14:
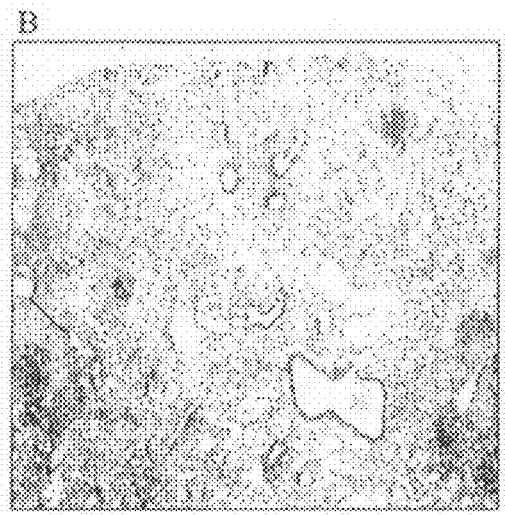
Figure 14:
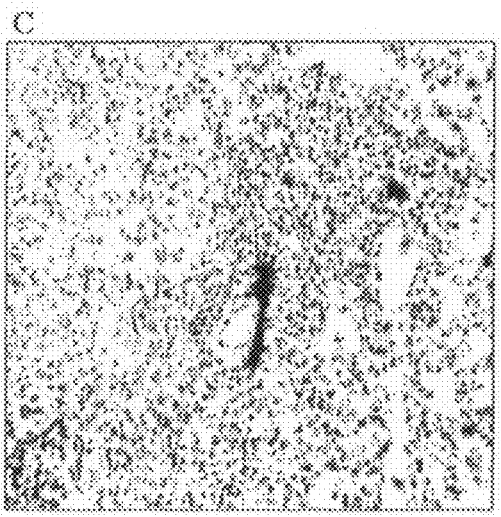
Figure 14:
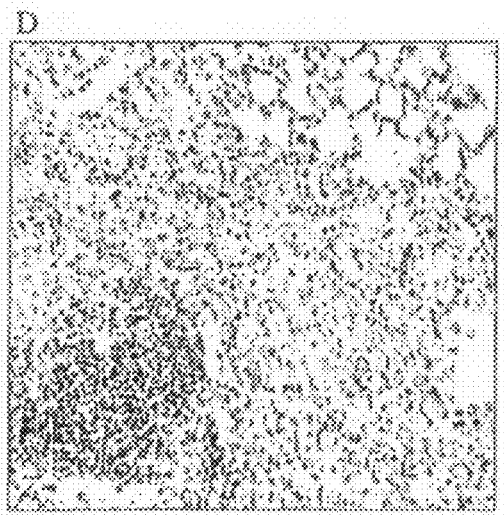
Figure 15:
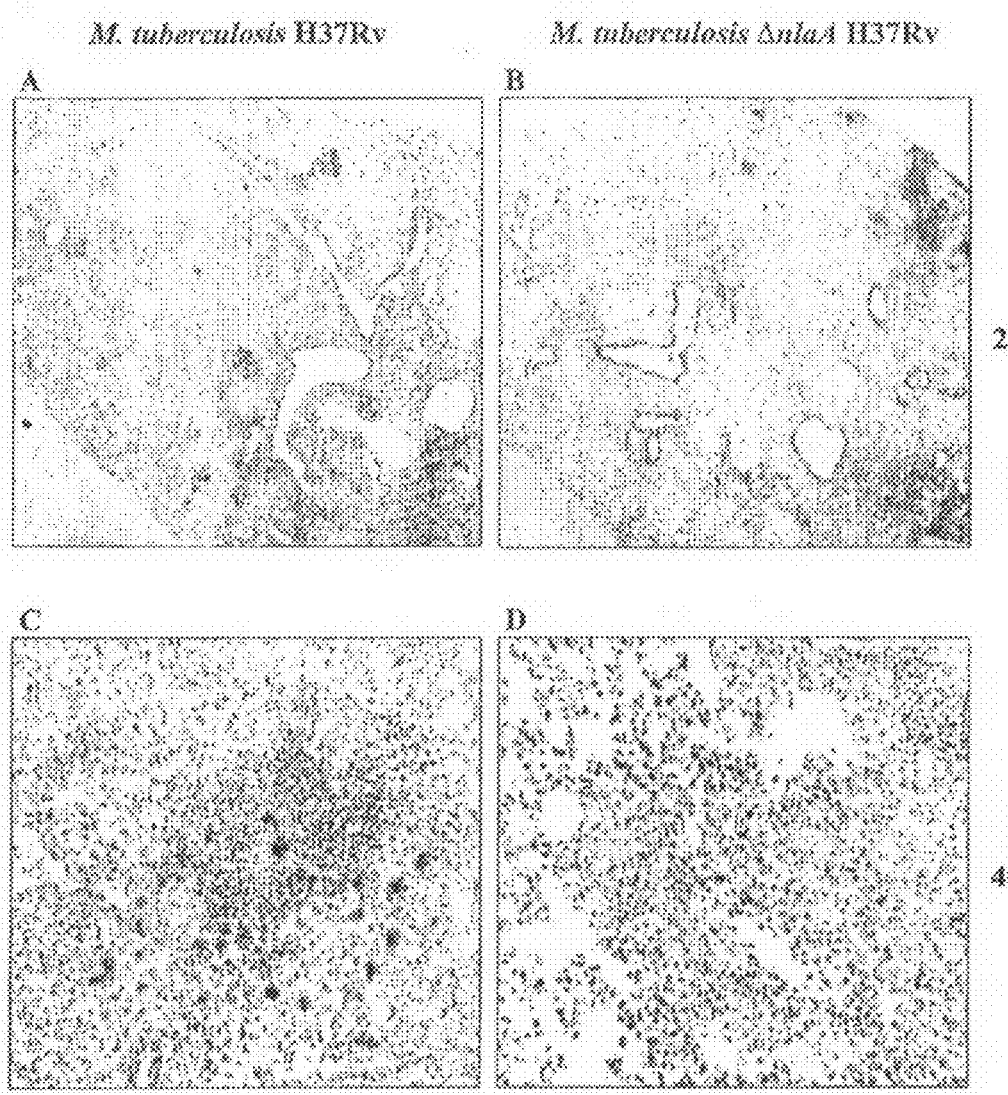
Figure 16:
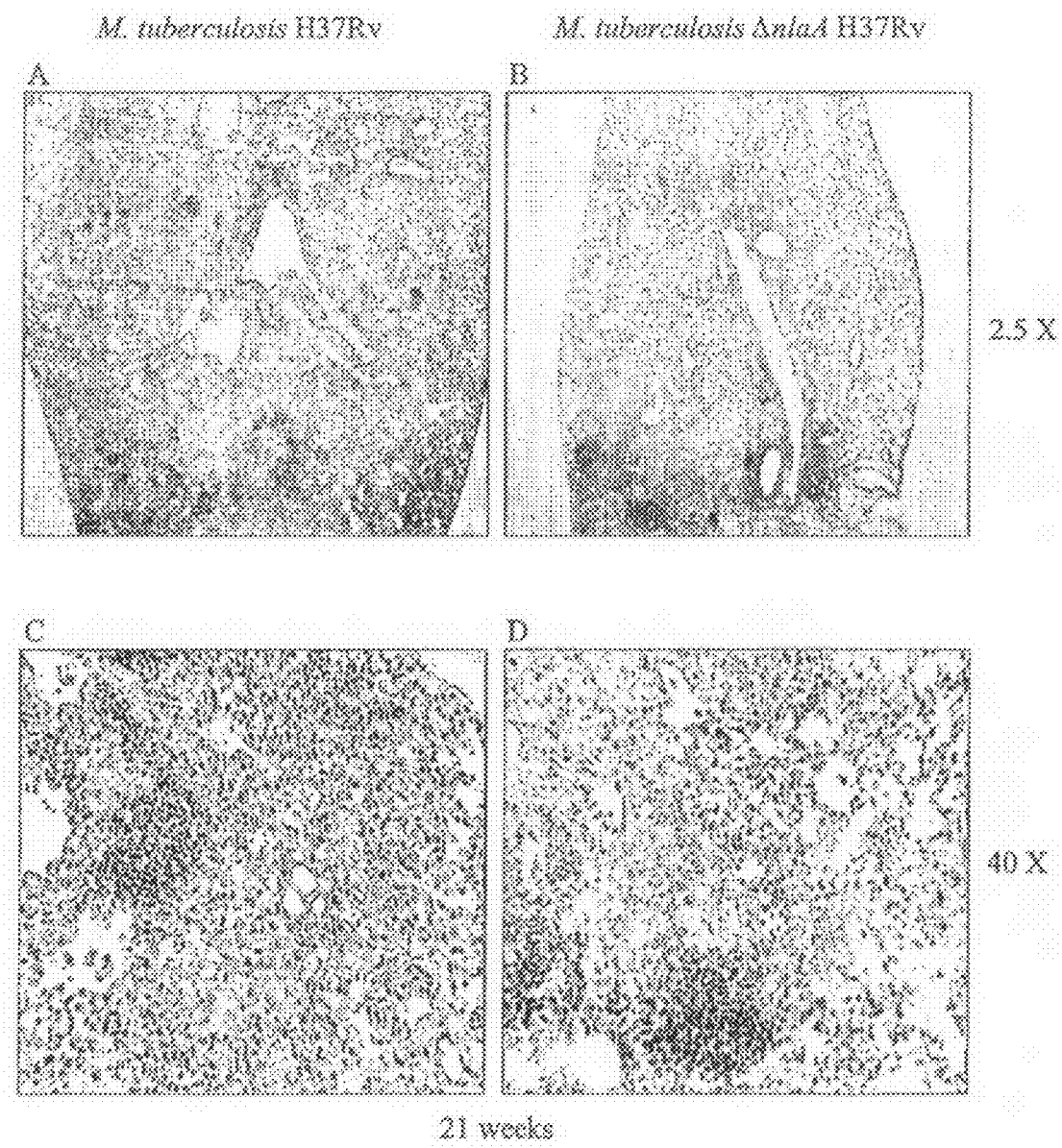
Figure 17:
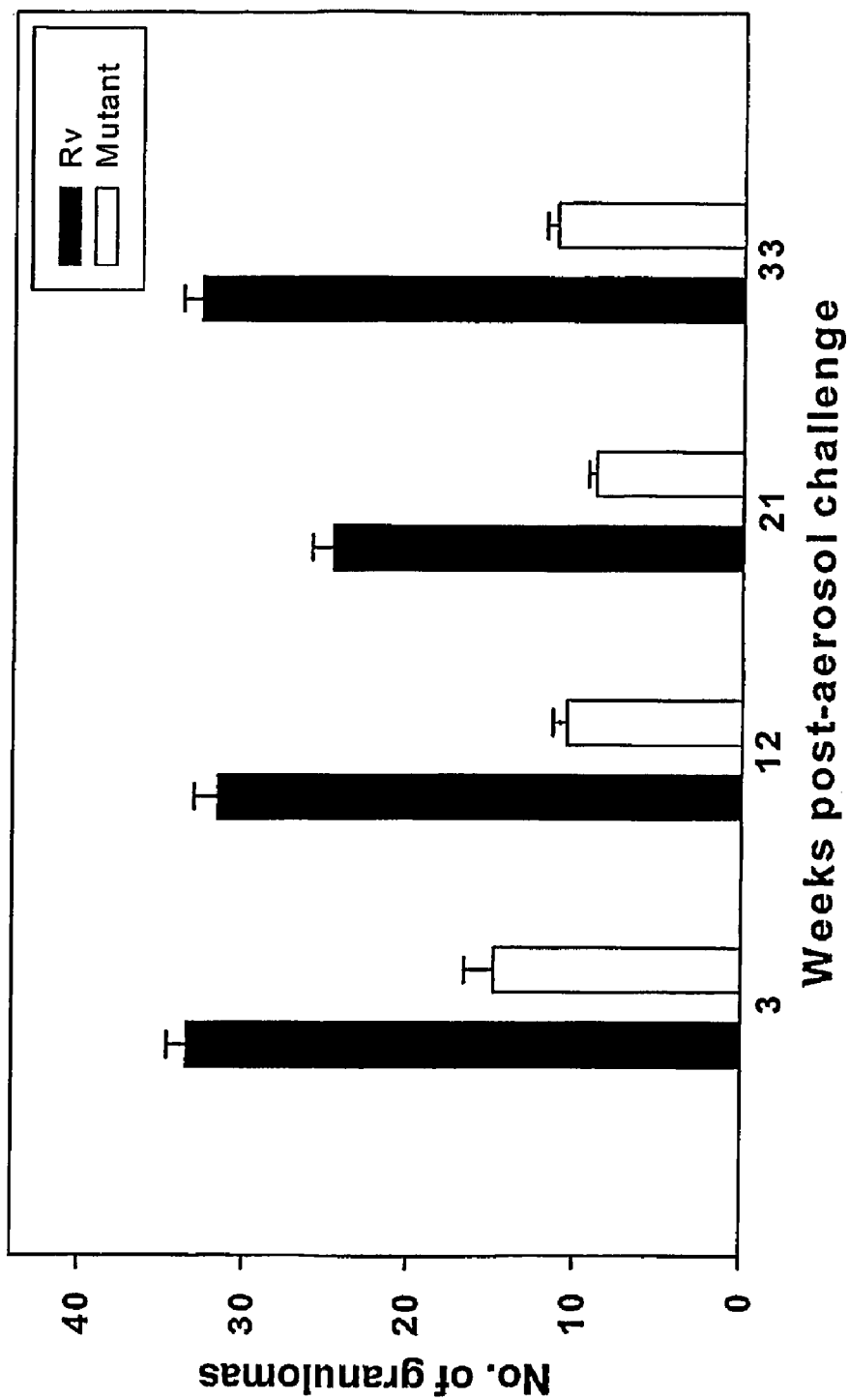
FIG. 17 is a graph showing the deletion mutant produces less tissue pathology in the liver of infected mice compared with wild-type M. tuberculosis H37Rv. Graphical representation of the number of granulomas as determined from review of the whole liver following intravenous infection of C57BL/6 mice with M. tuberculosis ΔnlaA or wild type M. tuberculosis. Four sections from each mouse were reviewed at 10× magnification and groups of three mice and two sections per mouse were evaluated for each time point.

Histopathological analysis of mouse tissue sections. Granuloma formation is the key component of adaptive immune response to mycobacterial infection and is influenced by the tissue burden and the virulence of the infecting organism. At 3 weeks post-infection, histopathological analysis of lung tissue from aerosol infected mice, showed that both wild-type and mutant strain produced comparable degrees of interstitial inflammation with small scattered foci of organizing lesions (FIG. 12). At 8 and 12 weeks, granulomatous lesions began to form in both mutant and wild-type infected tissues. However, lungs of wild-type infected mice showed increasing granuloma size, coalescence of the lesions due to excessive infiltration of lymphocytes and foamy macrophages become evident in the granuloma. The lungs of the ΔnlaA mutant infected mice showed retarded disease progression and showed lesser pathological evidence than that of the wild-type (FIGS. 13, 14). Analysis of the lung tissue of mice infected with wild-type at later time points of 21 weeks and 33 showed progressive granulomatous inflammation with loss of functional alveoli attributable to enlarging and coalescing lesions. The tissues from ΔnlaA infected mice showed smaller, less abundant and more discrete granulomas. At the level of gross pathology, there were apparent differences between tissues infected with the wild-type and mutant strain, the organs of mutant infected mice has smaller and fewer granulomas and less inflamed than that of the tissues from wild-type infected mice (FIG. 15, 16, 17).

Discussion

Based on a phoA reporter technology developed in our lab (Braunstein et al., 2000), we have identified a novel protein of M. tuberculosis, NlaA. In this study, we report that a mutant of this gene can induce apoptosis of infected cells. M. tuberculosis infection results in intracellular survival and proliferation within the macrophages they infect (Bermudez and Goodman, 1996). Apoptosis is the cellular response to this deregulation of growth control by M. tuberculosis and it results in suicide elimination of mycobacteria infected cells (Molloy et al., 1994). In the current study, we have consistently shown that the ΔnlaA mutant induces significantly more apoptosis in the THP-1 monocytic cells than its parental wild-type strain or the complemented strain. We chose to use the THP-1 cells as a model for studying apoptosis since differentiated THP-1 cells closely model the behavior of primary human alveolar macrophages (Riendeau and Kornfeld, 2003), which constitute the critical growth niche for M. tuberculosis after aerosol infection (Leeman et al., 2001). Despite the comparable growth rates of the ΔnlaA mutant and the wild type in these cells, ΔnlaA showed more apoptosis suggesting that differential levels of cell death were independent of replication in vitro. This is consistent with observations by other groups that bacillary control of host cell apoptosis is a virulence-associated phenotype of M. tuberculosis. Keane et al have shown that infection of alveolar macrophages with virulent M. tuberculosis results in reduced levels of apoptosis and cytotoxicity as opposed to attenuated or virulent isogenic strains (Keane et al., 2000). Similarly, macrophages from mice resistant to mycobacterial infection are more susceptible to M. tuberculosis induced apoptosis (Rojas et al., 1997). Apoptosis is considered a defense strategy to limit the growth of intracellular pathogens (Moore and Matlashewski, 1994; Nash et al., 1998; Vaux and Strasser, 1996). The importance of this innate defense mechanism is demonstrated in the evolutionary acquisition of apoptosis inhibition genes by many viruses (Teodoro and Branton, 1997). There is precedence among other intracellular pathogens for blocking macrophage apoptosis as a means to enable continued intracellular parasitism (Fan et al., 1998; Gao and Abu Kwaik, 2000; Moore and Matlashewski, 1994; Nash et al., 1998). However, for induction of apoptosis, mycobacterial effector molecule/s directly or indirectly interfere with the apoptotic pathway. The mannosylated lipoarabinomannan of M. tuberculosis can inhibit apoptosis (Rojas et al., 2000) and the recent evidence that superoxide dismutase (SOD) diminished strains are less virulent in mice (Edwards et al., 2001) suggests that apoptosis plays a role in the attenuation of mycobacteria. On the contrary, laboratories have reported that the purified protein derivative (PPD) and the 19 kDa protein from *M. tuberculosis* (Lopez et al., 2003; Rojas et al., 1997; Rojas et al., 1999) can induce apoptosis of human monocytes. Therefore, regulation of mechanism of phagocytic cell death by *M. tuberculosis* is a multifactorial process.

In an attempt to further characterize the nlaA gene, the growth of the mutant strain was evaluated in C57/BL6 mice model. Wild-type *M. tuberculosis* H37Rv and the ΔnlaA mutant replicated equally well in the 7H9 broth. The ΔnlaA however showed reduced growth during the acute phase of infection in the lungs and spleen of mice infected via the aerosol route. The mutant was maintained at titers less than that of the wild-type till 21 weeks after which the experiment was terminated. In mice infected intravenously the mutant and the wild type grew to similar titers for the first three weeks post infection followed by a decline in the mutant titers. The ΔnlaA mutant was maintained at titers less than that of the wild-type in both the spleen and the lungs of infected mice up to 34 weeks. Whereas, the ΔnlaA mutant strain grew at rates similar to that of the nlaA proficient strains in THP-1 cells and bone marrow derived macrophages from C57BL/6 mice (data not shown), in animals the mutant showed a decline in growth in organs of infected mice. This suggests that the reduced growth of the ΔnlaA in vivo did not result primarily from a lower intrinsic capacity to replicate, but due to the interaction between mycobacteria and the host. Using the same model of immunocompetent mice we were able to demonstrate the prolonged survival, over 50 days, of mice infected with ΔnlaA intravenously or via aerosol route.

A complex balance exists: *M. tuberculosis* can inhibit apoptosis in directly infected cells to facilitate intracellular replication or survival and alternatively, the host needs to induce apoptosis in these cells to inhibit microbial replication. *M. tuberculosis* disturbs this balance, as evidenced in patients infected with the tubercle bacilli. Monocytes from patients with TB undergo apoptosis, as well as necrosis after infection with virulent *M. tuberculosis*, whereas monocytes from PPD+ healthy donors undergo only apoptosis, which was more than the level of apoptosis in infected patients (Gil et al., 2004). In one of the first descriptions of apoptosis, cells undergoing this form of cell death showed reduction in the viability of BCG, whereas necrotic death of these cells resulted in no intracellular mycobacterial inhibition (Molloy et al., 1994). Classical descriptions of histology of the tuberculous granuloma refer to caseous necrosis at tissue level and "burst" of bacilli laden macrophages as the cause of bacterial dissemination and tissue damage (Dannenberg, 1993). Since apoptotic cells can kill the tubercle bacilli in vitro (Duan et al., 2001; Molloy et al., 1994; Oddo et al., 1998), and owing to the marked differences in levels of apoptosis in vitro that was unique to infection with the ΔnlaA mutant, we assumed that apoptosis is the factor for the reduced growth rate of the mutant in vivo. Apoptosis was prominent among the cells in the spleen and lungs of mice infected with the ΔnlaA strain but reduced in mice infected with virulent *M. tuberculosis* H37Rv. This increased rate of apoptosis correlated with the fall in bacillary load seen in the spleen and the lungs over time, compared to the rapid rise by virulent *M. tuberculosis* strains. Further, our histopathology analysis on the hematoxylin and eosin staining stained sections of infected mice, shows pathological disease in the tissues of mice infected with the wild-type *M. tuberculosis*. Overt changes were seen in the lungs of mice infected with the ΔnlaA mutant as compared to wild type, where the granulomas were clearly visible. In the lungs of *M. tuberculosis* infected mice the granulomas were discretely spread over the lung area and seemed to coalesce in later stages of infection. The mutant infected lungs had smaller and less abundant granulomas as were the other tissues infected with this mutant. Since the ΔnlaA mutant exhibited suppressed bacterial replication and pathological disease in the organs of mice infected, at the same time being less pathogenic to these mice as reflected by their extended survival periods, it is feasible to say that the mutant induced apoptosis contributes to the attenuation of virulence through restricting the bacteria in the mouse lungs. It can be reasoned that in the absence of apoptosis, the bacilli continue to replicate, and the host cell eventually explodes as a result of membrane damage.

Host induction of apoptosis have other advantages in addition to controlling intracellular replication, as apoptotic macrophages can be used as a source of antigen for presentation by bystander dendritic cells (Schaible et al., 2003; Yrlid and Wick, 2000). Therefore, in addition to impairing the innate immune response by inhibition of apoptosis and intracellular survival, *M. tuberculosis* affects the adaptive response by this host evasion strategy. This is indeed possible since SCID mice infected with the wild type and the ΔnlaA mutant displayed identical mortality rates, which explains the limited growth rate ΔnlaA during the adaptive phase of the immune response. Therefore, protective immunity in these mice infected with the nlaA mutant is a result of innate and acquired defense mechanisms.

Figure 18:
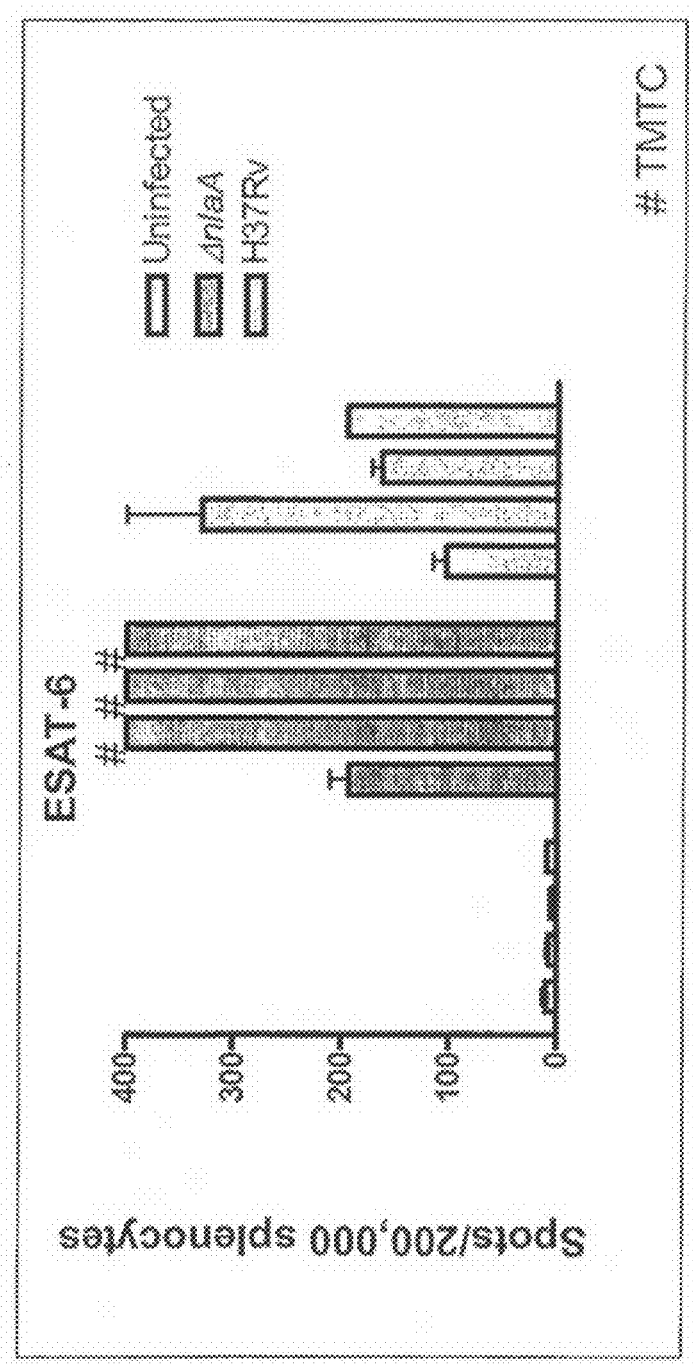
FIG. 18 is a graph of the CD4+ cells reactive against ESAT-6 in mice infected with ΔnlaA or wild type M. tuberculosis. Normal C57BL/6 mice were infected by the intravenous route with $10^6$ colony forming units of either Mycobacterium tuberculosis H37Rv or the ΔnlaA mutant of H37Rv. Four mice were infected with each strain, and an additional four mice were left uninfected as controls. After 4 weeks, the animals were sacrificed, their spleens removed and used to prepare single cell suspensions. Cultured splenocytes from each mouse were stimulated in triplicate cultures with 100 micrograms/ml of purified recombinant M. tuberculosis ESAT-6 protein antigen, and after 24 hours were analyzed by interferon-γ (IFNγ) ELISPOT. Results show significant induction of ESAT-6 reactive IFNγ-producing T cells in mice infected with both strains compared to control uninfected mice. Most notably, there were markedly elevated levels in three of the four ΔnlaA infected mice compared to mice infected with wild type H37Rv. Each bar represents one mouse. Note that this assay detects almost exclusively CD4+ T cells.
Figure 19:
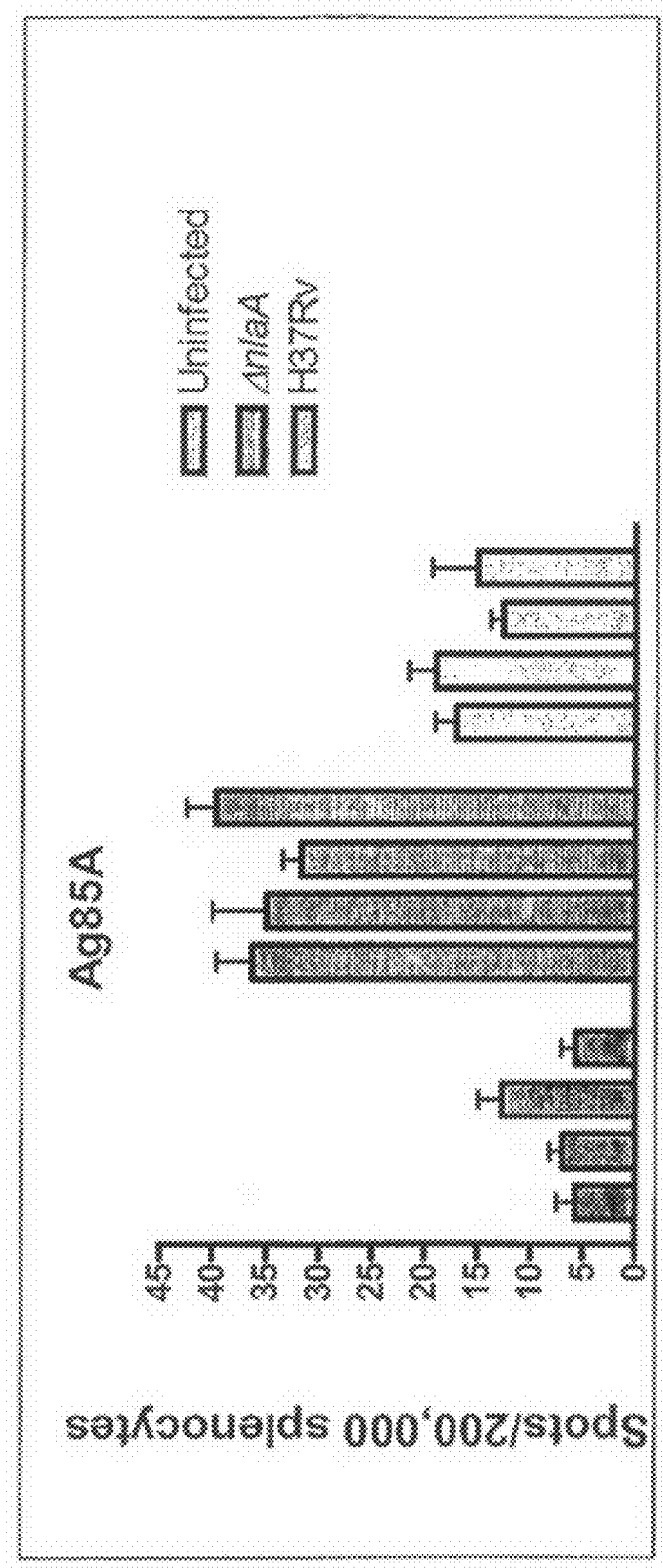
FIG. 19 is the same as FIG. 18, except that splenocytes were stimulated with 100 micrograms/ml of purified recombinant M. tuberculosis Ag85A antigen. As with the ESAT-6 response, significant numbers of IFNγ producing T cells were detected against this antigen in all infected mice, and the numbers were significantly greater for the animals infected with the ΔnlaA strain.

Immunity induced by the ΔnlaA mutant was compared with immunity induced by a wild type *M. tuberculosis*. The ΔnlaA mutant strain induced greater immunity, as determined by CD4+ T cells reactive against two separate antigens. See FIGS. 18 and 19.

EXAMPLE 2

*Mycobacterium tuberculosis* nuoG is a Virulence Gene that Inhibits Apoptosis of Infected Host Cells

*Mycobacterium tuberculosis* is an extremely successful pathogen that has already infected approximately one third of the world's population and is currently estimated to cause 8 million new infections and 2-3 million deaths annually (Dye et al., 1999). The survival and persistence of *M. tuberculosis* depends on its capacity to manipulate multiple host defense pathways (Nguyen and Pieters, 2005). The genetic predisposition of the host in defense against mycobacterial infections is linked to the capacity of the macrophage to undergo apoptosis or necrosis upon infection, with the former response imparting a resistant and the latter a susceptible host phenotype (Pan et al., 2005). To determine the role of the inhibition of macrophage apoptosis for virulence of *M. tuberculosis*, we identified *M. tuberculosis* genetic loci necessary and sufficient for the inhibition of macrophage apoptosis. Here we show that the nuoG gene, which encodes a subunit of the NADH-Dehydrogenase Complex I of *M. tuberculosis*, is necessary for the inhibition of infection-induced apoptosis of macrophages and for virulence of the bacteria in the mouse model of tuberculosis. In addition, our results demonstrate that apoptosis is an important part of the host innate immune response to mycobacterial infections.

Figure 20:
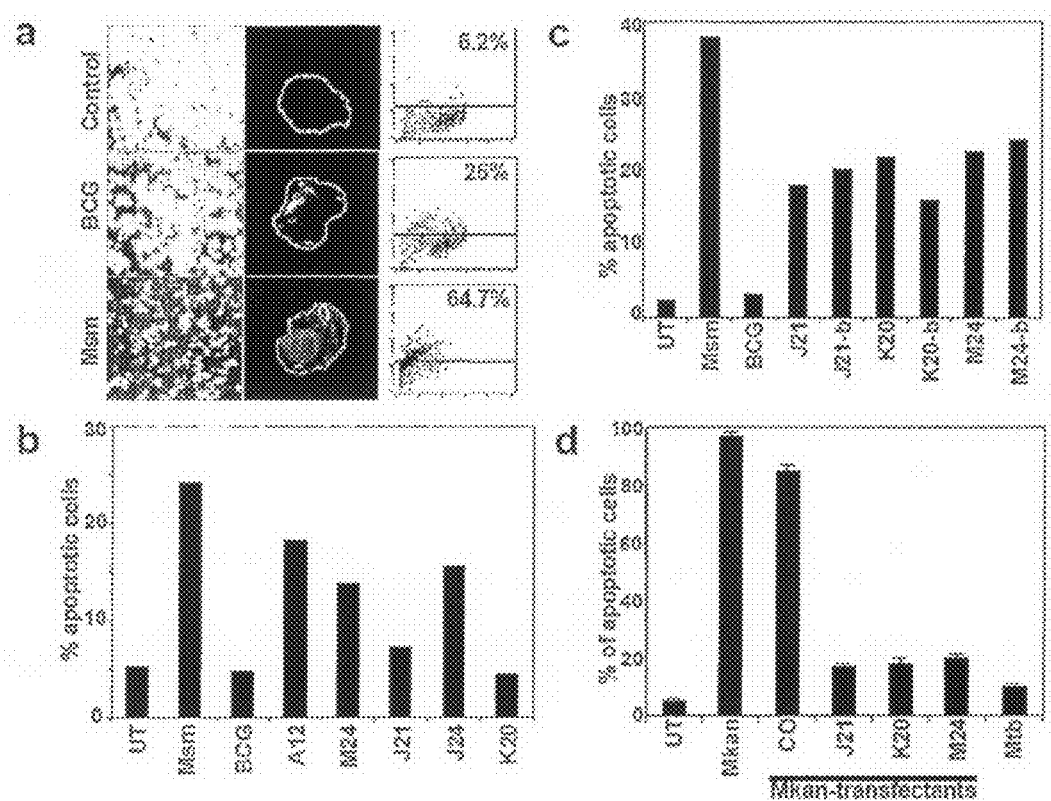
FIG. 20 is micrographs and graphs of experimental results identifying three independent regions in the M. tuberculosis genome that mediate the inhibition of macrophage apoptosis. Panel a. M. smegmatis induced more cell death in infected THP-1 cells than BCG as observed by bright field microscopy (left panels). Fluorescence microscopy showed TUNEL staining in M. smegmatis infected cells undergoing apoptosis (Middle panels; red fluorescence is TUNEL staining, and green fluorescence is GFP-labeled bacteria. The light areas in the center micrograph is almost entirely green; the light areas in the bottom micrograph are almost entirely red). Strong induction of apoptosis by M. smegmatis was confirmed by flow cytometry (right panels; Y-axis shows TUNEL staining, X-axis is forward light scatter which reveals marked reduction in cell size associated with massive cell death in the M. smegmatis-infected cultures). Panel b. M. smegmatis was transfected with an episomal cosmid library of M. tuberculosis genomic DNA and individual clones were screened for their capacity to inhibit apoptosis. The final screen was performed by TUNEL staining and flow cytometry. Untreated (UT) cells and M. smegmatis (Msm) and BCG infected THP-1 cells were compared to THP-1 cells infected with M. smegmatis carrying the indicated M. tuberculosis cosmid clones. Panel c. The cosmid DNA of three clones (J21, K20, M24) was purified and used to re-transfect M. smegmatis, resulting in clones J21-b, K20-b and M24-b. These clones along with the original transformants were tested for induction of apoptosis by infection of THP-1 cells and analyzed as in Panel b. Panel d. The three selected cosmid DNAs and empty vector cosmid (CO) were transfected into M. kansasii (Mkan), and the induction of apoptosis by the bacteria was compared to untreated (UT) and M. tuberculosis (Mtb) infected THP-1 cells using TUNEL assay at day 5 day of infection as in Panel b. p<0.01 for J21, M24, and K20 compared to CO by unpaired t-test. Results shown in Panels a through d are all representative of at least three independent experiments.
Figure 23:
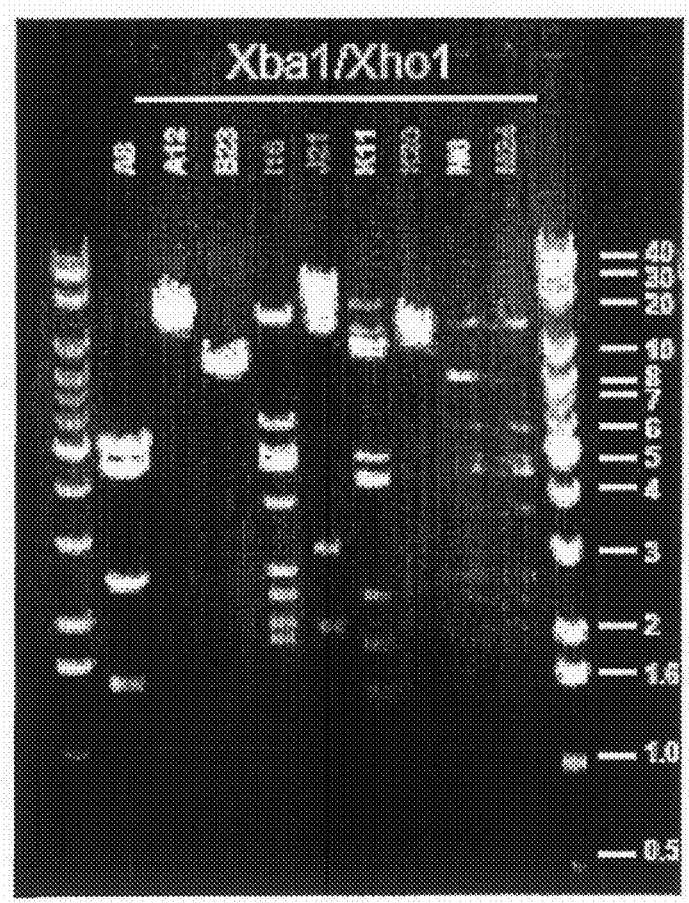
FIG. 23 is a graphic summary and a photograph of an ethidium bromide-stained gel illustrating the gain-of-function screen described in Example 2. The top panel summarizes the results from the gain-of-function screen. The bottom panel shows a restriction digest analysis of cosmid DNA of 9 selected clones. The final four selected clones are I16, J21, K20 and M24. Only the 8 kbp side band in the M6 lane is specific for M6; the other bands are spillover from the M24 lane.

Virulent species of mycobacteria have established mechanisms to counter the host cells effort to undergo apoptosis by inhibiting infection-induced apoptosis, a capacity that is not found in non-virulent species, and therefore a correlation between virulence and inhibition of macrophage apoptosis was proposed (Bakcewicz-Sablinska et al., 1998; Keane et al., 2000; Oddo et al., 1998; Sly et al., 2003). In the present study a "gain-of-function" genetic screen was established using the non-pathogenic M. smegmatis mc2155 because it is a fast-growing Mycobacterium that has been shown to be highly transformable (Snapper et al., 1990) and safe for use in studies of M. tuberculosis gene expression using standard BSL-2 laboratory practices (Bange et al., 1999). In our initial studies, we demonstrated that M. smegmatis mc2155 induced a very strong and rapid apoptosis response of a differentiated human macrophage-like cell line (PMA treated THP-1 cells) when compared to M. bovis BCG infected or uninfected macrophages (FIG. 20A). This result established the potential of M. smegmatis mc2155 to be used in the "gain-of-function" screen, and subsequently bacteria were transformed with a cosmid library of M. tuberculosis genomic DNA. A total of 312 individual random clones of M. smegmatis transformed by M. tuberculosis cosmids were screened for their ability to inhibit infection-induced apoptosis of THP-1 cells when compared to wild type M. smegmatis (FIG. 23). Assuming random representation of M. tuberculosis sequences by the cosmid transformants, 312 cosmid clones suggests that over 95% of the M. tuberculosis genes were represented. After three successive screens using bright field microscopy or flow cytometry to assess levels of cell death in infected THP-1 cells, 12 clones with markedly reduced cell death promoting activity were selected (FIGS. 20A and 23). The capacity of these clones to inhibit apoptosis was analyzed using a specific assay for apoptosis (TUNEL assay) followed by flow cytometry to determine the percentage of apoptotic cells (FIGS. 20A and B). Finally, three clones (designated K20, J21 and M24) showing the strongest inhibition of M. smegmatis-induced apoptosis in macrophages were selected.

Figure 24:
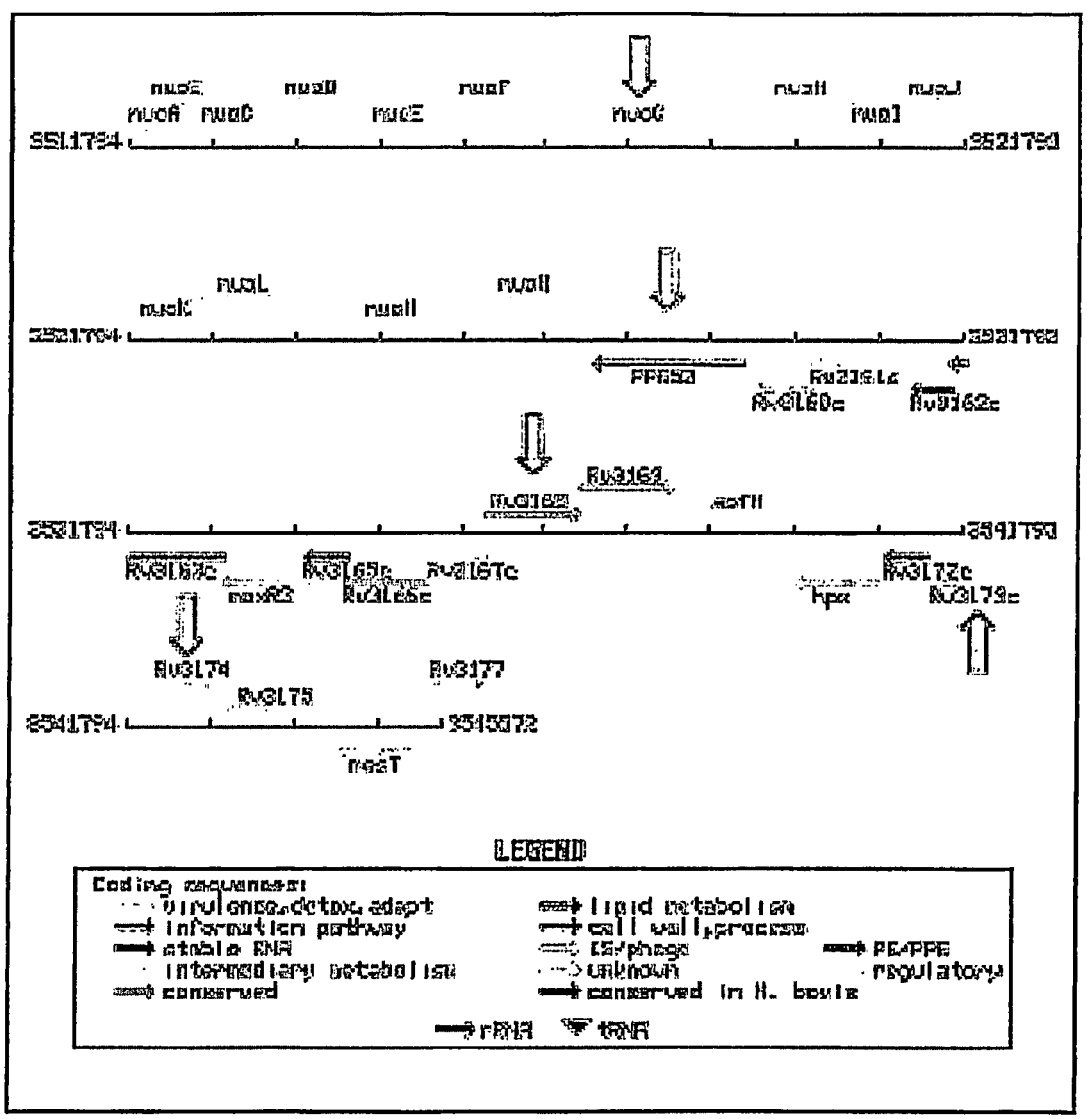
FIG. 24 is a diagram of the insert of cosmid J21. The diagram and legend was created using the TubercuList web server. The position of deletion mutants used to identify the gene that mediates the inhibition of infection-induced apoptosis are indicated. Arrows indicate single gene deletions and the large deletion from PPE53 to Rv3163c is marked.

The inserts of the three cosmids were analyzed by DNA sequencing and restriction enzyme digestion and found to be non-overlapping (FIGS. 23 and 24).

It was theoretically possible that genomic mutants of M. smegmatis that had lost their ability to induce apoptosis were selected during the screening process. To address this possibility, the episomal cosmid DNA of the three selected clones was extracted and again transfected into M. smegmatis mc2155. The capacity of the corresponding clones together with the original clones to induce apoptosis was analyzed. In all three cases the re-transformed clones had the same phenotype as the original clones, all leading to about 50% reduction of apoptosis when compared to wild-type bacteria (FIG. 20C). Thus, the phenotype of reduced apoptosis-induction was due to the transfected cosmid DNA and not to random genomic mutations in the M. smegmatis genome. Nevertheless, overall the effect of the cosmids on macrophage apoptosis was modest (about 50% reduction) which may have been due to the very strong capacity of M. smegmatis to induce apoptosis when compared to other mycobacteria (see FIG. 20A). We therefore tested the effects of the M. tuberculosis cosmids on apoptosis induction by another mycobacterial species, M. kansasii. This opportunistic pathogen is known to be a strong apoptosis-inducing mycobacterium, but it shows slower host cell killing than M. smegmatis with little apoptosis after one to three days of infection and a significant rise after 5-7 days of infection (data not shown and Balcewicz-Sablinska et al., 1998). Therefore we transformed the three isolated cosmid clones into M. kansasii to generate M. kansasii-J21, -M24, -K20, and an empty cosmid vector control to generate the M. kansasii control strain (M. kansasii-CO). THP-1 cells were harvested after 5 days of infection and the apoptosis assay by TUNEL staining and flow cytometry was performed. M. kansasii wild-type induced 95% apoptosis while the M. kansasii-J21, -K20 and -M24 showed 16%, 20% and 17% apoptosis respectively compared to 86% of apoptosis induced by M. kansasii-CO which was a significant reduction $p<0.01$, unpaired t-test) (FIG. 20D). M. tuberculosis H37Rv was used as a positive control that induced apoptosis only in 11% of the cells which was very similar to the 6% of apoptosis observed in untreated cells. Interestingly, all three cosmids transfected into M. kansasii reduced the apoptosis induction to a level very similar to M. tuberculosis.

Apoptosis of infected macrophages has been reported to be a pathway to either directly kill ingested bacteria (Molloy et al., 1994) or to facilitate killing of bacteria within apoptotic bodies phagocytosed by bystander macrophages (Fratazzi et al., 1997). Therefore we hypothesized that inhibition of apoptosis is important for mycobacteria in order to evade the host's innate immune response. The very strong inhibition of apoptosis observed for M. kansasii clones transformed with M. tuberculosis cosmids allowed investigation of this hypothesis.

Figure 21:
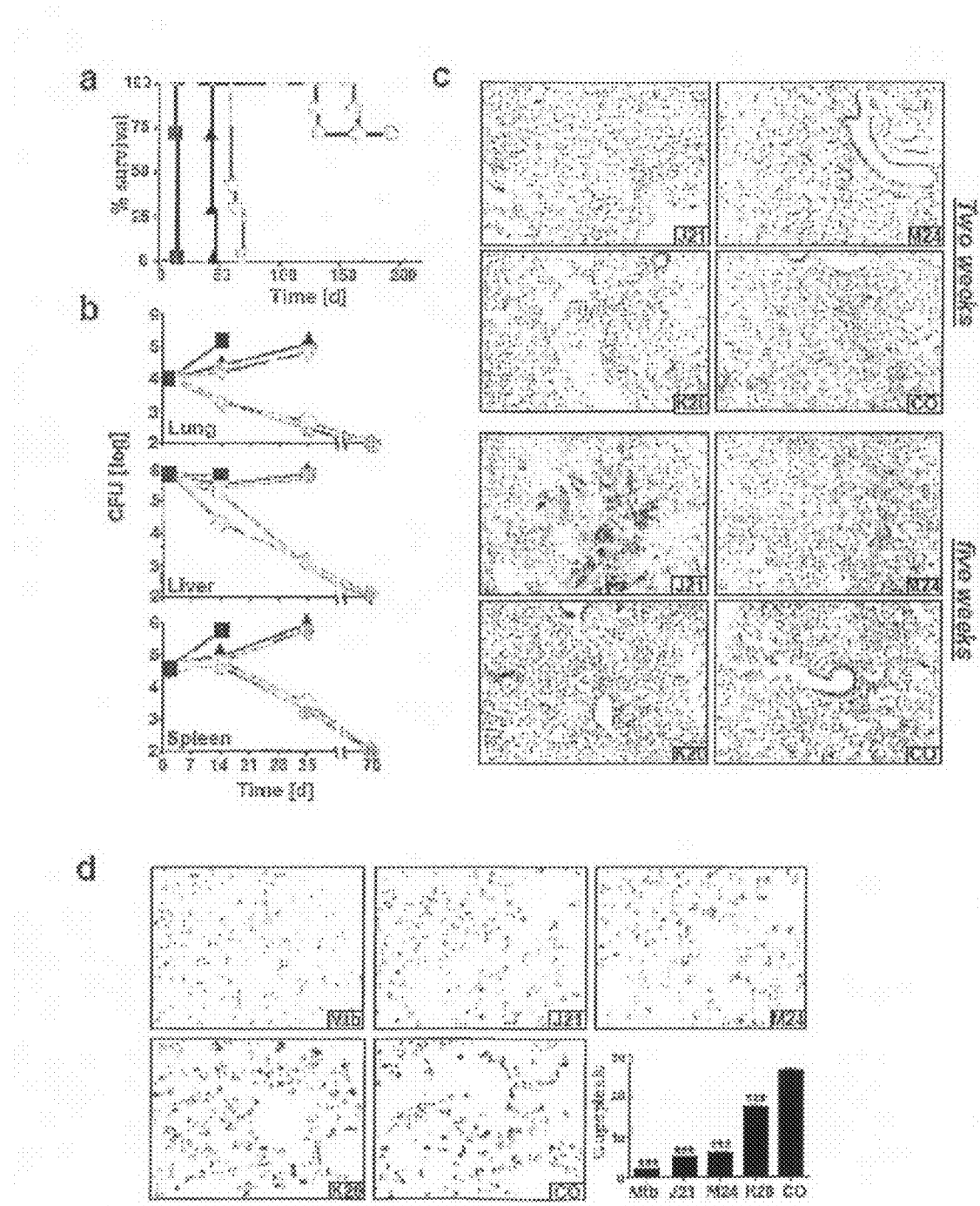
FIG. 21 is graphs and micrographs showing the correlation between apoptosis inhibition and mycobacterial virulence. SCID mice were infected with $10^6$ bacteria via the tail vain and survival (Panel a, seven mice per group), or the bacterial load in lung, liver and spleen was determined (Panel b, three mice per group). M. tuberculosis (squares), Mkan-J21 (triangle), Mkan-M24 (inverted triangle), Mkan-CO (circle) and Mkan-K20 (diamonds). Panel c, Lung histopathology of infected mice was analyzed after 2 and 5 weeks of infection. Panel d, Levels of apoptosis in the lungs after 2 weeks of infection were determined by TUNEL staining of tissue sections. Panels c and d show representative fields for infections with each bacterial strain as indicated. The graph in panel d shows quantitation of TUNEL positive cells, and asterisks indicate statistically significant reductions (p<0.005, unpaired t-test) compared to Mkan-CO infected mice. The results shown are representative of three independent experiments.

SCID mice (BALB/c background) were infected with the M. tuberculosis cosmid transformed M. kansasii clones (M. kansasii-J21, -K20, and -M124) intravenously. In addition mice were infected with M. tuberculosis H37Rv and the M. kansasii-CO as positive and negative controls. The median survival of SCID mice infected with M. tuberculosis H37Rv was 15 days, whereas median survival for mice infected with M. kansasii-CO was >200 days, since only 2 out of 7 mice died by the end of the observation period of 200 days (FIG. 21A). The mice infected with M. kansasii-J21-M24 had a median survival of 44 days or 60 days, respectively. The survival curves for both of these bacteria were very significantly different from the survival curve of M. kansasii-CO infected mice (p=0.0002, log rank test). Surprisingly, most of the M. kansasii-K20 infected mice survived the length of the experiment (2 out of 7 died), similar to M. kansasii-CO infected mice (p=0.87).

The results of the survival study were consistent with the data on the bacterial growth of the different strains in lung, liver and spleen of infected mice as analyzed after 24 hours, 2 and 5 weeks. All bacteria initially infected the analyzed organs in very similar numbers as determined by colony forming units (cfu) at the 24 h harvest (FIG. 21B). After two weeks, differences became apparent, most notably in the lung and spleen where mice infected with M. tuberculosis H37Rv showed a 10-fold increase in bacterial load, compared to M. kansasii-J21 and -M24 which remained the same and M. kansasii-K20 and M. kansasii-CO which showed a 10-fold decrease in cfu. After five weeks all M. tuberculosis infected mice were dead, the M. kansasii-J21 and M24 infected mice had a 10-fold increase in cfu in the lungs and spleens, and the M. kansasii-CO and K20 infected mice had a drastic reduction of bacterial growth in all three organs with about 100-1000 fold less cfu compared to the initial colonization (FIG. 21B), and this reduction continued until no bacteria could be detected after 10 weeks of infection.

Analysis of the histopathology of the lungs revealed that after 14 days the lung morphology was well preserved in all groups of mice (FIG. 21C), but after 35 days the lungs of M. kansasii-J21 infected mice were almost completely consolidated and in M. kansasii-M24 infected mice the lungs showed significant infiltration of cells. In contrast, lungs of mice infected with M. kansasii-K20 and M. kansasii-CO showed no signs of infiltration and had normal morphology even after 35 days. Interestingly, the lung pathology of M. kansasii-J21 correlated with early killing of mice when compared to the less severe pathology in M. kansasii-M24 infected mice, which also died later than *M. kansasii*-J21 infected mice. In order to correlate the virulence of the different strains with their capacity to inhibit apoptosis, lung sections obtained 14 days after infection were stained for apoptotic cells using a TUNEL based assay. Clearly, *M. tuberculosis*, *M. kansasii*-J21 and *M. tuberculosis*-M24 did not induce a strong apoptotic response in contrast to *M. kansasii*-K20 and -CO infected lungs (FIG. 21D). Quantification of apoptotic cells demonstrated a very low level of apoptotic cells in *M. tuberculosis* infected lungs (1-2%), a slight increase in *M. kansasii*-J21 and *M. tuberculosis*-M24 infected lungs (~5%) and a strong increase in *M. kansasii*-K20 (17%) and -CO (26%) infected lungs. Our results indicated that *M. tuberculosis* cosmids J21 and M24 mediated inhibition of host cell apoptosis in human THP-1 cells and also in vivo in the lungs of SCID mice. In contrast, cosmid K20 was similarly active in THP-1 cells but failed to show a significant effect in the in vivo mouse studies.

Since the cosmid J21 mediated the strongest increase in virulence of transfected *M. kansasii*, it was selected for further analysis. The sequence of the *M. tuberculosis* DNA was determined to start at by 3511794 and finish at by 3545572 as annotated in Cole et al., 1998 (FIG. 24). A literature search for *M. tuberculosis* genes implicated in virulence revealed that several genes encoded in this portion of the genome, including PPE 53, Rv3163c, Rv3173c and Rv3174, are upregulated by *M. tuberculosis* within macrophage phagosomes (Schnappinger et al., 2003). Another gene included in this interval, Rv3168, has been identified by transposon mutagenesis as important for survival of *M. tuberculosis* in infected mice (Sassetti and Rubin, 2003). We thus generated deletion mutants of *M. tuberculosis* H37Rv of each of these genes by specialized transduction (Bardarov et al., 2002)(FIG. 24). Furthermore, the nuo operon which is encoded by the first 15 kbp of the cosmid insert was selected to be disrupted by deletion of nuoG in *M. tuberculosis*. In addition, a mutant deleted in the region containing the genes PPE53 to Rv3163c was created (FIG. 24).

The impact of the deletion from *M. tuberculosis* of specific genes contained in cosmid J21 was analyzed initially using SCID mice. This showed that deletion of nuoG had the strongest effect on *M. tuberculosis* virulence, since median survival was increased from 16 days for wild-type *M. tuberculosis* to 31 days for the nuoG mutant (p=0.0031 as determined by the log rank test). All of the other deletions had minimal effects with the median survival of the mice ranging from 17-18 days, except for ΔRv3174 strain, which showed a median survival of 21 days. This was significantly different from *M. tuberculosis* (p=0.0031), and although a subtle effect, might also be of biological importance. Selected deletion clones were also analyzed for their capacity to inhibit infection-induced apoptosis using differentiated THP-1 cells. The deletion of nuoG resulted in a strong increase in apoptosis induction from 5% with wild-type bacteria to 25% with the nuoG bacteria (p=0.0027, two-tailed t-test). All of the other deletion clones showed only a slight increase of apoptosis induction (8-12%) that was statistically significant ($p<0.05$, two-tailed t-test) when compared to *M. tuberculosis* but was most likely of no biological importance since for example the ΔPPE53/Rv3163c deletion induced the most apoptosis second to ΔnuoG but had no effect on the virulence of the bacteria as documented by the survival experiment in FIG. 22A. Altogether, the results suggested that nuoG was a virulence gene that mediated most or all of the anti-apoptotic properties of the cosmid clone J21. To further confirm this conclusion, the nuoG strain was complemented with an integrating plasmid carrying a copy of nuoG behind a constitutively active promoter, and compared to wild-type and ΔnuoG strains for their capacity to kill infected SCID mice. The median survival times for mice infected with *M. tuberculosis* wild-type or the complemented strain were not significantly different (14 d and 16.5 d, respectively). In contrast, mice infected with ΔnuoG bacteria survived twice as long as those infected with wild-type bacteria (median survival of 27.5d, $p<0.0001$ using the log rank test (FIG. 22C)).

In conclusion, the "gain-of-function" genetic screen successfully led to the identification of the first *M. tuberculosis* gene to our knowledge to be implicated in the inhibition of infection-induced macrophage apoptosis. The gene, nuoG, is part of the NADH-dehydrogenase complex I that consists of 14 proteins encoded by one operon. A nuoG mutant of *Salmonella* serotype Gallinarum has previously been shown to protect chickens against experimental fowl typhoid (Zhang-Barver et al., 1998). The nuoG subunit is most likely localized on the extracellular part of the protein complex (Friedrich and Bottcher, 2004). Currently, it is not clear which if any specific genes of the operon are needed in addition to nuoG for the function of apoptosis inhibition. While the mechanism by which nuoG may directly or indirectly lead to inhibition of host cell apoptosis remains to be determined, it is intriguing that other studies have implicated host cell mitochondria as a target for bacterial virulence and host response evasion strategies (Blanke, 2005). In this regard, it is interesting that the mammalian ortholog of nuoG is a substrate of caspase-3 cleavage, which mediates initiation of pro-apoptotic events culminating in the loss of mitochondrial potential (Ricci et al., 2004). This suggests the possibility that the product of the nuoG gene of *M. tuberculosis* might be capable of replacing the function of its mammalian counterpart, thus maintaining the mitochondrial electron transport chain and blocking the cascade of events leading to apoptosis.

The capacity of *M. tuberculosis* to inhibit host cell apoptosis was suggested by earlier studies to be a virulence factor (Bakcewicz-Sablinska et al., 1998; Keane et al., 2000; Oddo et al., 1998; Sly et al., 2003), a hypothesis that is strongly supported by the more recent demonstration of the importance of host cell apoptosis induction for resistance or susceptibility to tuberculosis (Pan et al., 2005). Our results demonstrate for the first time, through the use of well-defined bacterial mutants, the importance of apoptosis inhibition for the virulence of *M. tuberculosis* and the major role that host cell apoptosis has in the innate immune response to *M. tuberculosis* infections.

Materials and Methods

Bacteria and culture conditions. *M. smegmatis* (mc2155) (Snapper et al., 1990), *M. kansasii* (ATCC 12478) and *M. tuberculosis* strain H37Rv (ATCC 25618). GFP expressing BCG and *M. smegmatis* were generated by subcloning the enhanced GFP gene (BD Bioscience Clontech) into the mycobacterial expression vector pMV261. The new plasmid named pYU921 was transfected into competent cells by electroporation as in Snapper et al., 1990. All bacteria were cultured as described in Snapper et al., 1990 and Bange et al., 1999

Generation of a genomic library of *M. tuberculosis* in the cosmid vector pYUB415. The strategy has been previously described in Bange et al., 1999. Briefly, *M. tuberculosis* (strain Erdman) genomic DNA was purified and partially digested with Sau3A. DNA fragments of about 40 kbp were selected by agarose gel purification and ligated into arms of cosmid vector pYUB415 digested with XbaI and BamH1 prepared as in Bange et al., 1999. DNA was packaged in vitro with Gigapack XL (Stratagene) and *E. coli* were transduced and selected on LB-plates containing 100 μg/ml ampicillin.

Over 10⁵ independent clones were pooled, and DNA for transformation was obtained using standard alkaline lysis method.

Tissue Culture conditions and Infection. Human myelomonocytic cell line THP1 (ATCC TIB-202) was cultured and differentiated using phorbol myristate acetate (PMA)(Sigma) as in Dao et al., 1991. Bacteria were grown to an $OD_{600}$ ranging from 0.5 to 0.8 and were sonicated twice for 20 s using a cup horn sonicator (Laboratory Supplies, Inc.) and allowed to settle for 10 min. The infection was carried out at a multiplicity of infection (MOI) of 10:1 (10 bacilli to 1 cell) for 4 hours in triplicate wells. After 4 hours, the extracellular bacteria were removed by four washes with phosphate buffered saline (PBS). The cells were incubated in DMEM (Invitrogen) with 20% human serum (Sigma) and 100 µg/ml of gentamycin (Invitrogen) and apoptosis assay was performed.

Figure 22:
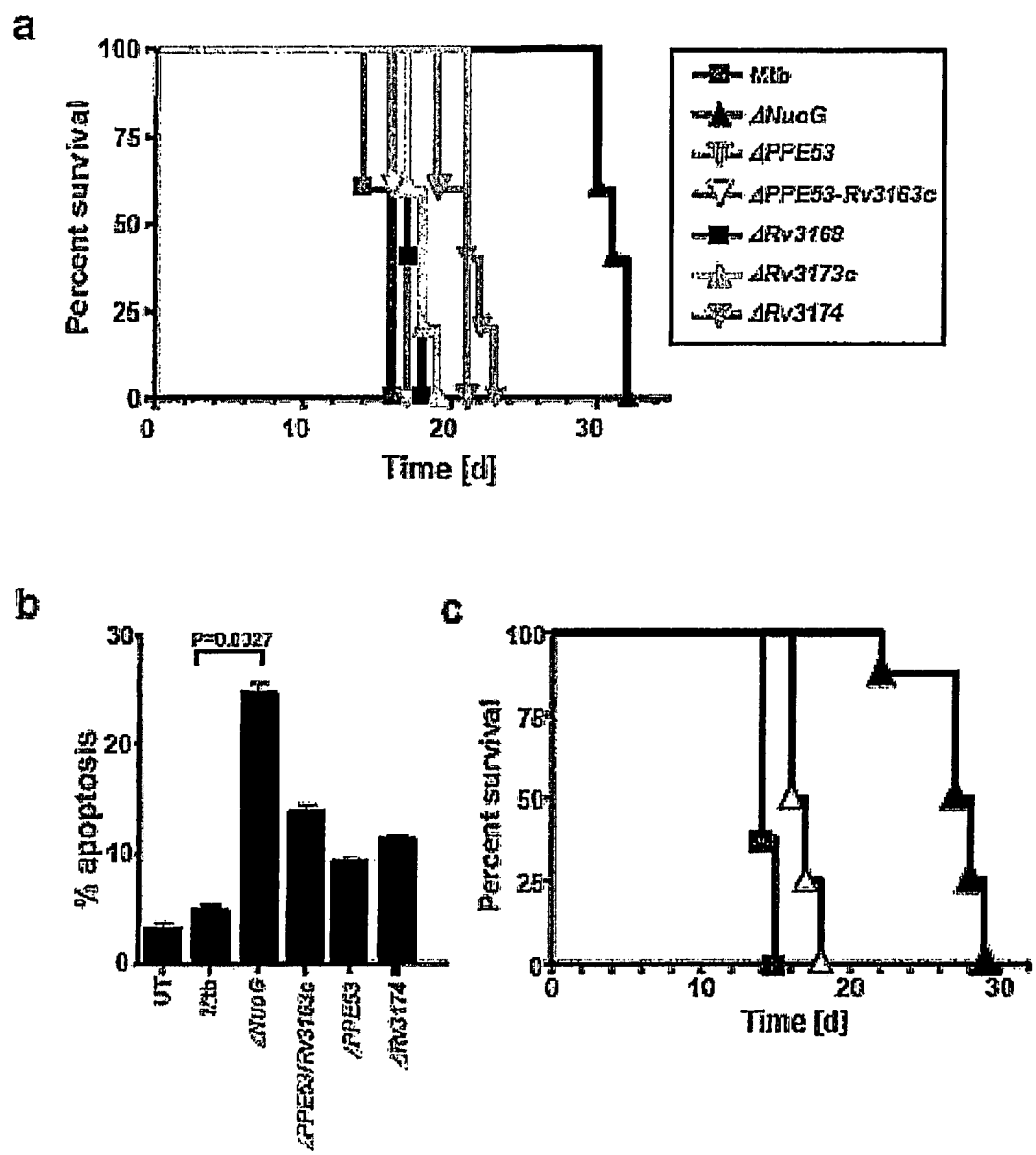
FIG. 22 is graphs identifying nuoG as a mycobacterial virulence determinant. Selected genes of the cosmid J21 were deleted in M. tuberculosis by specialized transduction and the resulting strains were analyzed for their virulence in SCID mice (Panel a) and for their capacity to inhibit infection-induced apoptosis in human macrophages (Panel b). The ΔnuoG bacteria were complemented with nuoG. The virulence of the wild-type (square), ΔnuoG (triangle) and complemented (open triangle) M. tuberculosis strains was compared in SOD mice (Panel c). Results shown are representative of two experiments for Panels a and c and three for (panel b).

Apoptosis Assay. A TUNEL assay was performed to reveal apoptosis-induced DNA fragmentation using the In Situ Cell Death Detection Kit-Flourescein (Roche Applied Sciences). Triplicate wells were either pooled after infection (FIGS. 20B and C) or analyzed independently (FIGS. 20D and 22B). The assay was carried out as described in Dau et al., 1991 and the percentage of stained cells was analyzed using flow cytometry.

Transformation and gain of function screen. Transformations were performed by electroporation of competent mycobacteria as described in Snapper et al., 1990. For the initial screen, M. smegmatis was transformed with the genomic DNA cosmid library described above and 312 cosmid clones were picked and grown in liquid medium containing 50 µg/ml hygromycin. Differentiated THP-1 cells were infected and the effect of the cosmid clones on the monolayer of cells was compared to that of wild-type M. smegmatis by microscopy and subsequently by FACS analysis of PI or TUNEL stained cells (FIG. 23).

Four successive rounds of screening identified 4 clones of greatest interest, and their cosmid DNA was purified and screened by restriction digest (FIG. 23). For cosmid J21, the 5' and 3' ends of the insert-DNA were sequenced and aligned with the published genomic M. tuberculosis DNA sequence (FIG. 24).

Figure 25:
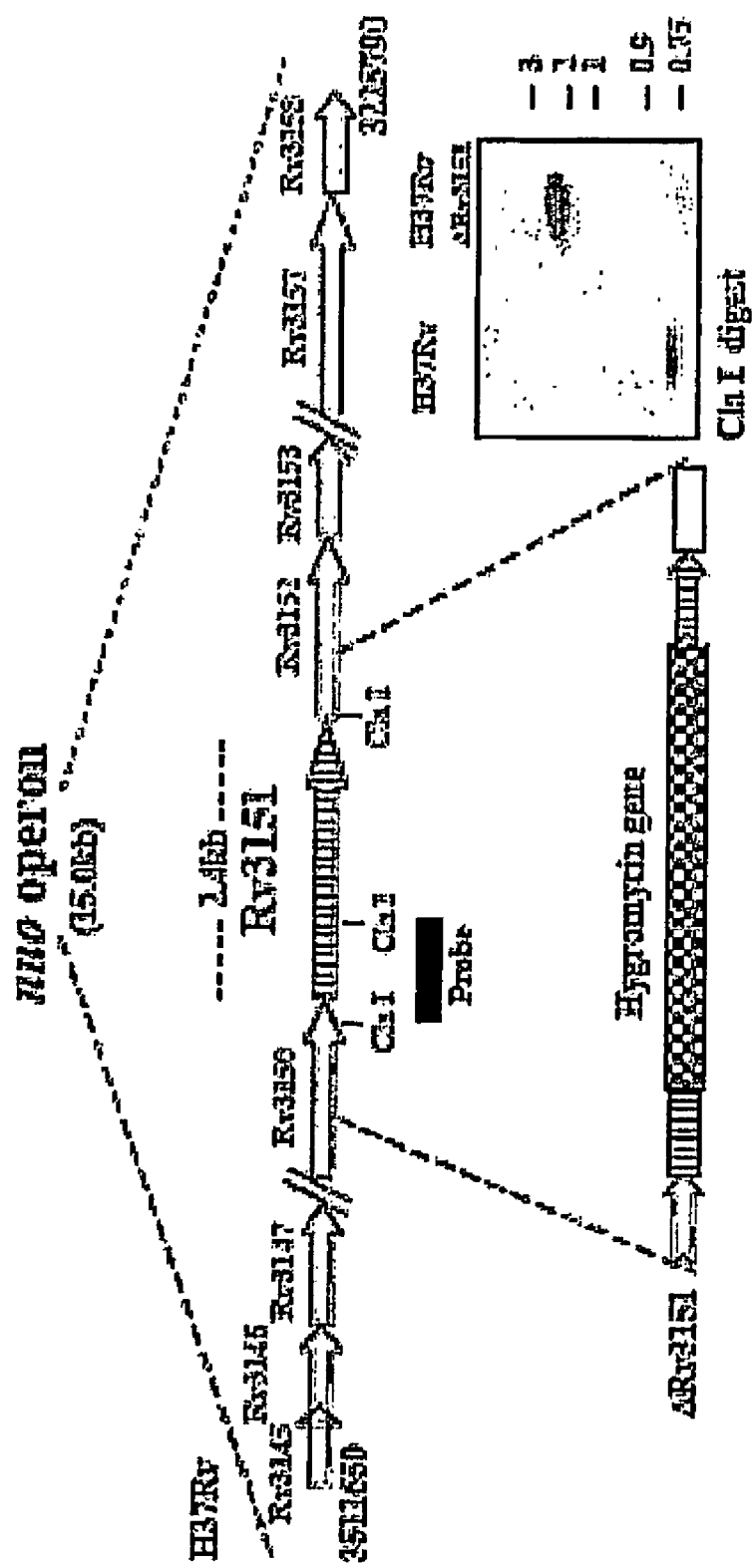
FIG. 25 is a diagram and a photograph of a Southern blot illustrating the creation of a nuoG null mutant in *M. tuberculosis*. The hygromycin cassette was introduced into the genome via specialized transduction. The insertion was confirmed by Southern blot using the radiolabeled probe hybridizing at the indicated position.

Specialized transduction and complementation. Specific genes of M. tuberculosis were disrupted using specialized transduction as described in Bardarov et al., 2002. For the nuoG::hyg-null allele, the hygromycin resistance cassette was introduced between the first 4 by of the nuoG 5' end and the last 163 by of the 3' end of the open reading frame. The successful deletion of the gene was demonstrated by Southern blotting as described previously (FIG. 25). For complementation of the ΔnuoG strain, the open reading frame of nuoG was amplified by PCR and subcloned behind a constitutive promoter into the plasmid pMV361, which allows integration into the genome of M. tuberculosis (Stover et al., 1991).

Animal studies. BALB/c or SCID/Ncr (BALB/c background) mice (4-6 weeks old females, purchased from the NCI) were infected intravenously through the lateral tail vein with $1 \times 10^6$ bacteria. For survival studies groups of 10 mice were infected, and after 24 h three mice per group were sacrificed to determine the bacterial load in the organs. In order to follow the bacterial growth an additional three mice per timepoint were infected. The organs (lung, spleen, liver) were homogenized separately in PBS/0.05% TWEEN-80, and colonies were enumerated on 7H10 plates grown at 37° C. for 3-4 weeks. For histopathology, tissues were fixed in 10% buffered formalin and embedded in paraffin; 4 µm sections were stained with haematoxylin and eosin. TUNEL staining was performed on the paraffin-embedded tissue sections using the In Situ Cell Death detection kit, POD (Roche Applied Sciences) as per the manufacturer's protocol. Quantification was performed blinded by counting the amount of apoptotic cells per ~200 total cells in 8 separate areas of two lung sections for each of the three mice per group. All animals were maintained in accordance with protocols approved by the Albert Einstein College of Medicine Institutional Animal Care and Use Committee.

Statistical Analysis. All statistical analysis was performed using PRISM® 4 (GraphPad Software).

EXAMPLE 3

Immunological Evaluation of ΔnlaA and ΔsecA2 Mutants

The ability of ΔnlaA (Example 1) and ΔsecA2 mutants (Braunstein et al., 2003) to induce host apoptosis and immunity to mycobacteria was evaluated using immunological and flow cytometric methods.

Figure 26:
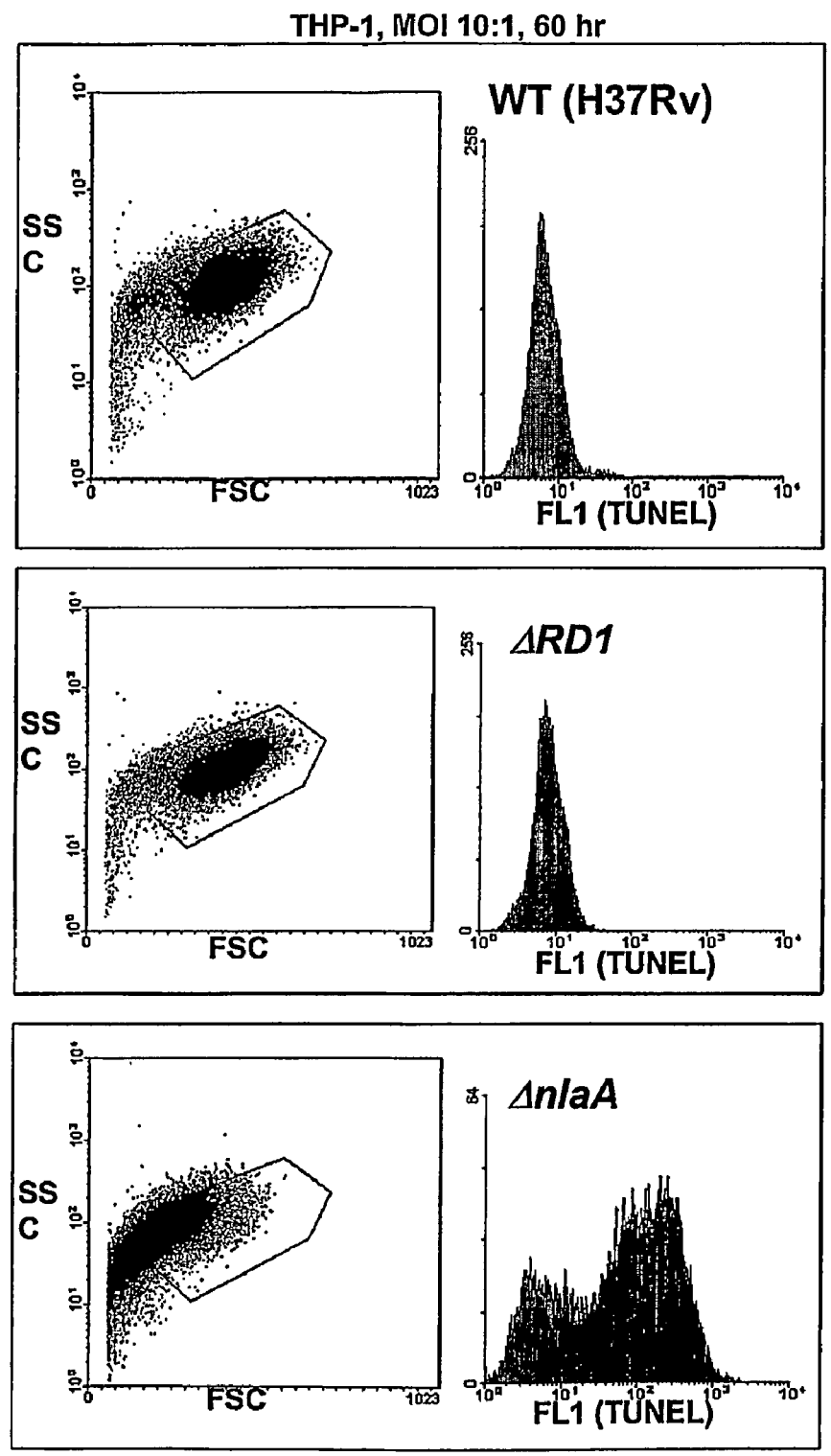
FIG. 26 is graphs of forward light scattering and TUNEL assays showing induction of apoptosis in THP-1 cells by *M. tuberculosis* ΔnlaA.
Figure 27:
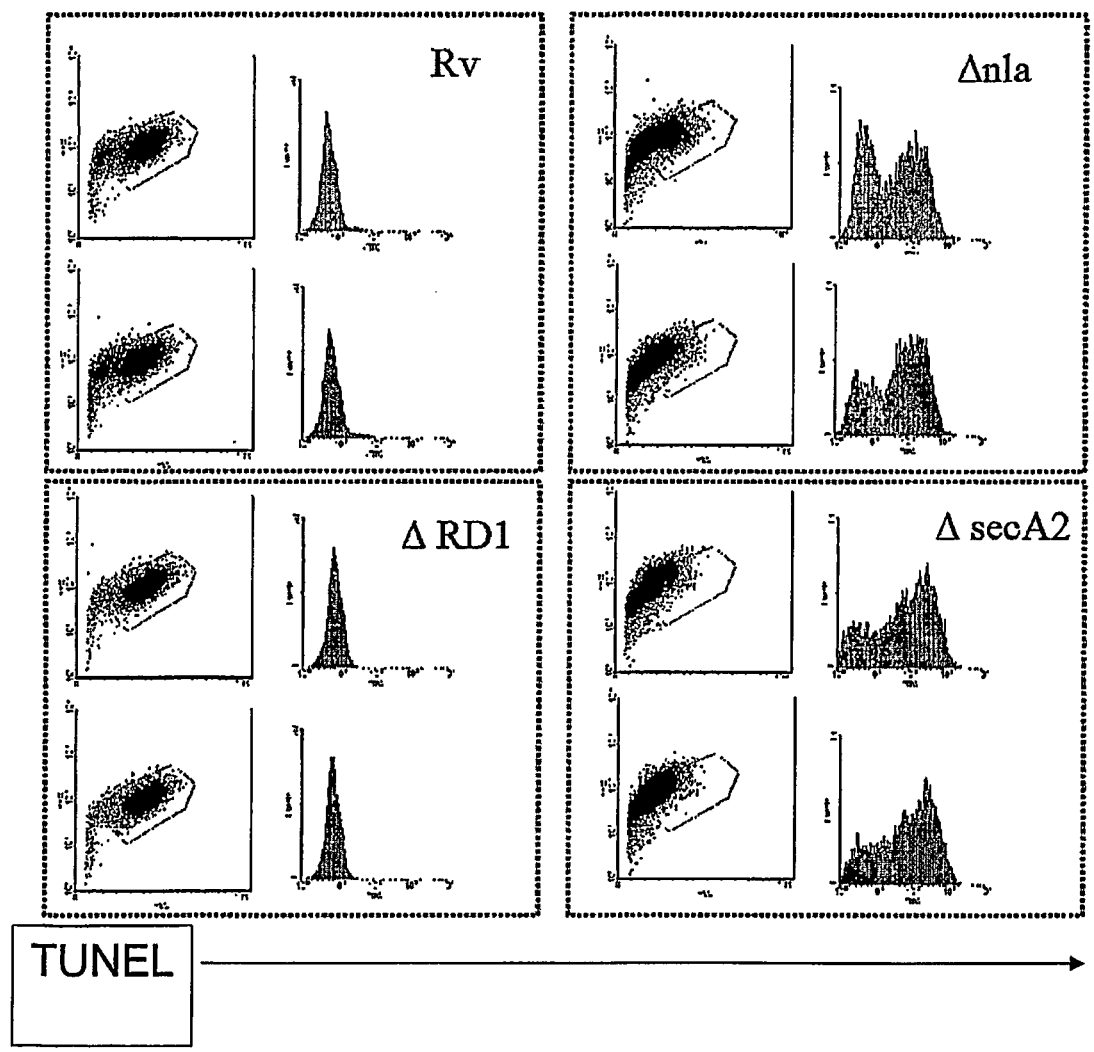
FIG. 27 is graphs of forward light scattering and TUNEL assays showing induction of apoptosis in THP-1 cells by *M. tuberculosis* ΔnlaA and ΔsecA2 cells.

THP-1 cells (human myeloid/monocytic cell line) were infected with M. tuberculosis strains H37Rv, ΔRD1 (Hsu T, et al., 2003), ΔnlaA and ΔsecA2 at an MOI of 10:1. The cells were harvested after 60 hours, and analyzed by TUNEL as follows. The cells were stained with the In Situ Cell Death Kit (Roche), which labels strand breaks by the terminal deoxynucleotidyl transferase-mediated addition of fluorescein dUTP to free 3'-OH DNA ends. The size and complexity of the infected THP-1 cells was assessed by measurement of forward and side light scattering, and DNA fragmentation was assayed by determination of fluorescein incorporation using fluorescence-activated cell sorter (FACS) (Schrijvers et al., 2004) THP-1 cells infected with ΔnlaA or ΔsecA2, but not Rv or ΔRD1, showed extensive apoptosis (FIGS. 26 and 27).

Figure 28A:
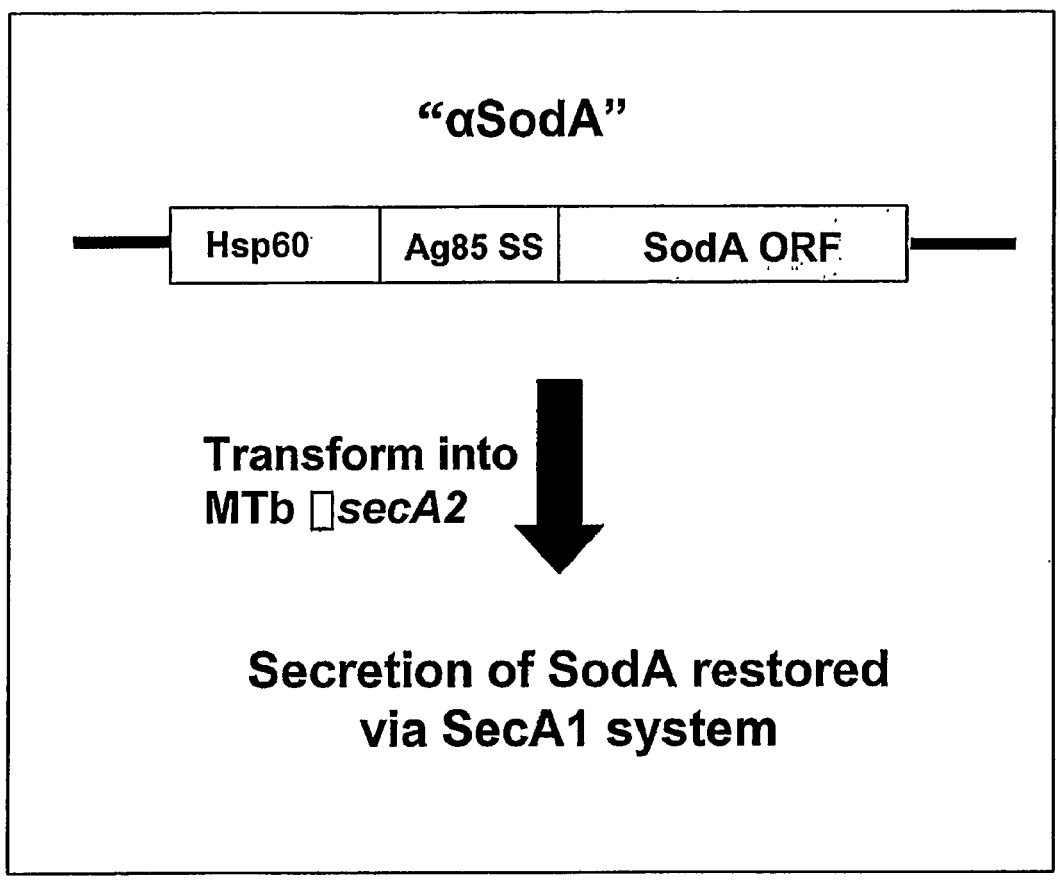
FIG. 28 is a diagram and graphs of TUNEL assays showing that restoring SodA secretion by a ΔsecA2 mutant reverses the effect of the secA2 deletion on host cell apoptosis. Panel A is a diagram of the strategy for restoring SodA secretion in a ΔsecA2 *M. tuberculosis* by expression of a transgenic SodA gene. Panel B is graphs of TUNEL assays showing induction of host cell apoptosis by ΔsecA2 *M. tuberculosis* but not by ΔsecA2-αSodA *M. tuberculosis*.
Figure 28B:
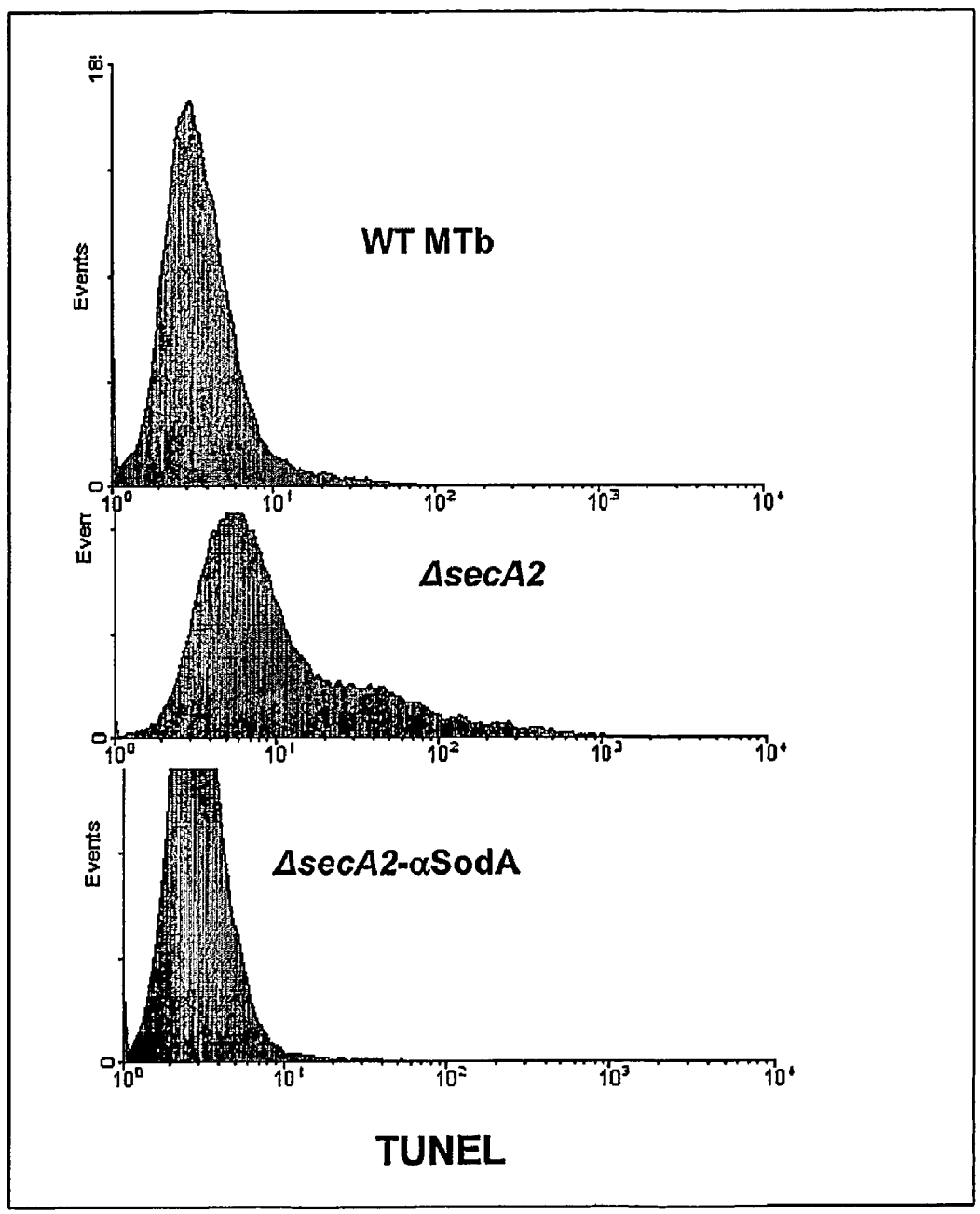

The M. tuberculosis SecA2 gene in superoxide dismutase A (SodA) secretion (Braunstein et al., 2003). Deleting SecA2 from virulent M. tuberculosis attenuates the virulence of the mycobacterium in mice. To evaluate whether the SecA2 superoxide dismutase prevents apoptosis, SodA activity was restored by transfecting an M. tuberculosis ΔsecA2 mutant with an αSodA plasmid construct (FIG. 28A). That vector features an Hsp60 promoter and an Ag85 signal sequence driving expression of a SodA gene (Braunstein et al., 2000). This plasmid drives the constitutive expression of a SodA protein that is secreted by the SecA1 system. This provides a SodA protein that is not dependent on SecA2 and thus complements the defective secretion of SodA from the ΔSecA2 mutant. THP-1 cells were infected with the wild type M. tuberculosis H37Rv, the ΔSecA2 mutant, and the ΔSecA2-αSodA SOD restored strain and the extent of apoptosis of the THP-1 cells was evaluated using TUNEL as described above. As shown in FIG. 28B, the ΔSecA2 mutant induced apoptosis, but the ΔSecA2-αSodA strain restored the ability of the mycobacterium to inhibit apoptosis. This indicates that the secretion of SodA protein can be directly responsible for inhibition of infection-induced apoptosis.

Figure 29:
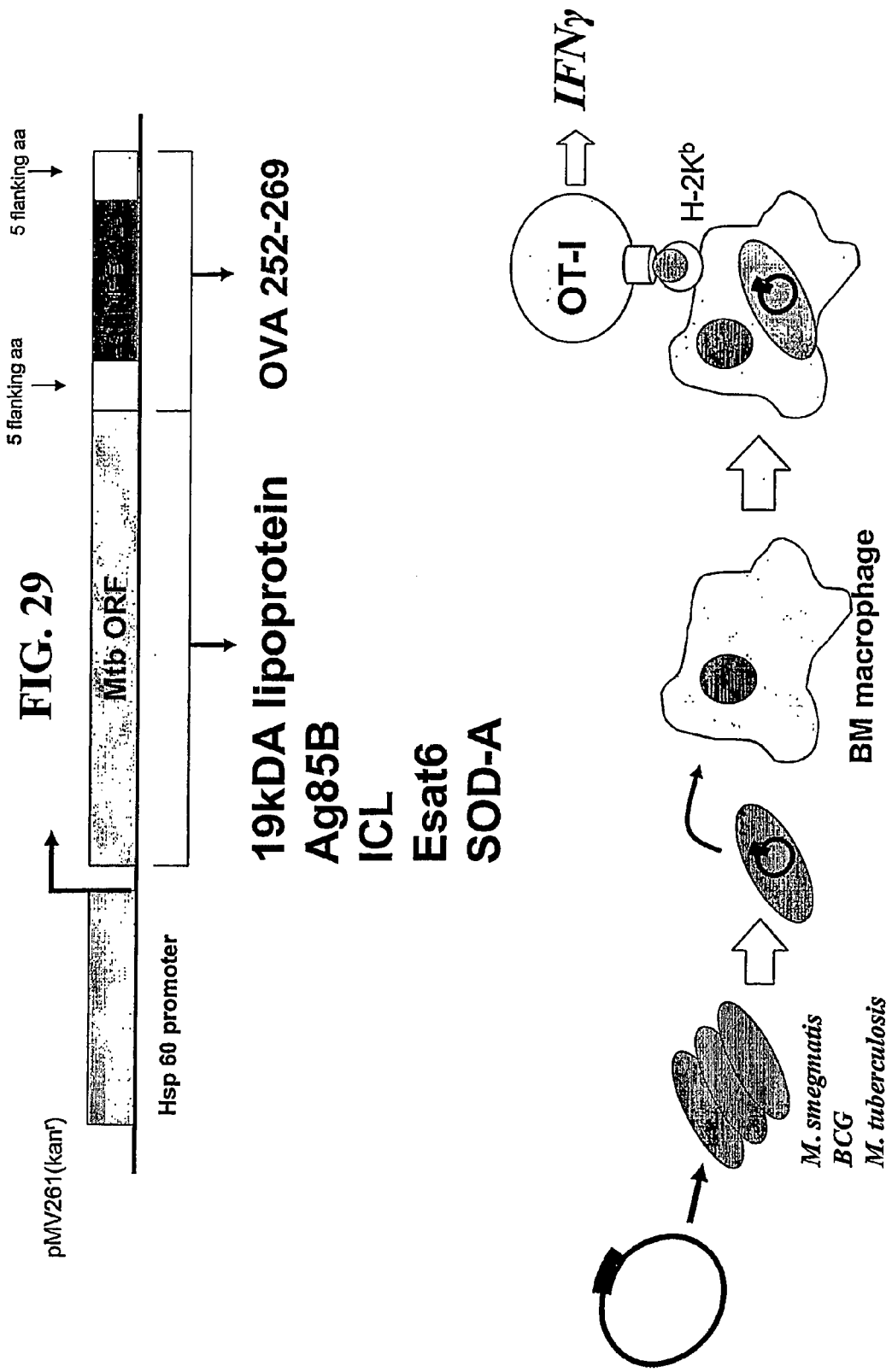
FIG. 29 is a diagram of the strategy used to evaluate the ability of various transgenic mycobacteria to induce interferon-γ (IFNγ) from OT-1 cells after exposure to macrophages. The mycobacteria are transfected with fusion proteins of *M. tuberculosis* antigens and the ovalbumin antigen SIINFEKL. Fusion proteins from transgenic mycobacteria that are apoptotic will be presented on the macrophage, where the SIINFEKL epitope will be recognized by the OT-1 cells, inducing IFNγ production by the OT-1 cells.
Figure 30:
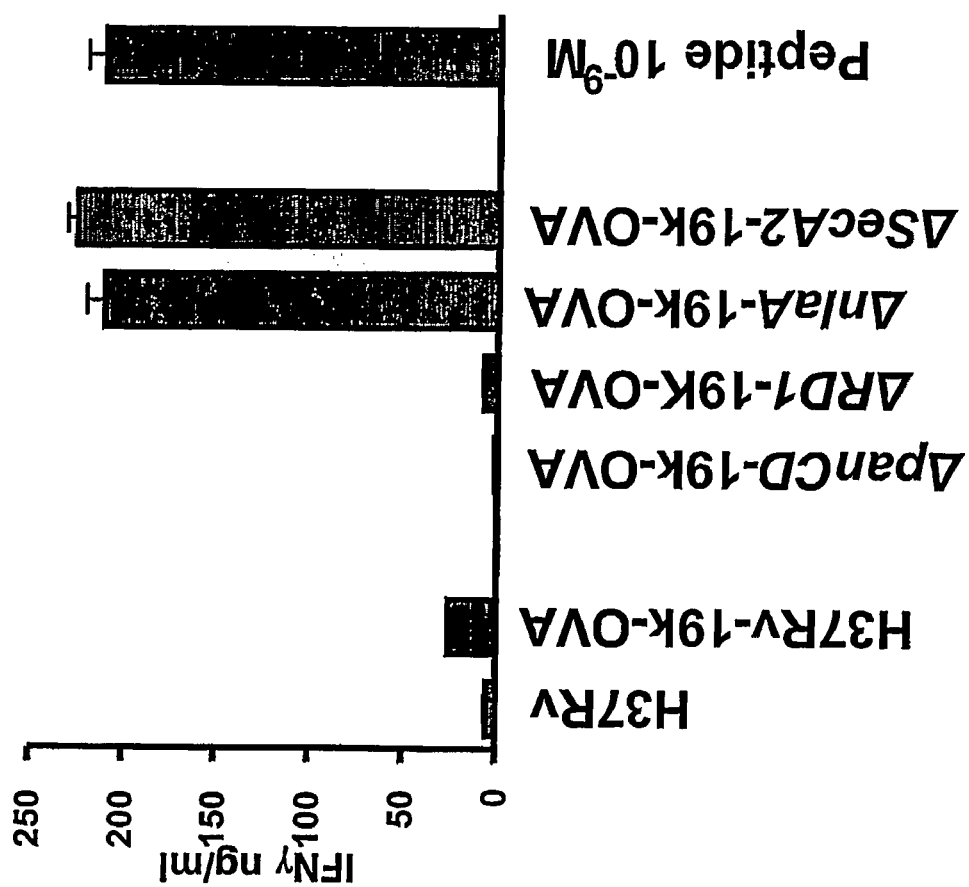
FIG. 30 is a graph of experimental data showing in vitro cross-presentation of the SIINFEKL peptide (OVA) by infected bone marrow-derived macrophages. The IFNγ production by the ΔnlaA-19k-OVA and ΔSecA2-19k-OVA indicates that the ΔnlaA and ΔSecA2 mutants are apoptotic.
Figure 31:
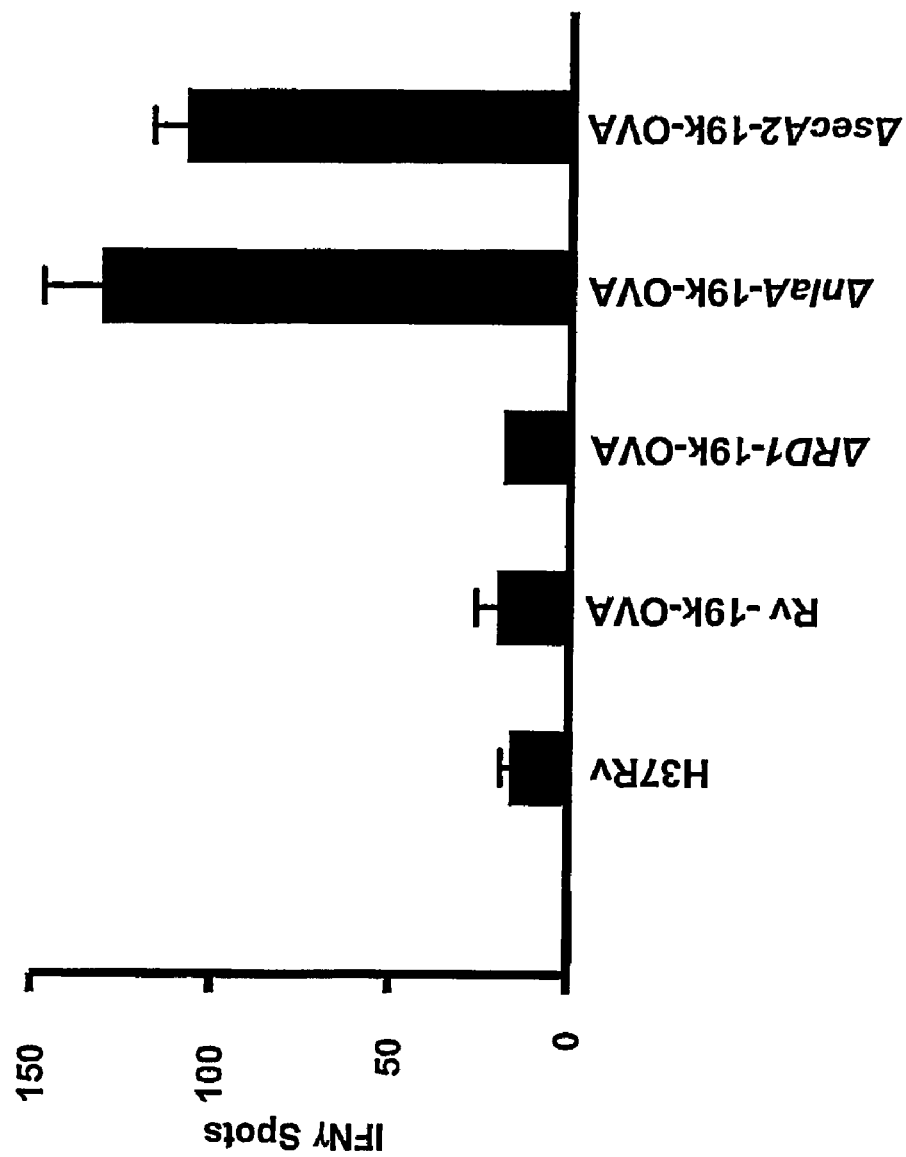
FIG. 31 is a graph of experimental data showing in vivo CD8 T cell priming by *M. tuberculosis* OVA (SIINFEKL)-expressing mutants with specific IFNγ ELISPOT analysis of splenocytes harvested on day 7 after i.v. mouse infection. The IFNγ production by the ΔnlaA-19k-OVA and ΔSecA2-19k-OVA indicates that the ΔnlaA and ΔSecA2 mutants are apoptotic.

Apoptosis is believed to function in host defense by making pathogen antigens available for presentation by bystander dendritic cells (Schaible et al., 2003; Yrlid and Wick, 2000). To determine if macrophages present more pathogen antigens when infected with mycobacteria that induce apoptosis than when infected with mycobacteria that do not induce apoptosis, the apoptosis-inducing mycobacterial strains ΔsecA2 and ΔnlaA, and the apoptosis-suppressing strains H37Rv (virulent), ΔRD1 and ΔpanCD (attenuated virulence—See International Patent Publication No. WO 03/070164 A2, incorporated herein by reference) were transfected with plasmid constructs comprising the 19 kDA lipoprotein antigen fused to the coding sequence for amino acid residues 252-269 (SIINFEKL) of chicken ovalbumin (OVA) under the control of the Hsp 60 promoter (FIG. 29), creating ΔsecA2-19k-OVA, ΔnlaA-19k-OVA, H37Rv-19k-OVA, ΔRD1-19k-OVA and ΔpanCD-19k-OVA. Each of these strains was combined with bone marrow-derived macrophages to allow infection of the macrophages, then T cells from TCR transgenic OT-1 mice (SIINFEKL/H-2K$^b$ specific) were added and interferon-γ (IFN γ) was measured by ELISA. The OVA peptide antigen is presented on the MHC Class I H-2K$^b$ molecule on the macrophages, where the OVA antigen is recognized by the T cell receptor on OT-1 cells, causing production of IFNγ (FIG. 29). As shown in FIG. 30, only the strains that allow host apoptosis, ΔsecA2-19k-OVA and ΔnlaA-19k-OVA, stimulated OT-1 production of IFNγ.

Figure 32:
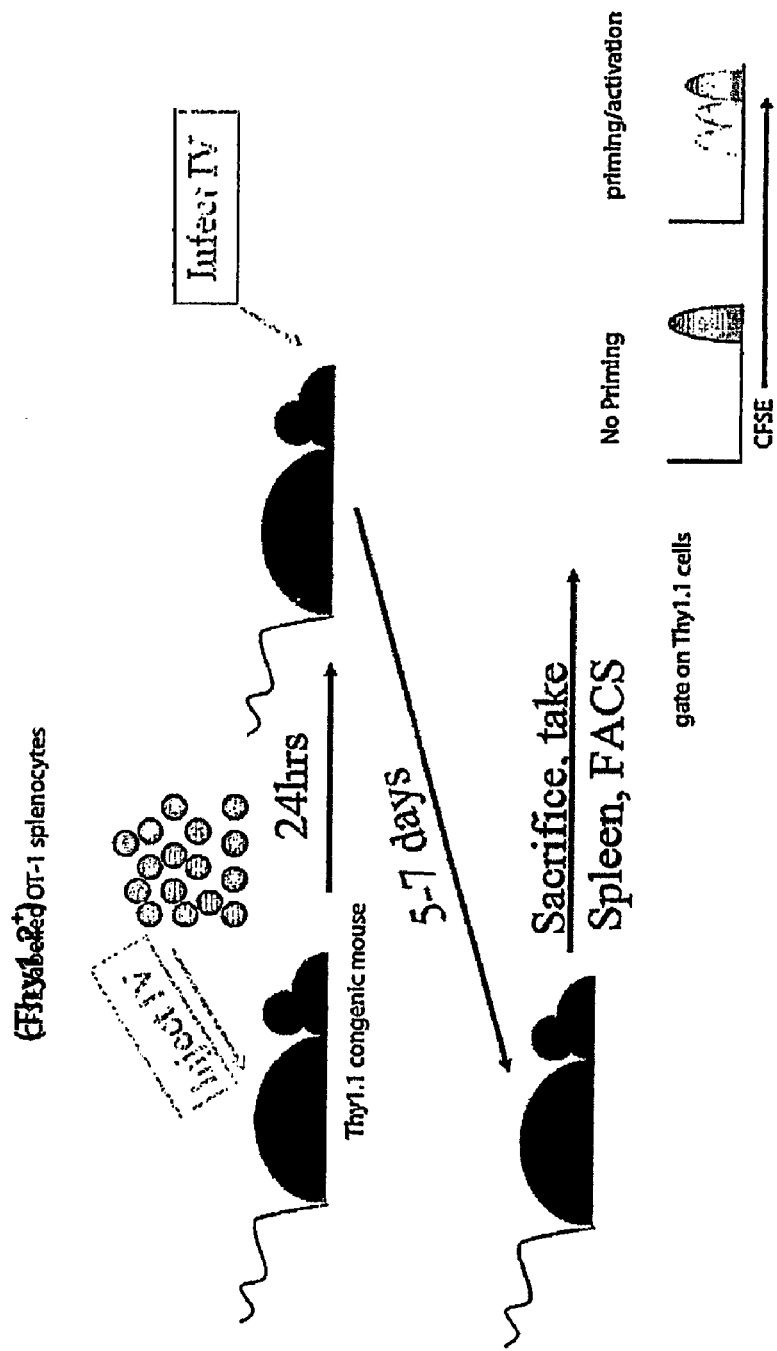
FIG. 32 is a diagram showing the strategy for determining the effect of infection with a mycobacterium on proliferation of carboxy-fluorescein diacetate, succinimidyl ester (CFSE)-labeled OT-1 splenocytes.
Figure 33:
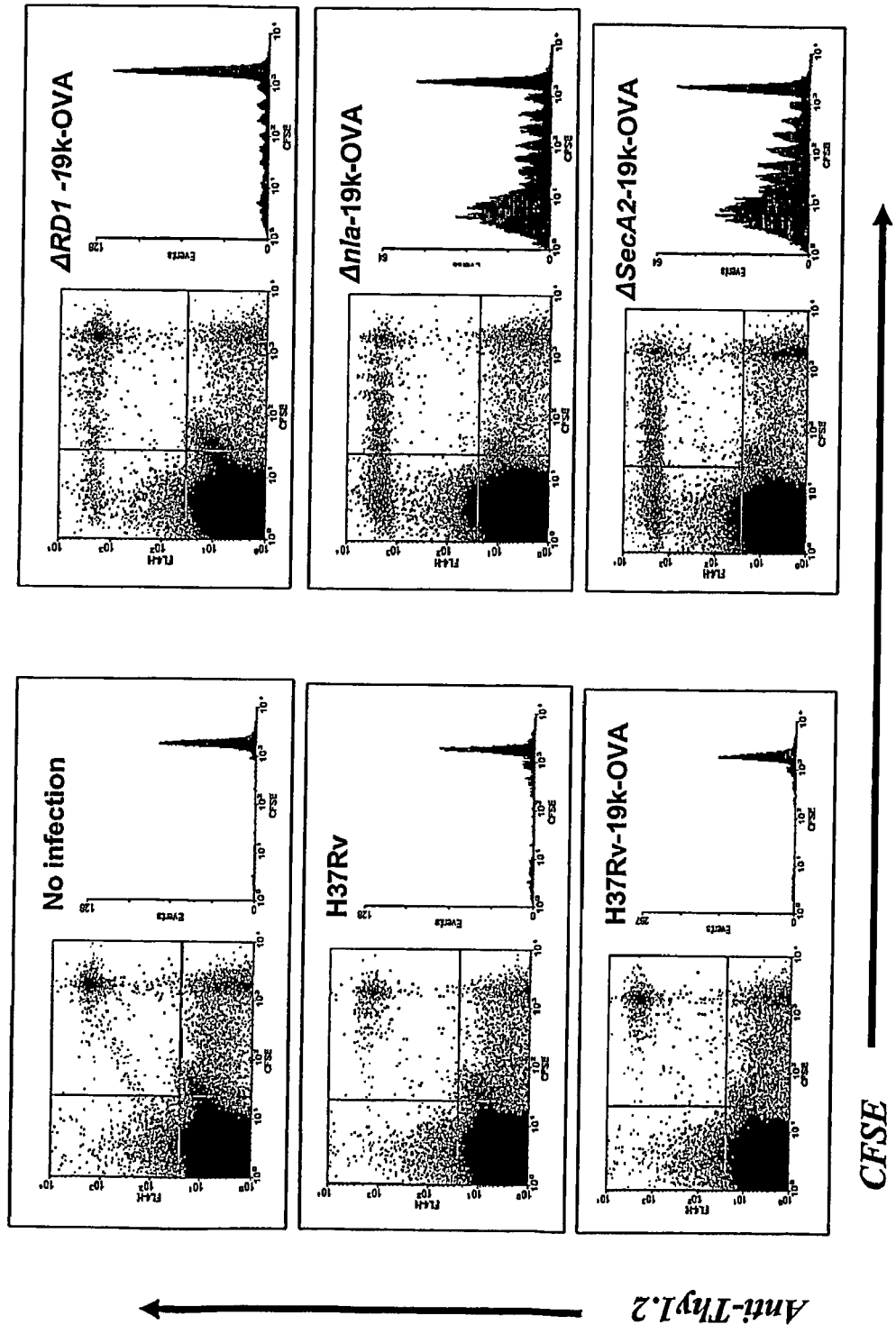
FIG. 33 is graphs of experimental results showing the activation of naïve CD8$^+$ T cells by apoptosis-inducing *M. tuberculosis* mutants ΔnlaA-19k-OVA and ΔSecA2-19k-OVA.

The ability of the above-described mutants expressing the transgenic 19k-OVA fusion protein to stimulate splenocyte proliferation in vivo was determined by injecting OT-1 splenocytes (Thy 1.2+) labeled with 5(6)-carboxyfluorescein diacetate N-succinimidyl ester (CFSE) into Thy1.1 congenic mice then, after 24 hours, infecting the mice with the mutant mycobacterium. After 5-7 days, the mice were sacrificed and their splenocytes were analyzed by FACS to determine the intensity of CFSE fluorescence in the Thy1.2+ T cells (FIG. 32). The CFSE enters the cells and binds irreversibly to intracellular and cell surface proteins by reaction with amines. When cells divide, the fluorescence intensity of each daughter cell is halved, so a proliferating cell population (e.g., antigen-activated T cells) exhibits a flow cytometry fluorescence profile as shown at the bottom right of FIG. 32. Results of these experiments are shown in FIG. 33. Only the strains that allow host apoptosis, ΔsecA2-19k-OVA and ΔnlaA-19k-OVA, exhibited OT-1 T cell activation in vivo. This indicates that apoptosis of infected cells promotes priming and activation of T cells against mycobacterial antigens.

Figure 34:
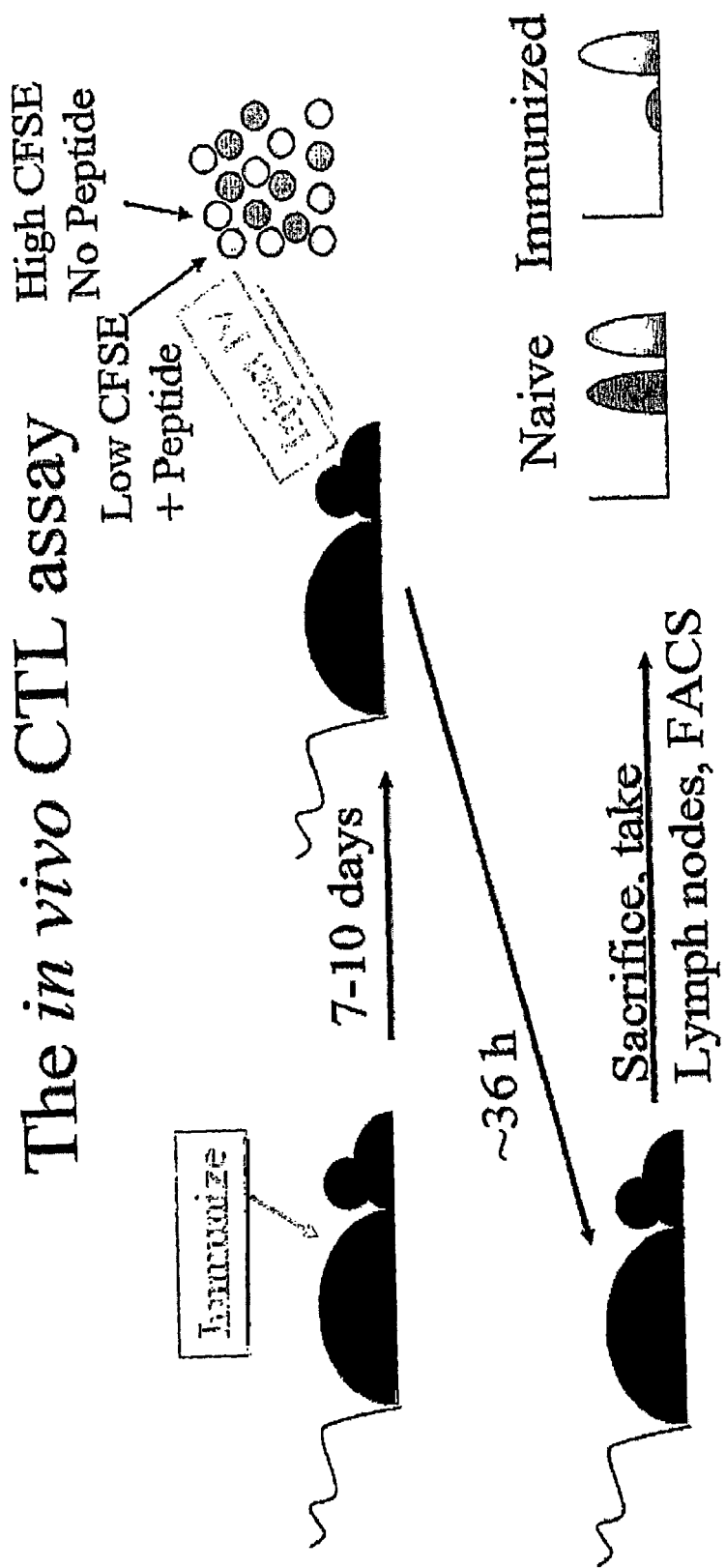
FIG. 34 is a diagram showing the strategy for determining the ability of a mycobacterium to induce a CTL immune response in vivo.

The ability of the apoptosis-inducing mutants to induce an immune response to mycobacterial antigens was further evaluated with the in vivo cytotoxic T lymphocyte (CTL) assay outlined in FIG. 34. Mice were immunized with the 19k-OVA antigen mycobacterial strains described above. After 7-10 days, the mice were then injected with 10$^7$ Thy1.2+ T cells that were either labeled with (a) a low concentration of CFSE and the OVA SIINFEKL peptide, or (b) a high concentration of CFSE without the OVA peptide. About 36 h later, the mice were sacrificed and FACS analysis was performed to quantify low and high-intensity fluorescing lymph node cells. Where the mouse has a CTL response specific for the OVA peptide, that response would kill only the CFSE$^{lo}$ cells; the CFSE$^{hi}$ cells should be unaffected and serve as a control.

Figure 35:
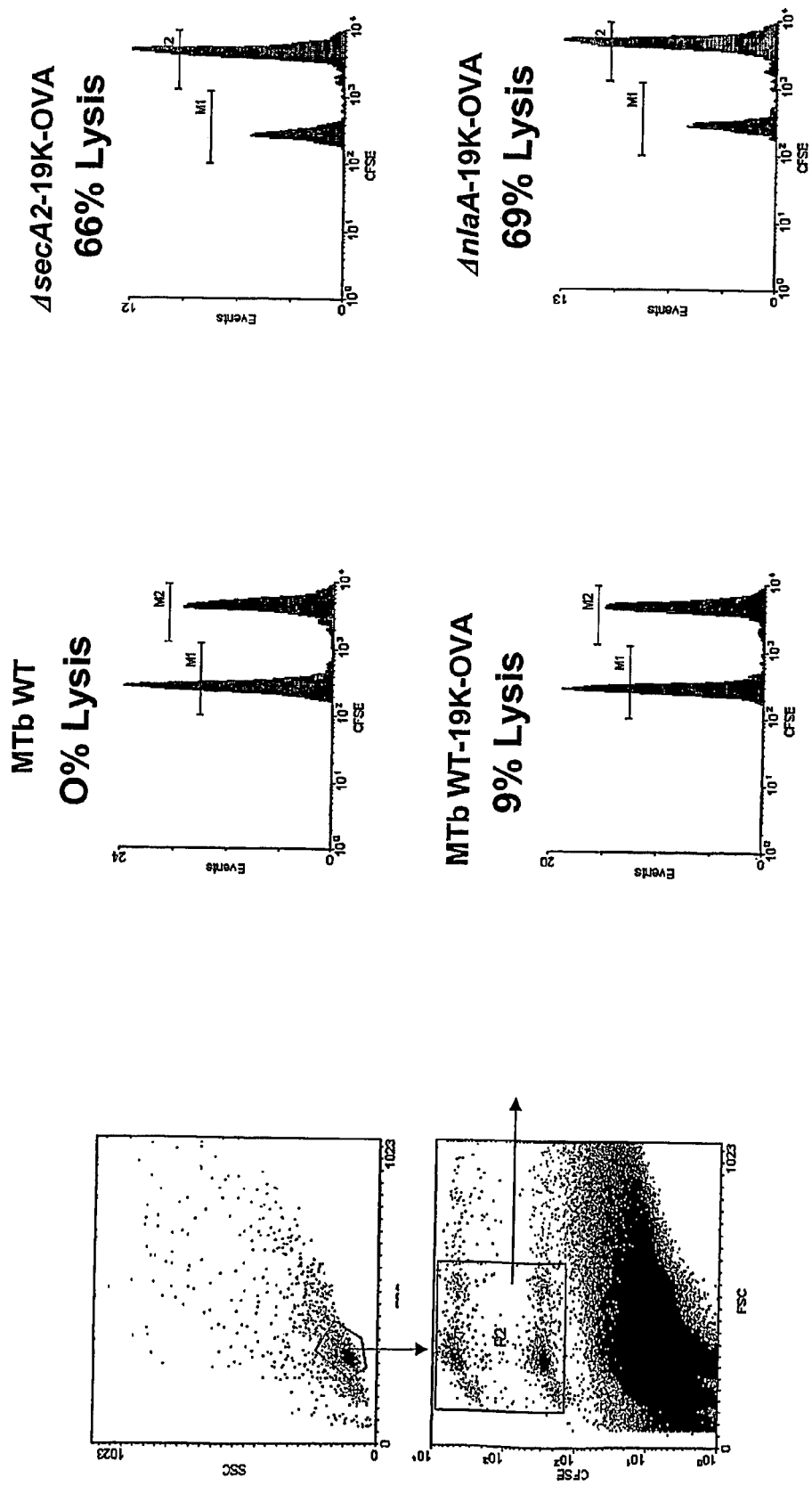
FIG. 35 is graphs of experimental results showing that *M. tuberculosis* mutants ΔnlaA-19k-OVA and ΔSecA2-19k-OVA induces a CTL response to cells presenting the 19k-OVA antigen.

FIG. 35 shows results of that assay. The mice immunized with the apoptosis-inducing mycobacteria mounted a CTL response to the OVA antigen-bearing T cells, whereas the mice immunized with the analogous mycobacteria that did not induce apoptosis did not mount the CTL response.

EXAMPLE 4

Inoculation with *Mycobacterium tuberculosis* Mutants that Inhibit Host Apoptosis Attenuates Infection with Virulent *Mycobacterium tuberculosis*

Mice were vaccinated with 10$^6$ organisms of *M. bovis* BCG, the transgenic *M. tuberculosis* with the nlaA deletion described in Example 1 (ΔnlaA in Table 1), a transgenic *M. tuberculosis* combining the ΔsecA2 and ΔnlaA deletions described above (ΔsecA2/ΔnlaA), and a transgenic *M. tuberculosis* having deletions in RD1 and pan, as described in International Patent Publication No. WO 03/070164 A2, incorporated herewith by reference, and expressing a transgenic listeriolysin (as in Grode et al., 2005)(ΔRD1/Δpan-listeriolysin). Two months following vaccination, the mice were challenged with 200 CFUs of *M. tuberculosis* Erdman by aerosol route. TB growth in the lungs and spleens were evaluated at 1 month and 3 months post-challenge. Results are provided in Table 1.

TABLE 1

Values are in log$_{10}$.

|  | Lungs | Spleens |
|---|---|---|
| 1 month: | | |
| Naive | 6.30 ± 0.06 | 5.35 ± 0.07 |
| BCG | 4.92 ± 0.07 (−1.38) | 4.24 ± 0.18 (−1.11) |
| ΔnlaA | 4.52 ± 0.15 (−1.78) | 4.04 ± 0.24 (−1.31) |
| ΔsecA2/ΔnlaA | 5.25 ± 0.08 (−1.05) | 4.27 ± 0.20 (−1.08) |
| 3 months: | | |
| Naive | 5.43 ± 0.02 | 4.93 ± 0.10 |
| BCG | 4.92 ± 0.14 (−0.51) | 4.31 ± 0.11 (−0.62) |
| ΔnlaA | 4.56 ± 0.16 (−0.87) | 3.79 ± 0.26 (−1.14) |
| ΔsecA2/ΔnlaA | 5.17 ± 0.14 (−0.26) | 4.88 ± 0.09 (−0.05) |

In a second experiment using the same protocol, protection with *M. tuberculosis* ΔsecA2 and ΔnlaA, along with BCG, was evaluated (Table 2).

TABLE 2

| Group | 1 mo. lung | 1 mo. spleen | 3 mo. lung | 3 mo. spleen |
|---|---|---|---|---|
| naive | 6.67 ± 0.08 | 4.61 ± 0.04 | 5.78 ± 0.02 | 4.79 ± 0.03 |
| ΔsecA2 | 4.77 ± 0.07 (−1.90) | 3.84 ± 0.11 (−0.77) | 5.16 ± 0.05 (−0.62) | 4.49 ± 0.15 |
| ΔnlaA | 5.34 ± 0.08 (−1.33) | 4.04 ± 0.19 (−0.57) | 5.38 ± 0.09 (−0.40) | 4.67 ± 0.07 |
| BCG | 5.52 ± 0.02 (−1.15) | 3.76 ± 0.08 (−0.85) | 5.73 ± 0.14 | 4.67 ± 0.09 |

Cytokine induction by BCG, the ΔnlaA mutant, and the ΔsecA2/ΔnlaA mutant was also determined. Two months after vaccination with 10$^6$ organisms, mice were challenged with 200 CFUs of *M. tuberculosis* Erdman by aerosol route. At 10 days post-challenge, lung cells were removed and analyzed for cytokine message using real-time PCR (cells directly without in vitro stimulation). The results are reported in Table 3 as message levels relative to the GAPDH housekeeping gene.

TABLE 3

| Expt. Group | IFN-γ | IL-12 | IL-4 |
|---|---|---|---|
| Naive | 4.0 | 30 | 0.8 |
| BCG | 27 | 25 | 0.3 |

TABLE 3-continued

| Expt. Group | IFN-γ | IL-12 | IL-4 |
|---|---|---|---|
| ΔnlaA | 32 | 16 | 0.3 |
| ΔsecA2/ΔnlaA | 39 | 20 | 1.3 |

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A recombinant *mycobacterium* having deletion of nlaA gene or deletion of a portion of nlaA gene, wherein the mutation deletion increases the ability of the *mycobacterium* to induce apoptosis of a mammalian macrophage infected by the recombinant *mycobacterium*.

2. The *mycobacterium* of claim 1, wherein the nlaA gene encodes a protein that is at least 99% homologous to SEQ ID NO: 1.

3. The *mycobacterium* of claim 1, deletion is of the entire nlaA gene (ΔnlaA).

4. The *mycobacterium* of claim 1, wherein the deletion is of a portion of the nlaA gene.

5. The *mycobacterium* of claim 1, further comprising a mutation, wherein the *mycobacterium* exhibits attenuated virulence in a mammal when compared to the *mycobacterium* without the mutation.

6. The *mycobacterium* of claim 5, wherein the mutation is a deletion in at least a portion of an RD1 region, or a deletion in a gene controlling production of a vitamin or an amino acid.

7. The *mycobacterium* of claim 1, wherein the *mycobacterium* is *M. smegmatis*, *M. bovis*, *M. avium*, *M. phlei*, *M. fortuitum*, *M. lufu*, *M. paratuberculosis*, *M. habana*, *M. scrofulacium*, *M. intracellulare*, *M. tuberculosis*, or *M. kansasii*.

8. The *mycobacterium* of claim 7, wherein the *mycobacterium* is an *M. boris*.

9. The *mycobacterium* of claim 1, wherein the *mycobacterium* is *M. tuberculosis*.

10. The *mycobacterium* of claim 1, further comprising a recombinant gene operably linked to a promoter that directs expression of the gene when the *mycobacterium* infects a mammalian cell.

11. The *mycobacterium* of claim 10, wherein the gene encodes an antigen of a mammalian pathogen.

12. A method of inducing an immune response in a mammal, the method comprising inoculating the mammal with the *mycobacterium* of claim 1.

13. The method of claim 12, wherein the *mycobacterium* further comprises a mutation in a nuoG gene, wherein the mutation increases the ability of the *mycobacterium* to induce apoptosis of a mammalian macrophage infected by the *mycobacterium*.

14. A method of making a recombinant *mycobacterium*, the method comprising eliminating expression of the nlaA gene in the *mycobacterium*.

* * * * *